United States Patent
Dimitrov et al.

(10) Patent No.: US 8,911,728 B2
(45) Date of Patent: Dec. 16, 2014

(54) HIGH-AFFINITY FULLY FUNCTIONAL SOLUBLE SINGLE-DOMAIN HUMAN CD4, ANTIBODIES, AND RELATED FUSION PROTEINS

(75) Inventors: Dimiter S. Dimitrov, Frederick, MD (US); Weizao Chen, Frederick, MD (US)

(73) Assignee: The United States of America, as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/699,535

(22) PCT Filed: May 20, 2011

(86) PCT No.: PCT/US2011/037439
§ 371 (c)(1),
(2), (4) Date: Jan. 11, 2013

(87) PCT Pub. No.: WO2011/146891
PCT Pub. Date: Nov. 24, 2011

(65) Prior Publication Data
US 2013/0108636 A1 May 2, 2013

Related U.S. Application Data

(60) Provisional application No. 61/467,570, filed on Mar. 25, 2011, provisional application No. 61/347,088, filed on May 21, 2010.

(51) Int. Cl.
| | | |
|---|---|---|
| A61K 39/00 | (2006.01) | |
| A61K 39/21 | (2006.01) | |
| A61K 39/385 | (2006.01) | |
| A61K 39/42 | (2006.01) | |
| C07K 16/10 | (2006.01) | |

(52) U.S. Cl.
CPC ......... *C07K 16/1063* (2013.01); *C07K 2317/92* (2013.01); *C07K 2319/32* (2013.01); *C07K 2317/76* (2013.01); *C07K 2319/30* (2013.01); *C07K 2317/64* (2013.01); *C07K 2317/569* (2013.01)
USPC ................... 424/135.1; 424/178.1; 424/188.1; 424/192.1; 424/193.1; 424/208.1; 424/139.1; 424/160.1

(58) Field of Classification Search
None
See application file for complete search history.

(56) References Cited

FOREIGN PATENT DOCUMENTS

| WO | WO 03/095492 A1 | 11/2003 |
|---|---|---|
| WO | WO 2004/058820 A2 | 7/2004 |

(Continued)

OTHER PUBLICATIONS

Langner et al., "Antiviral effects of different CD4-immunoglobulin constructs against HIV-1 and SIV: immunological characterization, pharmacokinetic data and in vivo experiments," Arch Virol 130: pp. 157-170 (1993).*

(Continued)

*Primary Examiner* — Michelle S Horning
*Assistant Examiner* — M. Franco Salvoza
(74) *Attorney, Agent, or Firm* — Leydig, Voit & Mayer, Ltd.

(57) ABSTRACT

The invention provides engineered antibody domains (eAds), a polypeptide comprising a single domain CD4, as well as a fusion protein comprising the same. Nucleic acids encoding eAd and/or polypeptide or the fusion protein thereof, as well as compositions or cells comprising the eAd, polypeptide, fusion protein, or nucleic acid also are provided.

17 Claims, 20 Drawing Sheets

```
           FR1           CDR1        FR2        CDR2          FR3                CDR3      FR4
          (1-26)        (27-38)    (39-55)    (56-65)       (66-104)
      1    10    20      30        40    50    60      70    80    90    100
      ....|....|....|....|....|....|....|....|....|....|....|....|....|....
m36   QVQLVQSGG.GLVQPGGSLRLSCAAS AFDF....SDYE MSWVRQAPGKGLEWIGE INDS...GNT IYNPSLK.SRVTISRDNSKNTLYLQMNTLRAEDTAIYYC AIYGGNSGGEY WGQGTLVTVSS
m36.1 ..........................  T..........  ......E......    ..........  ........N....................................  ...........  ...........
m36.2 ..........I..............    ...........  .......D......   ....R.....  ............................................  ...........  ...........
m36.4 ..........................  ...........  ......E......    ..........  ............................................  ...........  ...........
m36.5 ..........................  ...........  ......E......    ..........  ...........................S................  ...........  ...........
``` wherein the amino acid sequence is as follows:
m36 – SEQ ID NO: 1
m36.1 – SEQ ID NO: 2
m36.2 – SEQ ID NO: 3
m36.4 – SEQ ID NO: 4
m36.5 – SEQ ID NO: 5

(56) References Cited

FOREIGN PATENT DOCUMENTS

| WO | WO 2008/096158 A2 | 8/2008 |
| WO | WO 2009/089295 A2 | 7/2009 |

OTHER PUBLICATIONS

European Patent Office, International Preliminary Report on Patentability in International Patent Application No. PCT/US2011/037439 (Dec. 6, 2012).

Chen et al., "Construction of a large phage-displayed human antibody domain library with a scaffold based on a newly identified highly soluble, stable heavy chain variable domain," *J. Mol. Biol.*, 382(3): 779-789 (2008).

Chen et al., "Human domain antibodies to conserved sterically restricted regions on gp120 as exceptionally potent cross-reactive HIV-1 neutralizers," *Proc. Natl. Acad. Sci. U.S.A.*, 105(44): 17121-17126 (2008).

Chen et al., "Human monoclonal antibodies and engineered antibody domains as HIV-1 entry inhibitors," *Curr. Opin. HIV AIDS*, 4: 112-117 (2009).

Chen et al., "A large human domain antibody library combining heavy and light chain CDR3 diversity," *Mol. Immunol.*, 47(4): 912-921 (2010).

Chen et al., "Bifunctional fusion proteins of the human engineered antibody domain m36 with human soluble CD4 are potent inhibitors of diverse HIV-1 isolates," *Antiviral Res.*, 88(1): 107-115 (2010).

Dey et al., "Neutralization of human immunodeficiency virus type 1 by sCD4-17b, a single-chain chimeric protein, based on sequential interaction of gp120 with CD4 and coreceptor," *J. Virol.*, 77(5): 2859-2865 (2003).

Dimitrov, "Engineered CH2 domains (nanoantibodies)," *mAbs*, 1(1): 26-28 (2009).

European Patent Office, International Search Report in International Patent Application No. PCT/US2011/037439 (Apr. 19, 2012).

Feng et al., "Novel human monoclonal antibodies to insulin-like growth factor (IGF)-II that potently inhibit the IGF receptor type I signal transduction function," Mol. Cancer Ther., 5(1): 114-120 (2006).

Garlick et al., "*Escherichia coli* expression, purification, and biological activity of a truncated soluble CD4," *AIDS Res. Hum. Retroviruses*, 6(4): 465-479 (1990).

Holt et al., "Domain antibodies: proteins for therapy," *TRENDS in Biotechnology*, 21(11): 484-490 (2003).

Huang et al., "Development of single-domain recombinant antibodies to reverse transcriptase domain of human hTERT," *Hybrid. Hybridomics*, 23(4): 244-249 (2004).

Liao et al., "A group M consensus envelope glycoprotein induces antibodies that neutralize subsets of subtype B and C HIV-1 primary viruses," *Virology*, 353(2): 268-282 (2006).

Roben et al., "Recognition properties of a panel of human recombinant Fab fragments to the CD4 binding site of gp120 that show differing abilities to neutralize human immunodeficiency virus type 1," *J. Virol.*, 68(8): 4821-4828 (1994).

Sharma et al., "Protein minimization of the gp120 binding region of human CD4," *Biochemistry*, 44(49): 16192-16202 (2005).

Zhu et al., "Exceptionally potent cross-reactive neutralization of Nipah and Hendra viruses by a human monoclonal antibody," *J. Infect. Dis.*, 197(6): 846-853 (2008).

Zhu et al., "Potent neutralization of Hendra and Nipah viruses by human monoclonal antibodies," *J. Virol.*, 80(2): 891-899 (2006).

\* cited by examiner

FIG. 1

```
              FR1                    CDR1                   FR2              CDR2              FR3                                            CDR3              FR4
           (1-26)                   (27-38)               (39-55)            (56-65)          (66-104)
        1        10        20           30        40        50        60        70        80        90       100
        |         |         |            |         |         |         |         |         |         |         |
m36     .CVQLVQSGG.GLVQPGGSLRLSCAAS APDF....SDYE MSWVRQAPGKGLEWIGF IND3...GNT TYNPSLK.SRVTISRDNSKNTLYLQMNTLRAEDTAIYYC ATYGGNSGGRY WGQGTLVTVSS
m36.1   ........................... .T.......... .E.......E....... ........ ......... N...................................... .............. ...........
m36.2   ........................... ............ .E.......... .E....... ........................................... ............... .............
m36.4   ........................... ............ .E.......... ........ ........................................... ............... .............
m36.5   ........................... ............ .E.......... ........ .................S......................... ............... .............
``` wherein the amino acid sequence is as follows:

m36 – SEQ ID NO: 1 m36.1 – SEQ ID NO: 2 m36.2 – SEQ ID NO: 3 m36.4 – SEQ ID NO: 4 m36.5 – SEQ ID NO: 5

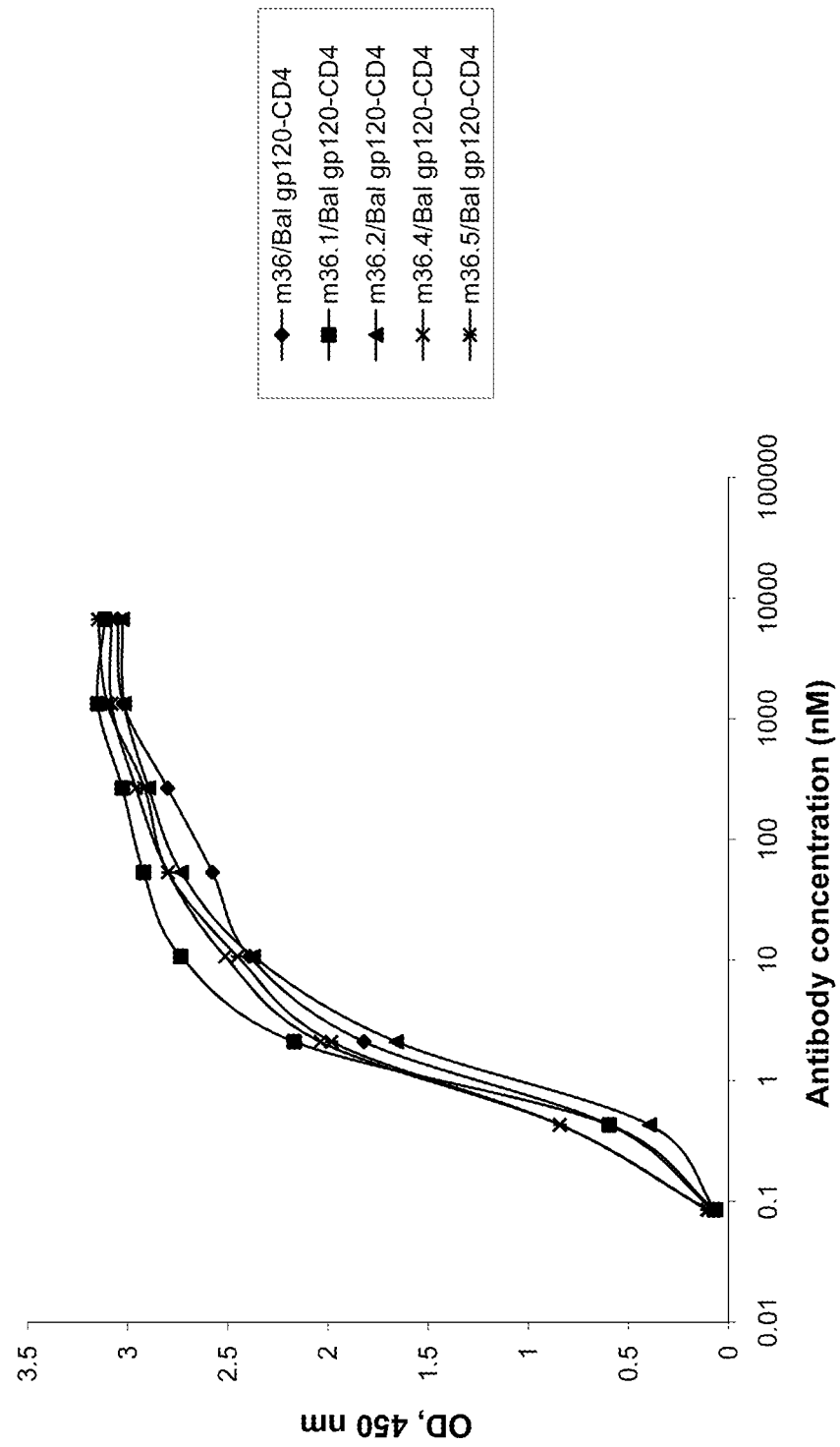

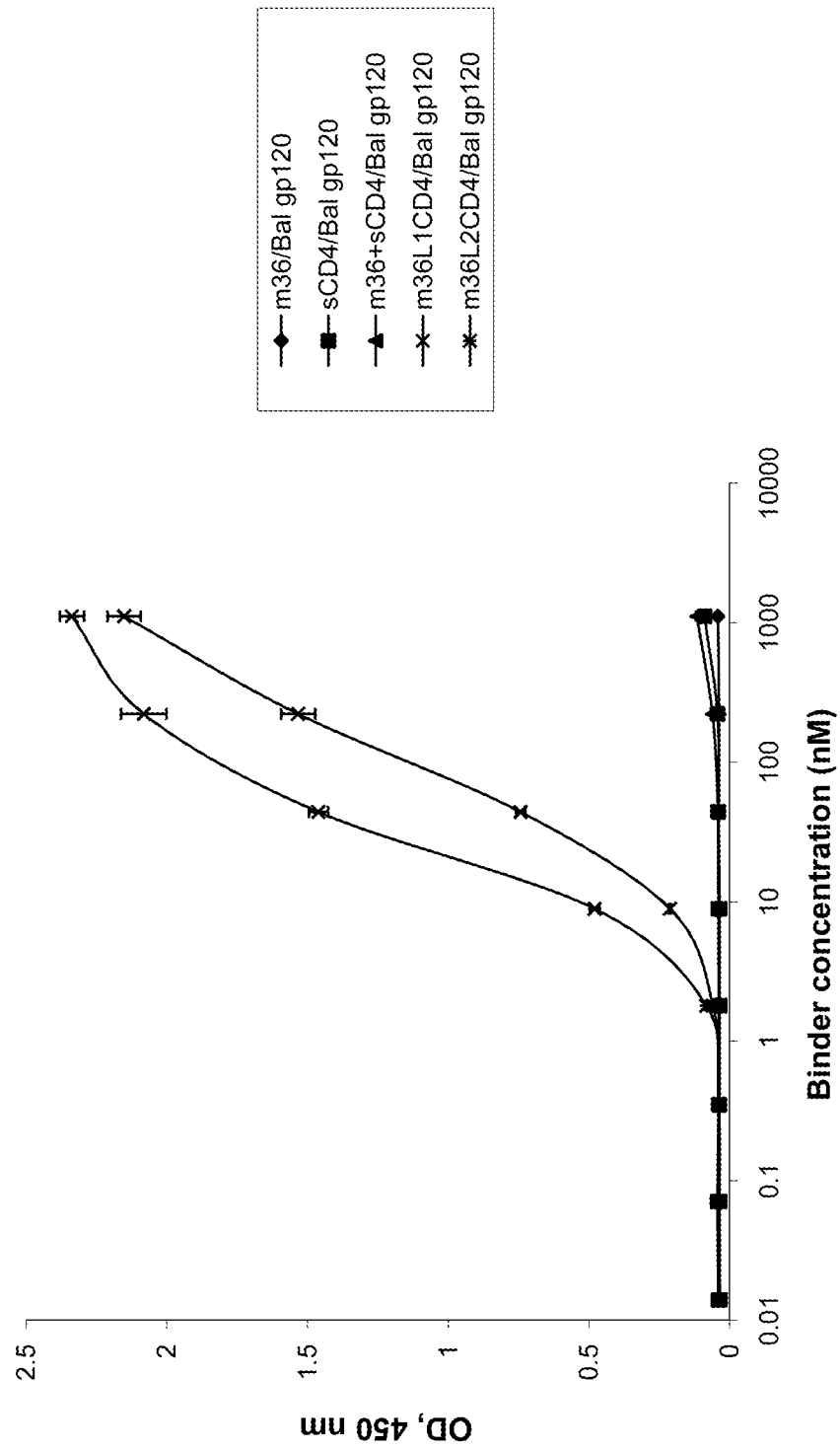

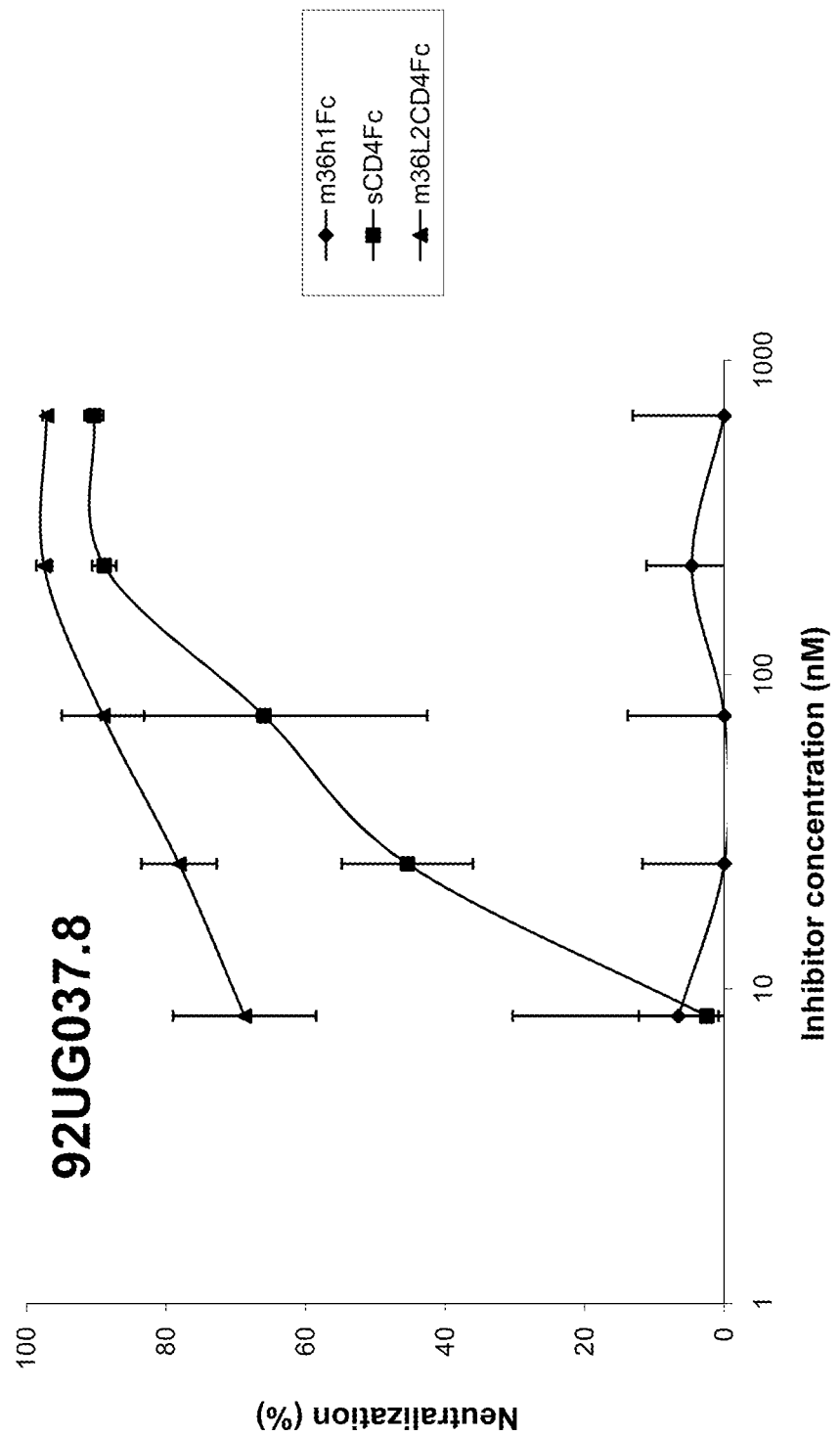

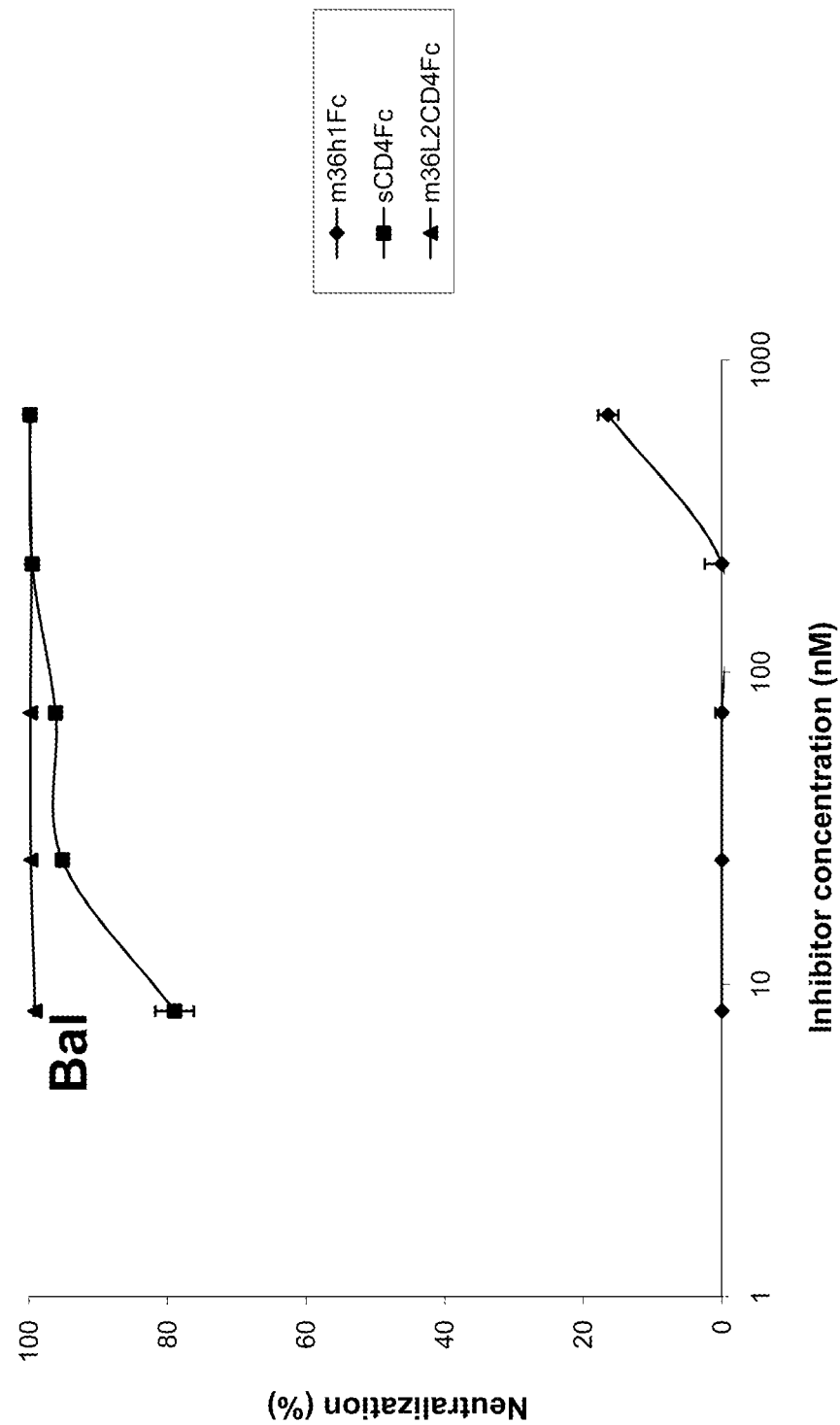

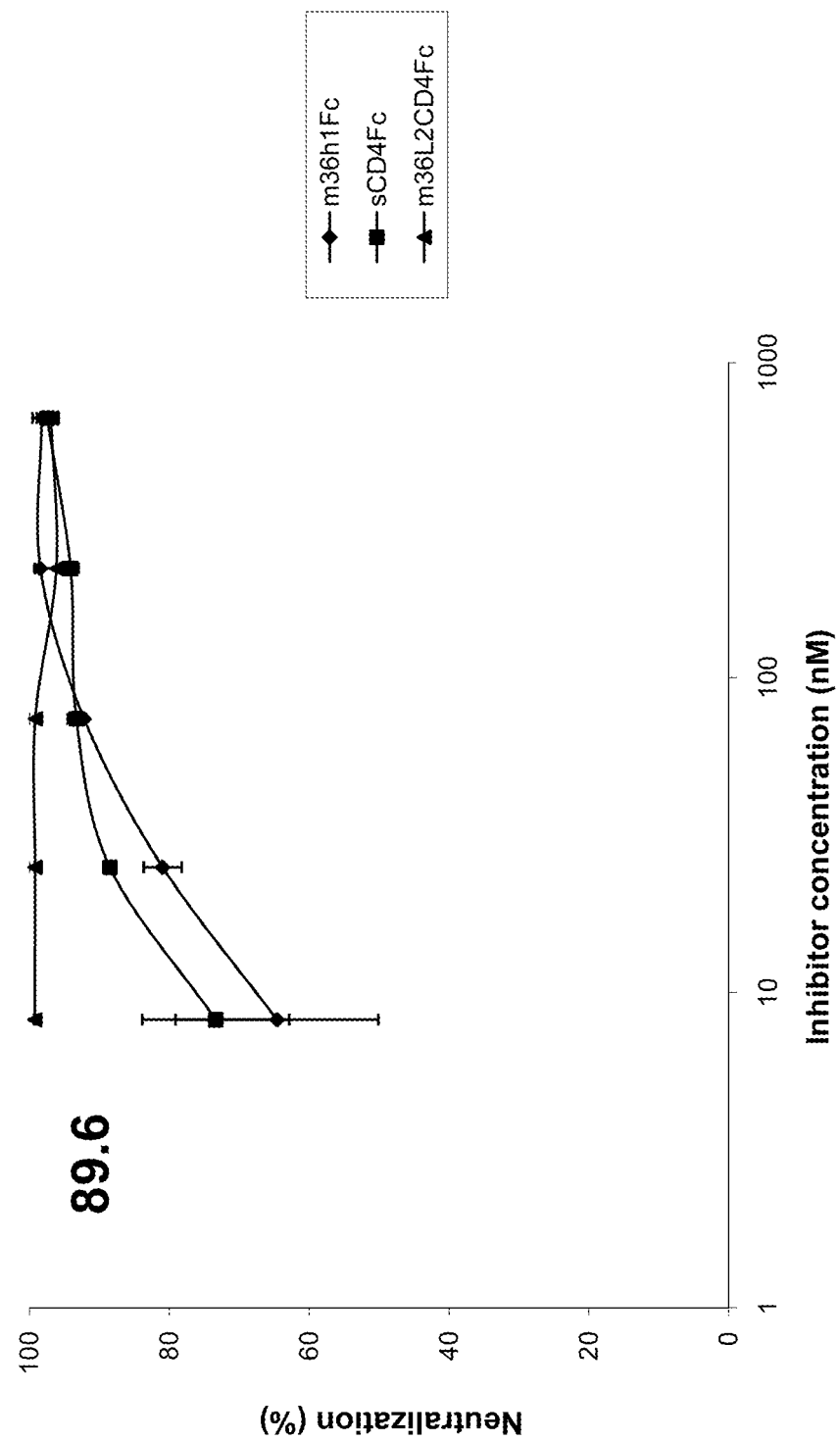

FIG. 7

|      | 1          | 10         | 20         | 30         | 40         | 50         | 60         | 70         | 80         | 90         | 100 | SEQ ID NO: |
|------|------------|------------|------------|------------|------------|------------|------------|------------|------------|------------|-----|------------|
| D1   | KKVVLGKKGD | TVELTCTASQ | KKSIQFHWKN | SNQIKILGNQ | GSFLTKGPSK | LNDRADSRRS | LWDQGNFPLI | IKNLKIEDSD | TYICEVEDQK | EEVQLLVFG  |     | 12 |
| mD1  | .....I.... | .......... | .......... | .......... | .......... | .......... | .......... | .......... | .......... | ..I.L      |     | 13 |
| mD2  | .....Y.... | .......... | ....N..... | .......... | .......... | .......... | .......... | .......... | .......... | ..V.V      |     | 14 |
| mD3  | .....V.... | .......... | .......... | .......... | .......... | .......... | .......... | .......... | .......... | ..I.Q      |     | 15 |
| mD4  | .....E.... | .......... | .......... | .......... | .......... | .......... | .......... | .......... | .......... | ..I.R      |     | 16 |
| mD5  | .....W.... | .......... | .......... | .......... | .......... | .......... | .......... | ......L... | .......... | ..V.L      |     | 17 |
| mD6  | .....Y.... | .......... | .......... | .......... | .......... | .......... | .......... | .......... | .......... | ..I.I      |     | 18 |
| mD7  | .....Y.... | .......... | .......... | .......... | .......... | .......... | .......... | ......Y... | .......... | ..I.T      |     | 19 |
| mD8  | .....Y.QE. | .......... | .......... | ....Q..... | .......... | .......... | .......... | ......L... | .......... | ..I.L      |     | 20 |
| mD9  | .....V.... | .......... | .......... | .......... | .......... | .......V.. | .......... | ......V... | .......... | ..I.L      |     | 21 |
| mD10 | .....Y.... | .......... | .......... | .......... | .......... | .......... | .......... | ......P... | .......... | ..H.I      |     | 22 |
| mD11 | .....I.... | .......... | .......... | ....D..... | .......... | .......... | .......... | ......V... | .......... | ..C.V      |     | 23 |
| mD12 | .....V.... | .......... | .......... | .......... | .......... | .......... | .......S.. | ......L... | .......... | ..I.I      |     | 24 |
| mD13 | .....V.... | .......... | .......... | .......... | .......... | .......... | .......... | ......S... | .......... | ..I.V      |     | 25 |
| mD14 | .....V.... | .......... | ....N..... | .......... | .......... | .......... | .......... | ......P... | .......... | ..T.       |     | 26 |
| mD15 | .....F.... | .......... | .......... | .......... | .......... | .......... | .......... | ......L... | .......... | ..I.T      |     | 27 |
| mD16 | .....Y.... | .......... | .......... | .......... | .......... | .......... | .......... | ......L... | .......... | ..I.L      |     | 28 |
| mD17 | .....V.... | .....A.... | .......... | .......... | .......... | .......... | .......... | ......V... | .......... | ..V.V      |     | 29 |
| mD18 | .....V.... | .......... | .......... | .......... | .......... | .......... | .......... | ......E... | ...G...... | ..V.V      |     | 30 |
| mD19 | .....TA... | .......... | .......... | .......... | .......... | .......... | .......... | ......L... | .......... | ..I.Q      |     | 31 |

Hydrophobic residues (%): 89         58         89   68

US 8,911,728 B2

HIGH-AFFINITY FULLY FUNCTIONAL SOLUBLE SINGLE-DOMAIN HUMAN CD4, ANTIBODIES, AND RELATED FUSION PROTEINS

CROSS-REFERENCE TO RELATED APPLICATIONS

This patent application is a U.S. National Phase of International Patent Application No. PCT/US2011/037439, filed May 20, 2011, which claims the benefit of U.S. Provisional Patent Application Nos. 61/347,088, filed May 21, 2010, and 61/467,570, filed Mar. 25, 2011, which are incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 144,012 Byte ASCII (Text) file named "711282_ST25.TXT," created on Nov. 7, 2012.

BACKGROUND OF THE INVENTION

HIV-1 entry is initiated by binding of the viral envelope glycoprotein (Env) gp120 to cellular receptor CD4. The interaction results in extensive conformational rearrangements of gp120 and subsequently gp41 after engagement of a coreceptor (either CCR5 or CXCR4). The structural rearrangements of Envs and the interplay between Envs and the cellular receptor and co-receptor bring viral membrane toward target cell membrane, and eventually cause membrane fusion and viral entry. CD4 and envelope glycoprotein gp120 are, therefore, attractive molecular targets for HIV treatment.

Recombinant solubly expressed CD4 (sCD4) containing either all four (T4) or the first two extracellular domains (D1D2) can be used to inhibit HIV-1 entry. Similarly, anti-gp120 antibodies can be used to inhibit HIV infection. Still, there remains a need for new and effective anti-HIV therapies.

BRIEF SUMMARY OF THE INVENTION

The invention provides an engineered antibody domain (eAd) comprising SEQ ID NO: 139, wherein $x^1$-$x^7$ can be any amino acid, provided that the eAd does not comprise SEQ ID NO: 1.

The invention also provides a polypeptide comprising a single-domain CD4 comprising SEQ ID NO: 11, wherein $x^1$-$x^{14}$ can be any amino acid, provided that the single-domain CD4 does not comprise SEQ ID NO: 12.

Additionally, the invention provides a fusion protein comprising (i) an eAd comprising SEQ ID NO: 139 and (ii) one or more fusion partners, wherein the one or more fusion partners optionally is joined to the eAd via a linker.

In another aspect, the invention provides a fusion protein comprising (i) a single-domain CD4 comprising SEQ ID NO: 11, and (ii) one or more fusion partners, wherein the one or more fusion partners optionally is joined to the single-domain CD4 via a linker.

Nucleic acids encoding the eAd, single-domain CD4, or fusion protein, as well as compositions or cells comprising the eAd, single-domain CD4, fusion proteins, or nucleic acids, also are provided.

The invention further provides a method of inhibiting an HIV infection in a cell or a host comprising administering the eAd, single-domain CD4, or fusion protein to the cell or host, such that the HIV infection is inhibited.

The invention also provides a method of inhibiting an HIV infection in a cell or a host comprising administering the eAd, single-domain CD4, or fusion protein to the cell or host, such that the HIV infection is inhibited.

BRIEF DESCRIPTION OF THE SEVERAL VIEWS OF THE DRAWING

FIG. 1 is an amino acid sequence alignment of m36 (SEQ ID NO: 1), m36.1 (SEQ ID NO: 2), m36.2 (SEQ ID NO: 3), m36.4 (SEQ ID NO: 4), and m36.5 (SEQ ID NO: 5), wherein FR1 refers to Framework Region 1; CDR1 refers to Complementarity Determining Region 1; FR2 refers to Framework Region 2; CDR2 refers to Complementarity Determining Region 2; FR3 refers to Framework Region 3; CDR3 refers to Complementarity Determining Region 3; and FR4 refers to Framework Region 4. The sequences are numbered and the antibody FRs and CDRs are indicated according to the ImMunoGeneTics (IMGT) numbering system. The residues in the m36.1, m36.2, m36.4, and m36.5 amino acid sequences that are identical to the m36 amino acid sequence are indicated by dots.

FIGS. 2A-D are graphs showing the results of ELISA binding of m36, m36.1, m36.2, m36.4, and m36.5 to gp120$_{Bal}$ (FIG. 2A), gp140$_{JRFL}$ (FIG. 2B), gp140$_{SC}$ (FIG. 2C), and gp120$_{Bal}$-CD4 (FIG. 2D). Antibody concentration (nM) is on the x-axis and Optical Density (OD) at 450 nm is on y-axis for each of FIGS. 2A-D. Antibody specificity was determined using an unrelated antigen, bovine serum albumin (BSA).

FIG. 4A is a schematic representation of fusion protein architecture. FIG. 4B is the reducing SDS-PAGE of m36, m36.4, and fusion proteins thereof.

FIGS. 5A-D illustrate a comparative analysis of ELISA binding. FIG. 5A depicts a comparison of m36-sCD4 fusion proteins with linkers of different lengths to m36 or sCD4 alone and unlinked m36 plus sCD4 for binding to gp120$_{Bal}$. Binder concentration (nM) is on the x-axis and Optical Density (OD) at 450 is on the y-axis. FIG. 5B depicts the binding of m36L2CD4 and m36L2CD4Fc to gp120$_{Bal}$. Antibody concentration (nM) is on the x-axis and Optical Density (OD) at 450 nm is on the y-axis. FIG. 5C depicts the binding of m36L2CD4Fc, m36h1Fc, and sCD4Fc to gp120$_{Bal}$. Antibody concentration (nM) is on the x-axis and Optical Density (OD) at 450 nm is on the y-axis. FIG. 5D depicts the binding of the fusion proteins of m36 and m36.4 to gp120$_{Bal}$. Antibody concentration (nM) is on the x-axis and Optical Density (OD) at 450 nm is on the y-axis.

FIG. 7 is an amino acid sequence comparison between human single-domain CD4 (D1) and mutants thereof.

DETAILED DESCRIPTION OF THE INVENTION

Figure 2A:
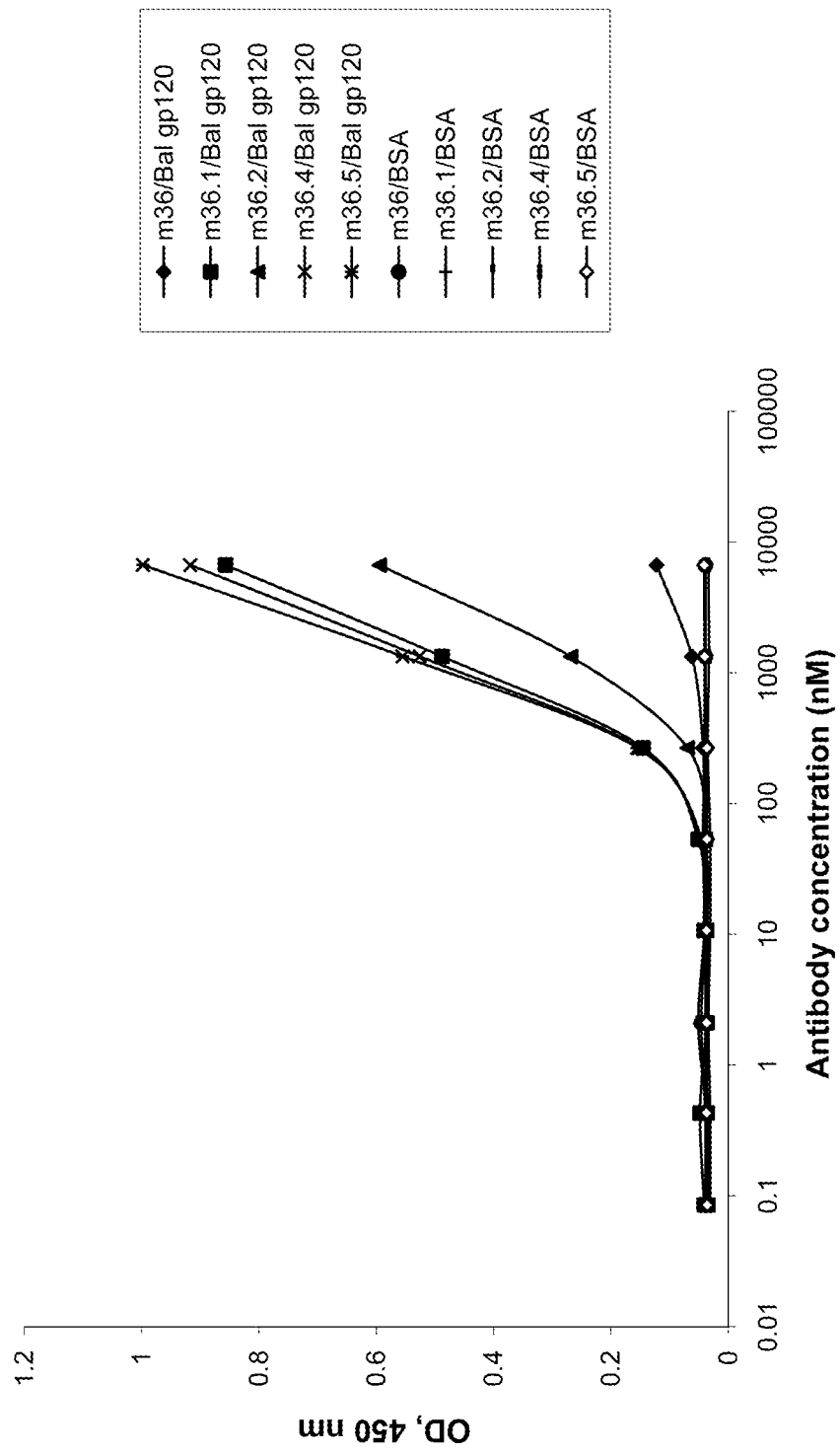

The invention provides new engineered antibody domains (eAds), a single-domain CD4 (referred to herein as D1 or mD1), as well as fusion proteins comprising one or more eAds and/or single-domain CD4.

Engineered Antibody Domains (eAds)

An eAd is provided herein, which comprises, consists essentially of, or consists of the amino acid sequence of SEQ ID NO: 139:

```
                                       (SEQ ID NO: 139)
QVQLVQSGGGLx¹QPGGSLRLSCAASx²FDFSDYEMSWVRx³x⁴PGK

GLEWIGEINDx⁵GNTIYNPSLKx⁶RVTISRDNSKNTLYLQMNTLx⁷AE

DTAIYYCAIYGGNSGGEYWGQGTLVTVSS
``` wherein each of $x^1$-$x^7$ can be any amino acid, provided that the eAd does not comprise the amino acid sequence of SEQ ID NO: 1. Desirably, one or more of $x^1$-$x^7$ (two or more, three or more, four or more, five or more, six or more, or all seven of $x^1$-$x^7$) is selected as follows:

$x^1$ can be V or I;
$x^2$ can be A or T;
$x^3$ can be Q or E;
$x^4$ can be A or D;
$x^5$ can be S or R;
$x^6$ can be S or N;
$x^7$ can be R or S.

By way of further illustration, the eAds can comprise, consist essentially of, or consist of SEQ ID NO: 2, SEQ ID NO: 3, SEQ ID NO: 4, or SEQ ID NO: 5, also referenced herein as the m36.1, m36.2, m36.4, or m36.5 antibodies, respectively. According to preferred embodiments, the eAd targets a highly conserved hidden CD4-inducible (CD4i) epitope on HIV-1 gp120, and/or can neutralize HIV-1 primary isolates from multiple different clades.

The eAds can be provided alone, or as part of a fusion protein comprising the eAd and one or more fusion partners. The fusion partner can be any suitable moiety that does not substantially inhibit the antibody's ability to bind its target. Desirably, the fusion partner enhances the stability and/or potency of the fusion protein as compared to the stability or potency of the eAd in the absence of the fusion partner. For instance, the fusion partner can be a naturally occurring protein or fragment thereof that resists degradation or removal by endogenous mechanisms in vivo, thereby increasing the half-life of the fusion protein as compared to the eAd in the absence of the fusion protein. Fusion partners and fusion proteins are discussed further in a subsequent section.

Single-Domain CD4 (D1)

The invention also provides a single-domain CD4. According to one aspect of the invention, the single-domain CD4 comprises, consists essentially of, or consists of the amino acid sequence of SEQ ID NO: 11:

```
                                        (SEQ ID NO: 11)
KKVVx¹x²x³x⁴GDTVELx⁵CTASQKKx⁶IQFx⁷WKx⁸SNQIKILGNQGSF

LTKGPSKLNDRx⁹DSRRSLWDQGx¹⁰FPLIIKNLKx¹¹EDSx¹²TYICEVE

DQKEEVQLx¹³Vx¹⁴G
``` wherein "x" can be any amino acid, provided the single-domain CD4 does not comprise SEQ ID NO: 12. Desirably, one or more of $x^1$-$x^{14}$ (two or more, three or more, four or more, five or more, six or more, seven or more, eight or more, nine or more, ten or more, eleven or more, twelve or more, thirteen or more, or all fourteen of $x^1$-$x^{14}$) are selected as follows:

$x^1$ (position 5 of SEQ ID NO: 11) is I, Y, V, E, W, F, or T; preferably, a hydrophobic residue;
$x^2$ (position 6 of SEQ ID NO: 11) is G or A;
$x^3$ (position 7 of SEQ ID NO: 11) is K or Q;
$x^4$ (position 8 of SEQ ID NO: 11) is K or E;
$x^5$ (position 15 of SEQ ID NO: 11) is T or A;
$x^6$ (position 23 of SEQ ID NO: 11) is S or N,
$x^7$ (position 27 of SEQ ID NO: 11) is H or Q;
$x^8$ (position 30 of SEQ ID NO: 11) is N or D;
$x^9$ (position 55 of SEQ ID NO: 11) is A or V;
$x^{10}$ (position 66 of SEQ ID NO: 11) is N or S;
$x^{11}$ (position 76 of SEQ ID NO: 11) is I, P, L, Y, V, S, or E;
$x^{12}$ (position 80 of SEQ ID NO: 11) is D or G;
$x^{13}$ (position 96 of SEQ ID NO: 11) is L, I, V, H, or C; preferably, a hydrophobic residue.
$x^{14}$ (position 98 of SEQ ID NO: 11) is F, L, V, Q, R, I, or T.

According to another aspect of the invention, the single-domain CD4 comprises, consists essentially of, or consists of the amino acid sequence of SEQ ID NO: 12 modified with up to 20 (e.g., 0, 1, 2, 3, 4, 5, 6, 7, 8, 9, 10, 11, 12, 13, 14, 15, 16, 17, 18, 19, or 20) additions, deletions, substitutions, or insertions. Preferably, the sequence of SEQ ID NO: 12 comprises up to 10 additions, deletions, substitutions, or insertions.

Although the mutations relative to SEQ ID NO: 12 can be in any suitable position as long the above-described activities are maintained, preferably, the mutations are in hydrophobic residues, such as residues 5L, 76I, 96L, and 98F of SEQ ID NO: 12. For example, the leucine at residue 5 can be substituted with isoleucine, tyrosine, valine, glutamic acid, tryptophan, phenylalanine, or threonine, and preferably is substituted with a hydrophobic residue. The isoleucine at residue 76 can be substituted with proline, leucine, tyrosine, valine, serine, or glutamic acid. The leucine at residue 96 can be substituted with isoleucine, valine, histidine, or cysteine, and preferably is substituted with a hydrophobic residue. The phenylalanine at residue 98 can be substituted with leucine, valine, glutamine, arginine, isoleucine, or threonine.

Additionally, or alternatively, other residues within SEQ ID NO: 12 can be mutated. For example, the glycine at residue 6 can be substituted with alanine. The lysine at residue 7 can be substituted with glutamine. The lysine at residue 8 can be substituted with glutamic acid. The threonine at residue 15 can be substituted with alanine. The serine at residue 23 can be substituted with asparagine. The histidine at residue 27 can be substituted glutamine. The asparagine at residue 30 can be substituted with aspartic acid. The alanine at position 55 can be substituted with valine. The asparagine at position 66 can be substituted with serine. The aspartic acid at position 80 can be substituted with glycine.

By way of further illustration, single-domain CD4 polypeptides in accordance with the invention can comprise, consist essentially of or consist of the amino acid sequence of any of SEQ ID NOs: 13-31. Particularly preferred embodiments include those polypeptides comprising, consisting essentially of, or consisting of SEQ ID NO: 13 or SEQ ID NO: 14.

Preferred embodiments of the single-domain CD4 polypeptide retain at least the same degree binding affinity and specificity of full-length CD4, and maintain other functions, such as the ability to induce conformational changes in HIV-1 gp120. Due to decreased molecular size, the single-domain CD4 is believed to have excellent biological properties including improved binding kinetics, soluble expression in *E. coli*, higher solubility, stability and specificity, minimization of immunogenicity in animals, and better penetration into tissues, such as the densely packed lymphoid environments (e.g., spleen, lymph node and gut) where HIV-1 mostly replicates and spreads.

The inventive single-domain CD4 can be provided alone, or as part of a fusion protein comprising the single-domain CD4 and one or more fusion partners. The fusion partner can be any suitable moiety that does not substantially inhibit the single-domain CD4's ability to bind its target. Desirably, the fusion partner enhances the stability and/or potency of the single-domain CD4 as compared to the stability or potency of the single-domain CD4 in the absence of the fusion partner. For instance, the fusion partner can be a naturally occurring protein or fragment thereof that resists degradation or removal by endogenous mechanisms in vivo, thereby increasing the half-life of the fusion protein as compared to the single-domain CD4 in the absence of the fusion protein. Fusion partners and fusion proteins are discussed further in subsequent sections.

Fusion Partners

Examples of suitable fusion partners for the single-domain CD4 and/or eAd include: (a) proteins from the extracellular matrix, such as collagen, laminin, integrin, and fibronectin; (b) proteins found in blood, such as serum albumin, serum albumin-binding peptide (SAbp), fibrinogen A, fibrinogen B, serum amyloid protein A, heptaglobin, protein, ubiquitin, uteroglobulin, β-2 microglobulin, plasminogen, lysozyme, cystatin C, α-1-antitrypsin, and pancreatic kypsin inhibitor; (c) immune serum proteins, such as IgE, IgG, IgM, and their fragments (e.g., Fc); (d) transport proteins, such as retinol binding protein; (e) defensins, such as β-defensin 1, neutrophil defensins 1, 2 and 3; (f) proteins found at the blood brain barrier or in neural tissues, such as melanocortin receptor, myelin, ascorbate transporter; (g) transferrin receptor specific ligand-neuropharmaceutical agent fusion proteins, brain capillary endothelial cell receptor, transferrin, transferrin receptor, insulin, insulin-like growth factor 1 (IGF 1) receptor, insulin-like growth factor 2 (IGF 2) receptor, insulin receptor; (h) proteins localized to the kidney, such as polycystin, type IV collagen, organic anion transporter K1, Heymann's antigen; (i) proteins localized to the liver, such as alcohol dehydrogenase, G250; (j) blood coagulation factor X; (k) α-1 antitrypsin; (l) HNF 1α; (m) proteins localized to the lung, such as secretory component; (n) proteins localized to the heart, such as HSP 27; (o) proteins localized to the skin, such as keratin; (p) bone specific proteins, such as bone morphogenic proteins (BMPs), for example, BMP-2, -4, -5, -6, -7 (also referred to as osteogenic protein (OP-I) and -8 (OP-2); (q) tumor specific proteins, such as human trophoblast antigen, herceptin receptor, estrogen receptor, cathepsins, for example, cathepsin B (found in liver and spleen); (r) disease-specific proteins, such as antigens expressed only on activated T-cells: including LAG-3 (lymphocyte activation gene); osteoprotegerin ligand (OPGL); OX40; metalloproteases, including CG6512 *Drosophila*, human paraplegin, human FtsH, human AFG3L2, murine ftsH; angiogenic growth factors, including acidic fibroblast growth factor (FGF-I), basic fibroblast growth factor (FGF-2), Vascular endothelial growth factor/vascular permeability factor (VEGF/VPF), transforming growth factor-α (TGF-α), tumor necrosis factor-alpha (TNF-α), angiogenin, interleukin-3 (IL-3), interleukin-8 (IL-8), platelet derived endothelial growth factor (PD-ECGF), placental growth factor (PIGF), midkine platelet-derived growth factor-BB (PDGF), fractalkine; (s) stress proteins (heat shock proteins); (t) proteins involved in Fc transport; and (u) CD4 or a fragment or mimic thereof.

In one embodiment, the fusion partner is an immunoglobulin Fc region or portion thereof (e.g., the CH2 or CH3 region), especially the Fc region of a human immunoglobulin, such as a human IgG1 Fc region. Examples of an Fc region or portion thereof for use in the invention include, but are not limited to, the amino acid sequence of SEQ ID NO: 41 and SEQ ID NO: 42.

In an alternative embodiment, the fusion partner is an immunoglobulin heavy chain constant region (CH) and/or or light chain constant region (CL), such as human IgG1 heavy chain constant region or human IgG1 light chain constant region. Examples of IgG1 heavy and light chain constant regions for use in the invention are the amino acid sequence of SEQ ID NO: 137 and SEQ ID NO: 138, respectively.

In another embodiment, the fusion partner is an HIV (e.g., HIV-1 or HIV-2) envelope glycoprotein. Examples of the HIV envelope glycoprotein include gp120 and gp140. Preferably, the HIV envelope glycoprotein is HIV-1 gp120. An example of a gp120 is SEQ ID NO: 43.

The fusion partner also can be an antibody or antibody fragment (e.g., Fab, scFv, eAd, etc.). For instance, the antibody can be an eAd comprising SEQ ID NO: 139, or any of SEQ ID NO: 1, SEQ ID NO: 2, SEQ ID NO: 3, SEQ ID NO: 4, or SEQ ID NO: 5, also referenced herein as the m36, m36.1, m36.2, m36.4, or m36.5 antibodies, respectively.

The fusion partner also can be selected from CD4 or a fragment or mimic thereof, such as soluble CD4 (sCD4), which may increase the effectiveness of the binding of the antibody with its cognate HIV epitope, e.g., a CD4i epitope. CD4 mimics are known in the art and can be found described, for example, in U.S. Application Publication Nos. 2006/0073576 and 2008/0096187. Suitable sCD4 polypeptides are known in the art and are available commercially from, for example, ImmunoDiagnostics, Inc. (Woburn, Mass.) and Protein Sciences Corp. (Meriden, Conn.). Examples of CD4 and fragments or mimics thereof for use in the invention include SEQ ID NO: 35 (soluble cD4) and SEQ ID NO: 32 (polypeptide comprising domains 1 and 2 of CD4). Preferably, the CD4 is a single-domain CD4 comprising one of SEQ ID NOs: 11-31.

Additional fusion partners for use in connection herewith are described in WO 2009/089295.

Fusion Proteins

The invention provides a fusion protein comprising (i) an eAd comprising SEQ ID NO: 139 and (ii) one or more fusion partners. The one or more fusion partners can be any described herein (e.g., two, three, four, five, or more fusion partners). For instance, the fusion protein can comprise, as fusion partners to the eAd, CD4 or a fragment or mimic thereof, such as sCD4 or single-domain CD4, and a stability-enhancing fusion partner, such as an immunoglobulin Fc region (e.g., human IgG1 Fc) or portion thereof (e.g., CH3).

In another aspect, the invention provides a fusion protein comprising (i) a single-domain CD4 comprising SEQ ID NO: 11, and (ii) one or more fusion partners. The one or more fusion partners can be any described herein (e.g., two, three, four, five, or more fusion partners). For instance, the fusion protein could comprise, as fusion partners to the single-domain CD4, an eAd (e.g., the m36, m36.1, m36.2, m36.4, or m36.5 antibodies of SEQ ID NOs: 1-5, respectively), and/or a stability-enhancing fusion partner, such as an immunoglobulin Fc region (e.g., human IgG1 Fc) or portion thereof (e.g., CH3).

The one or more fusion partners can be joined to the eAd or single-domain CD4 via a linker (i.e., a flexible molecular connection, such as a flexible polypeptide chain). The linker can be any suitable linker of any length, but is preferably at least about 15 (e.g., at least about 20, at least about 25, at least about 30, at least about 35, at least about 40, at least about 45, at least about 50, or ranges thereof) amino acids in length. In one embodiment, the linker is an amino acid sequence that is naturally present in immunoglobulin molecules of the host, such that the presence of the linker would not result in an immune response against the linker sequence by the mammal. For example, the linker can comprise one or more (e.g., two or more, three or more, four or more, five or more, six or more, seven or more, eight or more, nine or more, or ten or more) $G_4S$ motifs. Examples of suitable linkers include, but are not limited to, the linkers of SEQ ID NO: 38 (linker 1; L1), SEQ ID NO: 39 (linker 2; L2), SEQ ID NO: 40 (linker 3; L3), SEQ ID NO: 41 (linker 6; L6), and SEQ ID NO: 42 (linker 9; L9).

By way of further illustration, non-limiting examples of fusion proteins according to the invention can have the following configuration: (first fusion partner)-(optional first linker)-(single-domain CD4)-(optional second linker)-(optional second fusion partner). More specific illustrative examples include the following: gp120-linker-D1 (SEQ ID NO: 57), m36.4-linker-D1 (SEQ ID NO: 61, SEQ ID NO: 63, and SEQ ID NO: 65), D1-linker-CH3 (SEQ ID NO: 67, SEQ ID NO: 69, and SEQ ID NO: 71), m36.4-linker-D1-linker-CH3 (SEQ ID NO: 73), and m36.4-linker-D1-Fc (SEQ ID NO: 75).

Alternatively, the fusion proteins can have the following configuration: (antibody)-(linker)-(first fusion partner)-(optional second linker)-(optional second fusion partner). More specific illustrative examples include the following: m36.4-L2-CD4 (SEQ ID NO: 49) and m36.4-L2-CD4-Fc (SEQ ID NO: 53).

In another aspect, the invention provides a fusion protein comprising the m36 eAd (SEQ ID NO: 1), CD4 or a fragment or mimic thereof, such as sCD4 or a single-domain CD4, and an immunoglobulin or portion thereof (e.g., an Fc region, such as human IgG1 Fc region), wherein fusion partners optionally can be joined to each other or m36 via a linker. A particular embodiment of this fusion protein comprises SEQ ID NO: 51, which has the following configuration: m36-linker-CD4-Fc.

The invention also provides a fusion protein comprising:
A-(optional linker)-C-(optional linker)-B or
B-(optional linker)-D-(optional linker)-E-(optional liner)-B
wherein A denotes an antibody or antibody fragment (e.g., Fab, scFv, eAd, etc.), B denotes CD4 or a mimic or fragment thereof (e.g., single-domain CD4; D1), C denotes an immunoglobulin light chain constant region (e.g., human IgG1 kappa light chain constant region), D denotes an immunoglobulin heavy chain constant region (e.g., human IgG1 heavy chain constant region), and E denotes an Fc region (e.g., the Fc region from human IgG1). Specific examples include D1-linker-human IgG1 heavy chain constant region-linker-D1 (SEQ ID NO: 134) and m36.4-linker-human IgG1 light chain constant region-linker-D1 (SEQ ID NO: 136).

Figure 8:
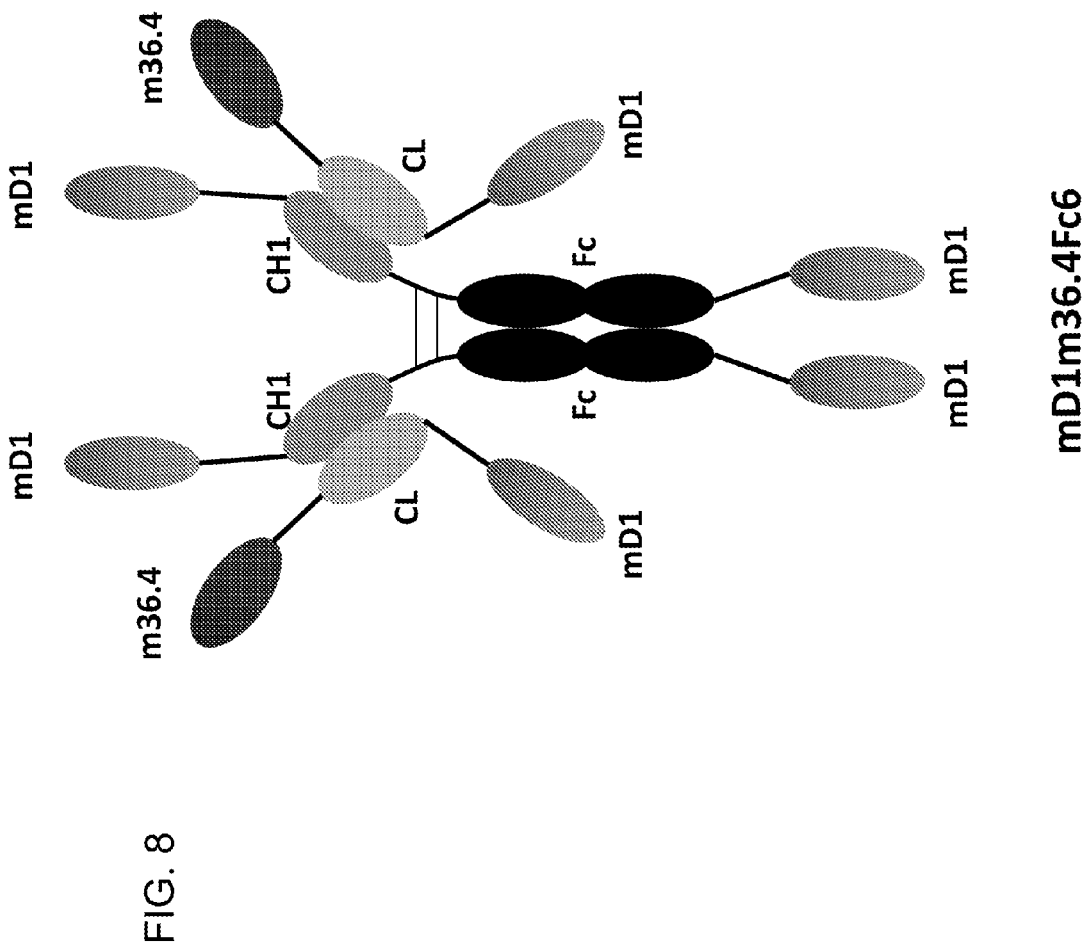
FIG. 8 is a depiction of the structure of mD1m36.4Fc6, which is described in Example 11.
Figure 9:
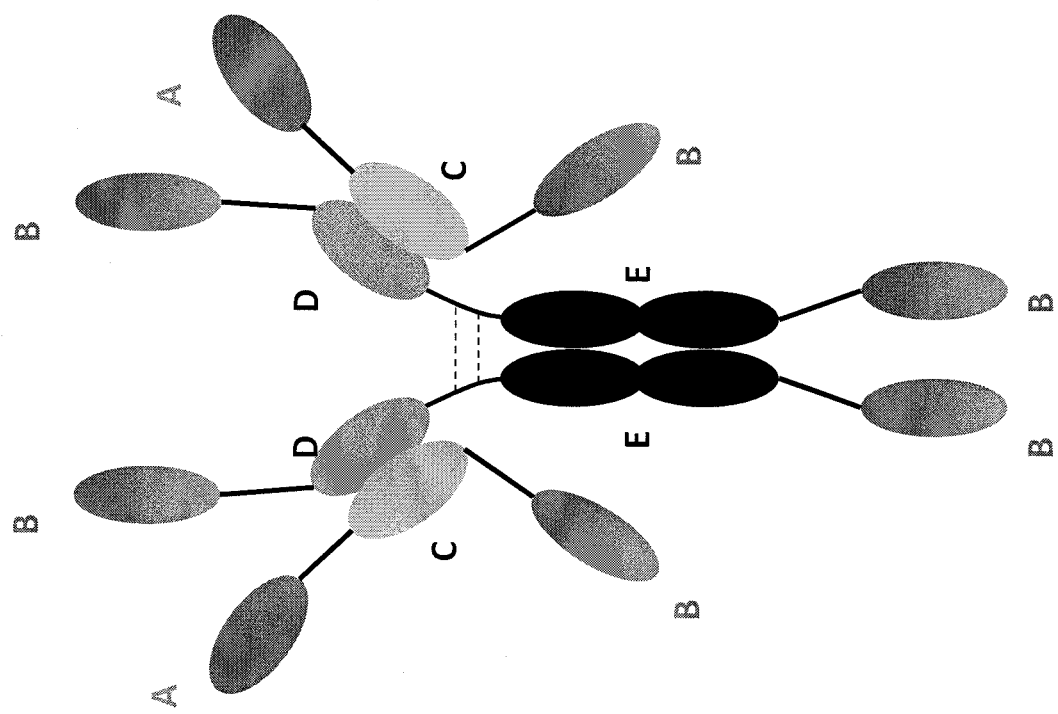
FIG. 9 is a depiction of a construct containing multiple fusion proteins, wherein A denotes an antibody or antibody fragment, B denotes CD4 or a mimic or fragment thereof, C denotes a light chain constant region, D denotes a heavy chain constant region, and E denotes an Fc region. Straight lines connecting the regions denote linker sequences. The dashed line represents optional bonds.

Two or more of the fusion proteins can be conjugated or otherwise joined in a larger construct. For instance, two fusion proteins of Formula (I) above and two fusion proteins of Formula (II) above can be assembled into a single construct, as depicted in FIGS. 8 and 9. The individual fusion proteins can be joined in the manner typical of IgG type constructs, such as by disulfide bridges between the constant heavy and constant light regions and between the Fc regions. Two or more fusion proteins joined as a single construct desirably can provide a multivalent (bivalent, tetravalent, or even octavalent) molecule.

Additional Aspects

The single-domain CD4, eAd, and fusion protein can be PEGylated, or coupled to polymers of similar structure, function and purpose, to confer enhanced stability and half-life. PEGylation can provide increased half-life and resistance to degradation without a loss in activity (e.g., binding affinity) relative to non-PEGylated (e.g., antibody) polypeptides. Since PEGylation may not be advantageous with respect to some targets, in particular, those epitopes which are sterically-obstructed, the single-domain CD4, eAd, or fusion protein should be minimally PEGylated so as not to negatively impact the accessibility to the size-restricted antigen. The single-domain CD4, eAd, or fusion protein can be coupled to PEG or PEG-like polymers by any suitable means known in the art. Suitable PEG or PEG-like moieties can be synthetic or naturally occurring and include, but are not limited to, straight or branched chain polyalkylene, polyalkenylene or polyoxyalkylene polymers, or a branched or unbranched polysaccharide, such as a homo- or heteropolysaccharide. Preferred examples of synthetic polymers include straight or branched chain poly(ethylene glycol) (PEG), poly(propylene glycol), or poly(vinyl alcohol) and derivatives or substituted forms thereof. Substituted polymers for linkage to the domain antibodies also include substituted PEG, including methoxy (polyethylene glycol). Naturally occurring polymer moieties which can be used in addition to or in place of PEG include, for example, lactose, amylose, dextran, or glycogen, as well as derivatives thereof.

The single-domain CD4, eAd, or fusion protein can be multimerized, as for example, hetero- or homodimers, hetero- or homotrimers, hetero- or homotetramers, or higher order hetero- or homomultimers. Multimerization can increase the strength of antigen binding, wherein the strength of binding is related to the sum of the binding affinities of the multiple binding sites. In particular, cysteine residue(s) can be introduced in the amino acid sequence of the single-domain CD4, eAd, or fusion proteins, thereby allowing interchain disulfide bond formation in a multimerized form. The homodimeric or heterodimeric (or multimeric) fusion proteins can include combinations of the same or different fusion partners (e.g., eAds), such that more than one epitope can be targeted at a time by the same construct. Such epitopes can be proximally located in the target (e.g., on the HIV target) such that the binding of one epitope facilitates the binding of the multimeric binding molecule of the invention to the second or more epitopes. The epitopes targeted by multimeric antibodies also can be distally situated.

Conjugates comprising the single-domain CD4, eAd, or fusion protein of the invention conjugated to cytotoxic agents, such as chemotherapeutic agents, toxin (e.g., an enzymatically active toxin of bacterial, fungal, plant or animal origin, or fragments thereof), radioactive isotopes (i.e., a radioconjugate), or antiviral compounds (e.g., anti-HIV compounds)

also are encompassed by the invention. Alternatively, the single-domain CD4, eAd, or fusion protein can be co-administered with the cytotoxic agents, antiviral compounds, and the like.

Methods for conjugating the single-domain CD4, eAd, or fusion protein to the cytotoxic agents, chemotherapeutic agents, toxins, antibacterial compounds, and antiviral compounds, and the like are well known in the art. For example, conjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Detectable agents, such as fluorescent compounds, also can be added to the single-domain CD4, eAd, or fusion protein. Exemplary fluorescent detectable agents include fluorescein, fluorescein isothiocyanate, rhodamine, 5-dimethylamine-1-napthalenesulfonyl chloride, phycoerythrin and the like. The single-domain CD4, eAd, or fusion protein also can be derivatized with detectable enzymes, such as alkaline phosphatase, horseradish peroxidase, glucose oxidase and the like. When the single-domain CD4, eAd, or fusion protein construct is derivatized with a detectable enzyme, it is detected by adding additional reagents that the enzyme uses to produce a detectable reaction product. The single-domain CD4, eAd, or fusion protein construct also can be derivatized with biotin, and detected through indirect measurement of avidin or streptavidin binding.

Additional peptide sequences can be added to the fusion protein, which act to promote stability, purification, and/or detection. For example, a reporter peptide portion (e.g., green fluorescent protein (GFP), β-galactosidase, or a detectable domain thereof) can be used. Purification-facilitating peptide sequences include those derived or obtained from maltose binding protein (MBP), glutathione-S-transferase (GST), or thioredoxin (TRX). The single-domain CD4, eAd, or fusion protein also or alternatively can be tagged with an epitope which can be antibody purified (e.g., the Flag epitope, which is commercially available from Kodak (New Haven, Conn.)), a hexa-histidine peptide, such as the tag provided in a pQE vector available from QIAGEN, Inc. (Chatsworth, Calif.), or an HA tag (as described in, e.g., Wilson et al., *Cell,* 37, 767 (1984)).

Constructs comprising two or more (e.g., two, three, four, five, six, seven, eight, nine, ten, or more) of the inventive fusion proteins also are encompassed by the invention. Preferably, the construct comprises four of the inventive fusion proteins.

In one embodiment, the fusion proteins is assembled (e.g., self-assembled) to form the construct depicted in FIG. 9, wherein A denotes an antibody or antibody fragment (e.g., Fab, scFv, eAd, etc.), B denotes CD4 or a mimic or fragment thereof (e.g., single-domain CD4), C denotes an immunoglobulin light chain constant region (e.g., human IgG1 kappa light chain constant region), D denotes an immunoglobulin heavy chain constant region (e.g., human IgG1 heavy chain constant region), and E denotes an Fc region (e.g., the Fc region from human IgG1). A particular example of the inventive construct is described in Example 11 and depicted in FIG. 8.

The single-domain CD4, eAd, fusion protein, and construct can be prepared by any suitable method. For example, the single-domain CD4, eAd, fusion protein, and construct can be prepared by synthesizing the amino acid sequence(s) or by expressing a nucleic acid(s) encoding the amino acid sequence(s) in a cell and harvesting the resulting polypeptide(s) comprising the single-domain CD4, eAd, fusion protein, and construct from the cell. A combination of such methods also can be used. Methods of de novo synthesizing peptides and methods of recombinantly producing peptides are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994).

Nucleic Acids, Vectors, and Cells

The invention also provides a nucleic acid encoding the amino acid sequence(s) of the single-domain CD4, eAd, fusion protein, and/or construct. The nucleic acid can comprise DNA or RNA, and can be single or double stranded. Furthermore, the nucleic acid can comprise nucleotide analogues or derivatives (e.g., inosine or phosphorothioate nucleotides and the like). For example, the nucleic acid can comprise SEQ ID NO: 2-5, which corresponds to the nucleic acid encoding the m36.1, m36.2, m36.4, or m36.5 eAd, respectively. Additionally, the nucleic acid can comprise SEQ ID NO: 48, SEQ ID NO: 50, or SEQ ID NO: 52, which corresponds to the nucleic acid encoding the m36.4-L2-CD4, m36-L2-CD4-Fc, or m36.4-L2-CD4-Fc fusion protein, respectively.

Additionally or alternatively, the nucleic acid can comprise SEQ ID NO: 33 or 34, which correspond to the mD1 or mD2 variants, respectively. In another aspect, the nucleic acid can comprise (i) SEQ ID NO: 56, (ii) SEQ ID NO: 60, SEQ ID NO: 62, or SEQ ID NO: 64, (iii) SEQ ID NO: 66, SEQ ID NO: 68, or SEQ ID NO: 70, (iv) SEQ ID NO: 72, (v) SEQ ID NO: 74, (vi) SEQ ID NO: 133, or (vii) SEQ ID NO: 135, which correspond to the nucleic acid encoding the (i) gp120-D1, (ii) m36.4-linker-D1, (iii) D1-linker-CH3, (iv) m36.4-linker-D1-linker-CH3, (v) m36.4-linker-D1-Fc, (vi) D1-linker-human IgG1 heavy chain constant region-linker-D1, or (vii) m36.4-linker-human IgG1 light chain constant region-linker-D1 fusion proteins, respectively.

In one embodiment, the nucleic acid comprises SEQ ID NO: 133 and/or 135, which correspond to the fusion proteins comprising D1-linker-human IgG1 heavy chain constant region-linker-D1 (SEQ ID NO: 134) and m36.4-linker-human IgG1 light chain constant region-linker-D1 (SEQ ID NO: 136), respectively.

The nucleic acid can be provided as part of a cassette comprising the nucleic acid and elements that enable delivery of the nucleic acid to a cell, and/or expression of the nucleic acid in a cell. Such elements include, for example, expression vectors, promoters, and transcription and/or translation sequences. Suitable vectors, promoters, transcription/translation sequences, and other elements, as well as methods of preparing such nucleic acids and cassettes, are known in the art (e.g., Sambrook et al., supra; and Ausubel et al., supra).

The invention further provides a recombinant vector comprising the nucleic acid. Examples of suitable vectors include plasmids (e.g., DNA plasmids), yeast (e.g., *Saccharomyces*), and viral vectors, such as poxvirus, retrovirus, adenovirus, adeno-associated virus, herpes virus, polio virus, alphavirus, baculorvirus, and Sindbis virus. When the vector is a plasmid (e.g. DNA plasmid), the plasmid can be complexed with chitosan.

In one embodiment, the vector comprises one or more nucleic acids encoding the construct of the invention. For example, the vector comprises a nucleic acid encoding SEQ ID NO: 134 (e.g., SEQ ID NO: 133) and a nucleic acid encoding SEQ ID NO: 136 (e.g., SEQ ID NO: 135), which correspond to the fusion proteins comprising D1-linker-human IgG1 heavy chain constant region-linker-D1 and m36.4-linker-human IgG1 light chain constant region-linker-D1, respectively. When expressed from the vector, these fusion proteins self-assemble to form the structure depicted in FIG. 8, which comprises two fusion proteins comprising SEQ ID NO: 134 and two fusion proteins comprising SEQ ID NO: 136.

When the vector is for administration to a host (e.g., human), the vector preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

The single-domain CD4, eAd, fusion protein, or construct can be administered to a mammal in the form of a cell comprising a nucleic acid encoding the single-domain CD4, eAd, fusion protein, or construct optionally in the form of a vector. Thus, the invention also provides a cell comprising a vector or nucleic acid encoding the single-domain CD4, eAd, fusion protein, or construct from which the single-domain CD4, eAd, fusion protein, or construct desirably is secreted. Any suitable cell can be used. Examples include host cells, such as *E. coli* (e.g., *E. coli* Tb-1, TG-2, DH5α, XL-Blue MRF' (Stratagene), SA2821, and Y1090), *Bacillus subtilis, Salmonella typhimurium, Serratia marcescens, Pseudomonas* (e.g., *P. aerugenosa*), *N. grassa*, insect cells (e.g., Sf9, Ea4), yeast (*S. cerevisiae*) cells, and cells derived from a mammal, including human cell lines. Specific examples of suitable eukaryotic cells include VERO, HeLa, 3T3, Chinese hamster ovary (CHO) cells, W138 BHK, COS-7, and MDCK cells. Alternatively and preferably, cells from a mammal, such as a human, to be treated in accordance with the methods described herein can be used as host cells. In one embodiment, the cell is a human B cell.

Methods of introducing vectors into isolated host cells and the culture and selection of transformed host cells in vitro are known in the art and include the use of calcium chloride-mediated transformation, transduction, conjugation, triparental mating, DEAE, dextran-mediated transfection, infection, membrane fusion with liposomes, high velocity bombardment with DNA-coated microprojectiles, direct microinjection into single cells, and electroporation (see, e.g., Sambrook et al., supra, Davis et al., *Basic Methods in Molecular Biology* (1986), and Neumann et al., *EMBO J.* 1, 841 (1982)). Desirably, the cell comprising the vector or nucleic acid expresses the nucleic acid encoding the single-domain CD4, eAd, fusion protein, or construct such that the nucleic acid sequence is transcribed and translated efficiently by the cell.

The single-domain CD4, eAd, fusion protein, conjugate, construct, nucleic acid, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

Methods of Use

The single-domain CD4, eAd, fusion protein, conjugate, construct, nucleic acid, vector, or cell can be administered to any host (e.g., mammal, preferably a human) in need thereof. As a result of administration of the single-domain CD4, eAd, fusion protein, conjugate, construct, nucleic acid, vector, or cell to the mammal, infection of the mammal by HIV is inhibited. The inventive method can prophylactically or therapeutically inhibit infection by any type of HIV, but preferably inhibits HIV-1 and/or HIV-2 infection. The inventive method can be used to inhibit infection by any HIV group (e.g., groups M and/or O), and subtype (e.g., clades A, B, C, D, E, EA, F, and/or G).

When provided therapeutically, the single-domain CD4, eAd, fusion protein, conjugate, construct, nucleic acid, vector, cell, or composition thereof is provided at or after the diagnosis of HIV infection.

When provided prophylactically, the single-domain CD4, eAd, fusion protein, conjugate, construct, nucleic acid, vector, cell, or composition thereof is provided in advance of HIV infection, such as to patients or subjects who are at risk for being exposed to HIV or who have been newly exposed to HIV, such as healthcare workers, fetuses, neonates, or infants (e.g., nursing infants) whose mothers are infected or at risk for being infected, intravenous drug users, recipients of blood transfusions, blood products, or transplantation tissue, and other individuals who have been exposed to a body fluid that contains or may contain HIV. The prophylactic administration of the single-domain CD4, eAd, fusion protein, conjugate, construct, nucleic acid, vector, cell, or composition thereof prevents, ameliorates, or delays HIV infection. In subjects who have been newly exposed to HIV but who have not yet displayed the presence of the virus (as measured by PCR or other assays for detecting the virus) in blood or other body fluid, efficacious treatment with the single-domain CD4, eAd, fusion protein, conjugate, construct, nucleic acid, vector, cell, or composition thereof partially or completely inhibits or delays the appearance of the virus or minimizes the level of the virus in the blood or other body fluid of the exposed individual.

The efficacy of the single-domain CD4, eAd, fusion protein, conjugate, construct, nucleic acid, vector, cell, or composition thereof can be assessed in various ways well known to the skilled practitioner. For instance, one of ordinary skill in the art will understand that a single-domain CD4, eAd, fusion protein, conjugate, or construct of the invention is efficacious in treating or inhibiting an HIV infection in a subject by observing that the single-domain CD4, eAd, fusion protein, conjugate, or construct reduces viral load or delays or prevents a further increase in viral load. Viral loads can be measured by methods that are known in the art, for example, using PCR assays to detect the presence of HIV nucleic acid or antibody assays to detect the presence of HIV protein in a sample (e.g., blood or another body fluid) from a subject or patient, or by measuring the level of circulating anti-HIV antibodies in the patient. Efficacy of the single-domain CD4, eAd, fusion protein, conjugate, or construct treatment also can be determined by measuring the number of CD4+ T cells in the HIV-infected subject. A treatment that delays or inhibits an initial or further decrease in CD4+ T cells in an HIV-positive subject or patient, or that results in an increase in the number of CD4+ T cells in the HIV-positive subject, can be considered efficacious.

The single-domain CD4, eAd, fusion protein, conjugate, construct, nucleic acid, vector, or cell can be formulated as a composition (e.g., pharmaceutical composition) comprising the single-domain CD4, eAd, fusion protein, conjugate, construct, nucleic acid, vector, or cell and a carrier (e.g., a pharmaceutically or physiologically acceptable carrier). Furthermore, the single-domain CD4, eAd, fusion protein, conjugate, construct, nucleic acid, vector, cell, or composition of the invention can be used in the methods described herein alone or as part of a pharmaceutical formulation.

Compositions (e.g., pharmaceutical compositions) comprising the single-domain CD4, eAd, fusion protein, conjugate, construct, nucleic acid, vector, or cell can include carriers, thickeners, diluents, buffers, preservatives, surface active agents and the like.

Suitable carriers and their formulations are described in A. R. Gennaro, ed., *Remington: The Science and Practice of Pharmacy* (19th ed.), Mack Publishing Company, Easton, Pa. (1995). Pharmaceutical carriers, include sterile water, saline, Ringer's solution, dextrose solution, and buffered solutions at physiological pH. Typically, an appropriate amount of a pharmaceutically acceptable salt is used in the formulation to render the formulation isotonic. The pH of the formulation is preferably from about 5 to about 8 (e.g., about 5.5, about 6, about 6.5, about 7, about 7.5, and ranges thereof). More preferably, the pH is about 7 to about 7.5. Further carriers include sustained-release preparations, such as semipermeable matrices of solid hydrophobic polymers containing the fusion protein, which matrices are in the form of shaped articles (e.g., films, liposomes, or microparticles). It will be apparent to those persons skilled in the art that certain carriers may be more preferable depending upon, for instance, the route of administration and concentration of composition being administered.

The composition (e.g., pharmaceutical composition) can comprise more than one single-domain CD4, eAd, fusion protein, conjugate, construct, nucleic acid, vector, or cell of the invention. Alternatively, or in addition, the composition can comprise one or more other pharmaceutically active agents or drugs. Examples of such other pharmaceutically active agents or drugs that may be suitable for use in the pharmaceutical composition include anticancer agents (e.g., chemotherapeutic drugs), antibiotics, antiviral drugs, antifungal drugs, cyclophosphamide, and combinations thereof. Suitable antiviral agents (e.g., anti-HIV agents) include, but are not limited to, nucleoside/nucleotide reverse transcriptase inhibitors (e.g., lamivudine, abacavir, zidovudine, stavudine, didanosine, emtricitabine, and tenofovir), non-nucleoside reverse transcriptase inhibitors (e.g., delavirdine, efavirenz, etravirine, and nevirapine), protease inhibitors (e.g., amprenavir, fosamprenavir, atazanavir, darunavir, indinavir, lopinavir, ritonavir, nelfinavir, saquinavir, and tipranavir), fusion or entry inhibitors (e.g., enfuvirtide and maraviroc), integrase inhibitors (e.g., raltegravir), and combination therapies thereof.

Suitable methods of administering a single-domain CD4, eAd, fusion protein, conjugate, construct, nucleic acid, vector, cell, or composition thereof to hosts are known in the art. The host can be any suitable host, such as a mammal (e.g., a rodent, such as a mouse, rat, hamster, or guinea pig, rabbit, cat, dog, pig, goat, cow, horse, primate, or human).

Administration can be topical (including ophthalmical, vaginal, rectal, intranasal, transdermal, and the like), oral, by inhalation, or parenteral (including by intravenous drip or subcutaneous, intracavity, intraperitoneal, or intramuscular injection). Topical intranasal administration refers to the delivery of the compositions into the nose and nasal passages through one or both of the nares and can comprise delivery by a spraying mechanism or droplet mechanism, or through aerosolization of the nucleic acid, vector, or fusion protein. Administration of the compositions by inhalant can be through the nose or mouth via delivery by a spraying or droplet mechanism. Delivery can also be directly to any area of the respiratory system (e.g., lungs) via intubation.

Formulations for topical administration include ointments, lotions, creams, gels, drops, suppositories, sprays, liquids, and powders. Conventional pharmaceutical carriers, aqueous, powder, or oily bases, thickeners, and the like may be necessary or desirable.

If the composition is to be administered parenterally, the administration is generally by injection. Injectables can be prepared in conventional forms, either as liquid solutions or suspensions, solid forms suitable for suspension in liquid prior to injection, or as emulsions. Additionally, parental administration can involve the preparation of a slow-release or sustained-release system, such that a constant dosage is maintained. Preparations for parenteral administration include sterile aqueous or non-aqueous solutions, suspensions, and emulsions. Examples of non-aqueous solvents are propylene glycol, polyethylene glycol, vegetable oils, such as olive oil, and injectable organic esters, such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives also can be present such as, for example, antimicrobials, anti-oxidants, chelating agents, and inert gases, and the like.

Compositions for oral administration include powders or granules, suspensions or solutions in water or non-aqueous media, capsules, sachets, or tablets. Thickeners, flavorings, diluents, emulsifiers, dispersing aids, or binders may be desirable.

Some of the compositions can potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base, such as sodium hydroxide, ammonium hydroxide, potassium hydroxide, and organic bases, such as mono-, di-, trialkyl, and aryl amines and substituted ethanolamines.

The single-domain CD4, eAd, fusion protein, conjugate, construct, nucleic acid, vector, or cell can be administered with a pharmaceutically acceptable carrier and can be delivered to the mammal's cells in vivo and/or ex vivo by a variety of mechanisms well-known in the art (e.g., uptake of naked DNA, liposome fusion, intramuscular injection of DNA via a gene gun, endocytosis, and the like).

Additionally, probiotic therapies are envisioned by the present invention. Viable host cells containing the nucleic acid or vector of the invention and expressing the fusion protein, conjugate, or construct can be used directly as the delivery vehicle for the fusion protein to the desired site(s) in vivo. Preferred host cells for the delivery of the fusion protein, conjugate, or construct directly to desired site(s), such as, for example, to a selected body cavity, can comprise bacteria. More specifically, such host cells can comprise suitably engineered strain(s) of lactobacilli, enterococci, or other common bacteria, such as *E. coli*, normal strains of which are known to commonly populate body cavities. More specifically yet, such host cells can comprise one or more selected nonpathogenic strains of lactobacilli, such as those described by Andreu et al., *J. Infect. Dis.*, 171(5), 1237-43 (1995), especially those having high adherence properties to epithelial cells (e.g., vaginal epithelial cells) and suitably transformed using the nucleic acid or vector of the invention.

If ex vivo methods are employed, cells or tissues can be removed and maintained outside the body according to standard protocols known in the art. The compositions can be introduced into the cells via any gene transfer mechanism, such as calcium phosphate mediated gene delivery, electroporation, microinjection, or proteoliposomes. The transduced cells then can be infused (e.g., with a pharmaceutically acceptable carrier) or homotopically transplanted back into the mammal per standard methods for the cell or tissue type. Standard methods are known for transplantation or infusion of various cells into a mammal.

The exact amount of the composition required to treat an HIV infection will vary from mammal to mammal, depending on the species, age, gender, weight, and general condition of the mammal, the nature of the virus, the existence and extent of viral infection, the particular fusion proteins, nucleic acid, vector, or cell used, the route of administration, and whether other drugs are included in the regimen. Thus, it is not possible to specify an exact amount for every composition. However, an appropriate amount can be determined by one of ordinary skill in the art using only routine experimentation given the teachings herein. Effective dosages and schedules for administering the nucleic acid molecules, vectors, cells, and fusion proteins of the invention can be determined empirically, and making such determinations is within the skill in the art. The dosage ranges for the administration of the compositions are those large enough to produce the desired effect; however, the dosage should not be so large as to cause adverse side effects, such as unwanted cross-reactions, anaphylactic reactions, and the like. Dosage can vary, and can be administered in one or more (e.g., two or more, three or more, four or more, or five or more) doses daily, for one or more days. The composition can be administered before HIV infection or immediately upon determination of HIV infection and continuously administered until the virus is undetectable.

The single-domain CD4, eAd, fusion protein, conjugate, construct, nucleic acid, vector, cell, or composition thereof is administered to a host (e.g., mammal, such as a human) in an amount effective to prophylactically or therapeutically inhibit an HIV infection. The efficacy of the single-domain CD4, eAd, fusion protein, conjugate, construct, nucleic acid, vector, cell, or composition thereof as an HIV infection inhibitor may be determined by in vivo or in vitro parameters known in the art.

Any suitable dose of the single-domain CD4, eAd, fusion protein, conjugate, construct, nucleic acid, vector, cell, or composition thereof can be administered to a host. The appropriate dose will vary depending upon such factors as the host's age, weight, height, sex, general medical condition, previous medical history, and HIV infection progression and can be determined by a clinician. For example, the single-domain CD4, eAd, fusion protein, conjugate, or construct can be administered in a dose of about 1 µg/kg to up to 100 mg/kg of body weight or more per day (e.g., 5 µg/kg, 10 µg/kg, 50 µs/kg, 100 µg/kg, 200 µg/kg, 300 µg/kg, 400 µg/kg, 500 µg/kg, 600 µg/kg, 700 µg/kg, 800 µg/kg, 900 µg/kg, 1 mg/kg, 2 mg/kg, 5 mg/kg, 10 mg/kg, 20 mg/kg, 30 mg/kg, 40 mg/kg, 50 mg/kg, 60 mg/kg, 70 mg/kg, 80 mg/kg, 90 mg/kg, and ranges thereof) to the host (e.g., mammal, such as a human). Several doses (e.g., 1, 2, 3, 4, 5, 6, or more) can be provided (e.g., over a period of weeks or months).

When the vector is a viral vector, a suitable dose can include about $1\times10^5$ to about $1\times10^{12}$ (e.g., $1\times10^6$, $1\times10^7$, $1\times10^8$, $1\times10^9$, $1\times10^{10}$, $1\times10^{11}$, and ranges thereof) plaque forming units (pfus), although a lower or higher dose can be administered to a host. For example, about $2\times10^8$ pfus can be administered (e.g., in a volume of about 0.5 mL).

The inventive cells can be administered to a host in a dose of between about $1\times10^5$ and $2\times10^{11}$ (e.g., $1\times10^6$, $1\times10^7$, $1\times10^8$, $1\times10^9$, $1\times10^{10}$, and ranges thereof) cells per infusion. The cells can be administered in, for example, one to three (e.g., two) infusions. In addition to the administration of the cells, the host can be administered a biological response modifier, such as interleukin 2 (IL-2).

The single-domain CD4, eAd, fusion protein, conjugate, or construct can be used in combination with other well-known HIV therapies and prophylactic vaccines already in use. The combination of the fusion protein of the invention can generate an additive or a synergistic effect with current treatments. The single-domain CD4, eAd, fusion protein, conjugate, or construct of the invention can be combined with other HIV and AIDS therapies and vaccines, such as highly active anti-retroviral therapy (HAART), which comprises a combination of protease inhibitors and reverse transcriptase inhibitors, azidothymidine (AZT), structured treatment interruptions of HAART, cytokine immune enhancement therapy (e.g., interleukin (IL)-2, IL-12, CD40L+IL-12, IL-7, HIV protease inhibitors (e.g., ritonavir, indinavir, and nelfinavir, etc.), and interferons (IFNs)), cell replacement therapy, recombinant viral vector vaccines, DNA vaccines, inactivated virus preparations, immunosuppressive agents, such as Cyclosporin A, cyanovirin therapy (see, e.g., U.S. Pat. No. 6,015,876), scytovirin therapy (see, e.g., U.S. Pat. No. 7,491,798), and griffithsin therapy (see, e.g., U.S. Patent Application Publication 2009-0092557). Such therapies can be administered in the manner already in use for the known treatment providing a therapeutic or prophylactic effect (see, e.g., Silvestri et al. Immune Intervention in AIDS. In: *Immunology of Infectious Disease*, H. E. Kauffinan, A. Sher, and R. Ahmed eds., ASM Press, Washington D.C. (2002)).

The following examples further illustrate the invention but, of course, should not be construed as in any way limiting its scope.

EXAMPLE 1

This example demonstrates the generation of a phage-displayed library of m36 and the identification of the m36.1, m36.2, m36.4, and m36.5 antibodies.

To introduce point mutations, random DNA mutagenesis was performed using the Gene-Morph PCR Mutagenesis Kit (Strategene, La Jolla, Calif.). m36 gene fragments with mutations were PCR amplified using m36-encoding plasmid as a template and primers m36F1
(sense; SEQ ID NO: 54)
(5'-TGGTTTCGCTACCGTGGCCCAGGCGGCCCAGGTGCAGCTGGT G-3')
and HISR
(antisense; SEQ ID NO: 55)
(5'-GTCGCCGTGGTGGTGGTGGTGGCCGGCCTGGCCACTTG-3').

The PCR products were gel-purified, digested with SfiI, and gel-purified again. The purified fragments then were cloned into the phagemid pComb3X linearized by SfiI. A phage library was prepared by electroporation of *Escherichia coli* (*E. coli*) strain TG1 electroporation-competent cells (Stratagene, La Jolla, Calif.) with desalted and concentrated ligation, as described in Chen et al., *J. Mol. Biol.*, 382: 779-789 (2008).

The library (phage) was used for selection of m36 mutants against HIV-1 antigens conjugated to magnetic beads (Dynabeads M-270 epoxy; DYNAL Inc., New Hyde Park, N.Y.) as described in Zhu et al., *J. Virol.*, 80: 891-899 (2006). The library was panned sequentially against two different Envs from clade B isolates, gp120$_{Bal}$ and gp140$_{JRFL}$. 5, 2.5, and 0.5 μg of gp120$_{Bal}$ were used in the first, third and fifth rounds, respectively; antigens were alternated with 5, 2.5, and 0.5 μg of gp140$_{JRFL}$ during the second, fourth and sixth rounds. To identify individual antibodies that specifically bound to both antigens, clones were randomly selected after six rounds of panning and subjected to soluble expression-based monoclonal ELISA (semELISA) as described in Chen et al., *Mol. Immunol.*, 47:912-921 (2010).

Sequencing of a number of positive clones revealed that they represented four different clones, designated m36.1, m36.2, m36.4, and m36.5, respectively (see FIG. 1). These clones also were selected by panning the library sequentially with gp140$_{SC}$ (clade B) and gp140$_{CAP}$ (clade C). Notably, three (m36.1, m36.4, and m36.5) of the clones acquired the same mutation (44Q/E) to an acidic residue in the framework (FR) 2 (FR2) compared to m36; the other one (m36.2) also carried an acidic residue substitution (45A/D) at a close position. Besides m36.4, the other three mutants contained additional mutations in various positions (see FIG. 1).

Figure 2B:
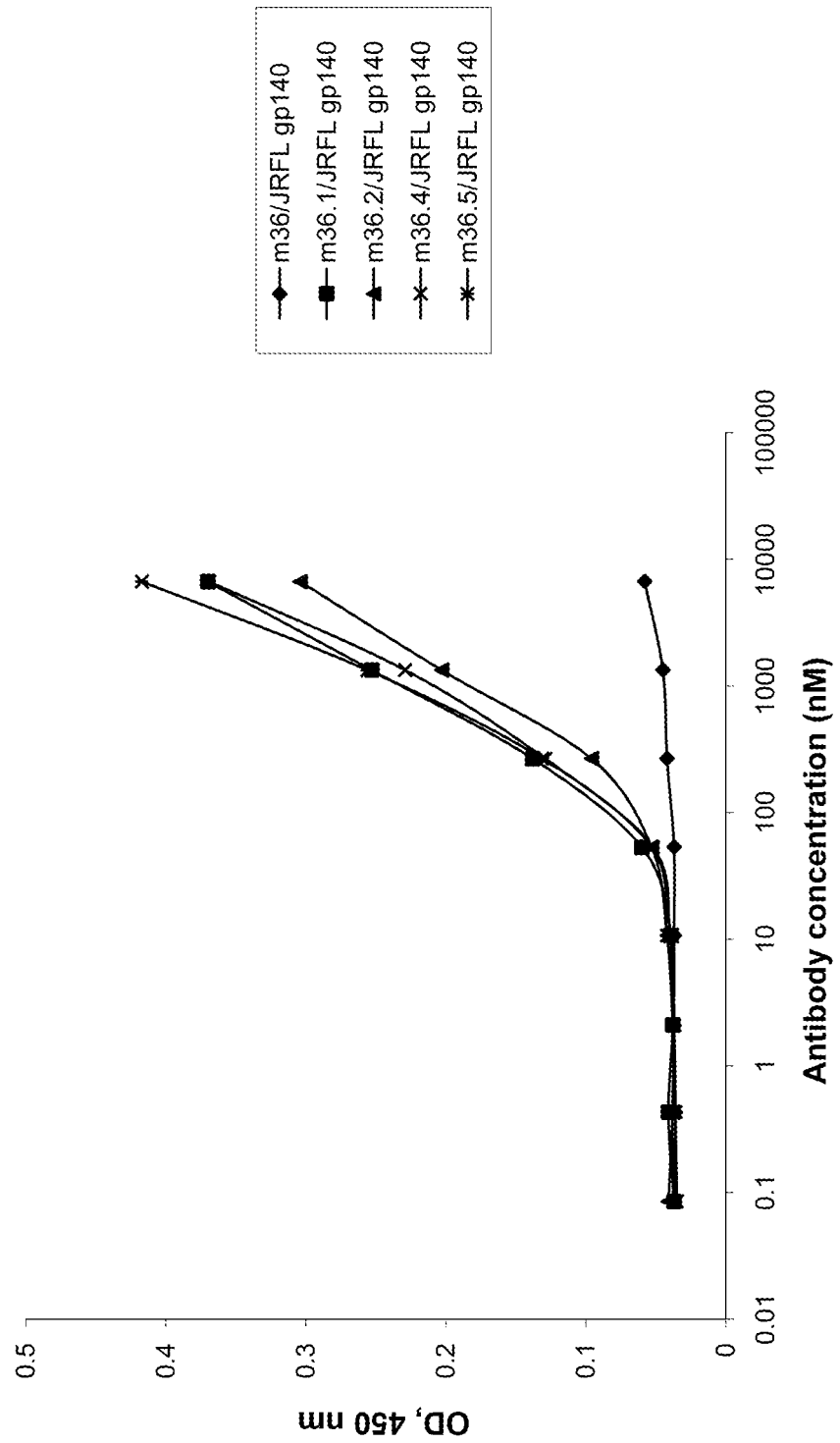
Figure 2C:
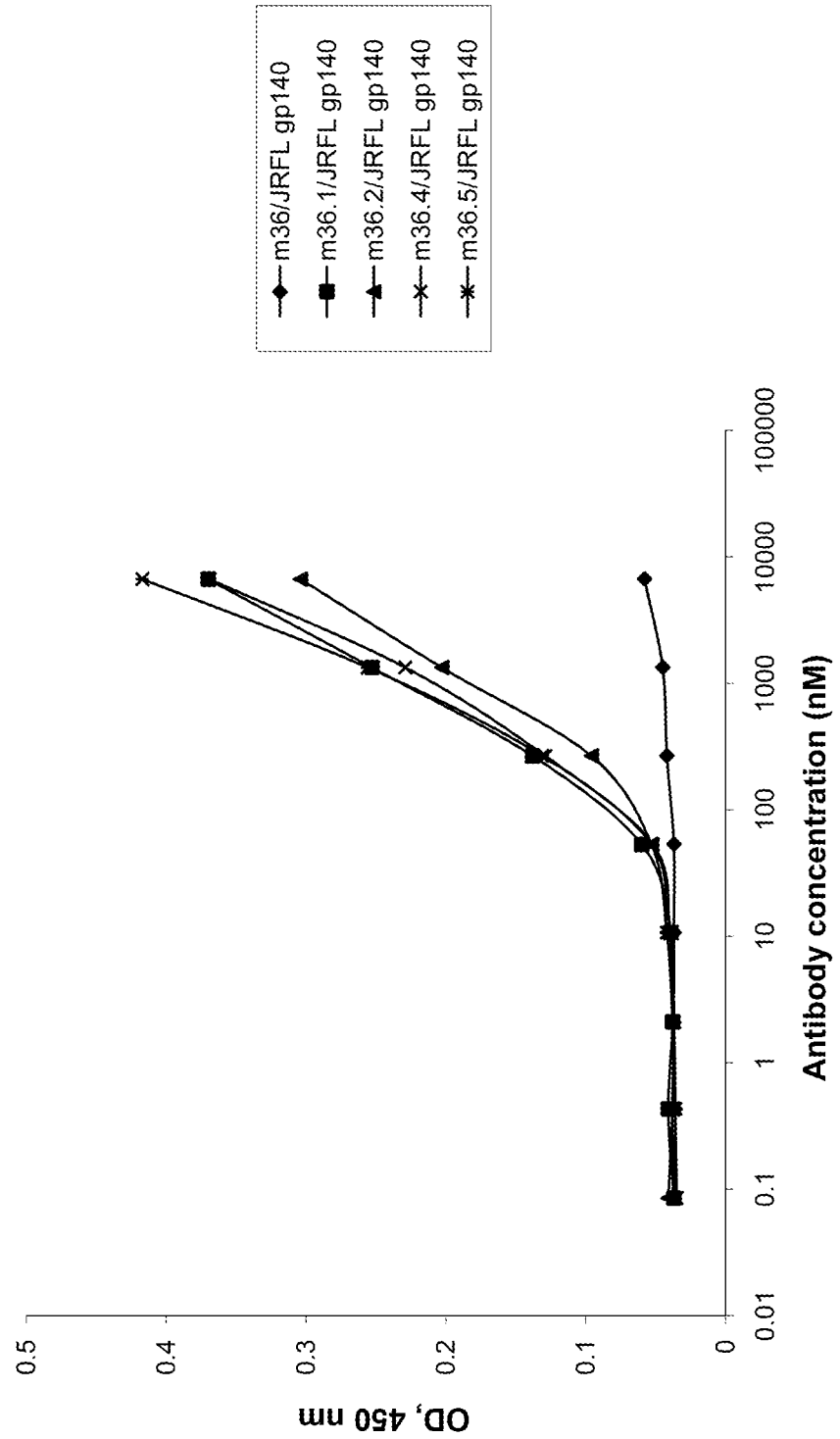

In ELISA-based assays, these mutants showed specific and significantly higher binding than m36 to gp120$_{Bal}$ (see FIG. 2A) and gp140$_{JRFL}$ (see FIG. 2B) in the absence of CD4. These mutants also bound much better to gp140$_{SC}$ (see FIG. 2C) and gp140$_{CAP}$ than m36. Although these antibodies were selected against Envs only, slightly increased interaction with 120$_{Bal}$-CD4 complex also was observed with some of the mutants (see FIG. 2D).

To determine whether the observed increase in binding resulted in more potent neutralization than m36, m36.4 was tested with a small panel of HIV-1 Env-pseudotyped viruses from genetically diverse primary or lab-adapted isolates. As shown in Tables 1A, 1B, 2A, and 2B, m36.4 exhibited higher potency than m36 with on average about one-fold decrease in both IC$_{50}$s and IC$_{90}$s. Higher order of magnitude of decrease in IC$_{50}$s were observed when 92UG037.8 (clade A) and CM243 (clade E) were tested.

TABLE 1A

Neutralization (IC$_{50}$) of m36, m36.4, and their fusion proteins against HIV-1 pseudotyped from different clades.

| Viruses | Clade | Tropism | IC$_{50}$ (nM) | | | | | |
|---|---|---|---|---|---|---|---|---|
| | | | m36 | m36.4 | m36L2CD4 | m36.4L2CD4 | m36L2CD4Fc | m36.4L2CD4Fc |
| 92UG037.8 | A | R5 | 210 | 11[1] | 16[1] | 17[1] | 18[1] | 27[2] |
| Bal | B | R5 | 23 | 21 | <8[2] | <8[2] | <8[1] | <8[1] |
| JRFL | B | R5 | 70 | 23[3] | 15[3] | 9[2] | <8[1] | <8[1] |
| IIIB | B | X4 | <8 | <8 | <8[1] | <8[1] | <8[1] | <8[1] |
| AD8 | B | R5 | 23 | 20 | 76[4] | ND | 19 | 20 |
| 92HT | B | R5X4 | <8 | <8 | <8 | ND | <8 | <8 |
| 89.6 | B | R5X4 | 18 | 10 | <8[1] | <8[1] | <8[1] | <8[1] |
| NL4-3 | B | X4 | <8 | <8 | <8 | <8 | <8 | <8 |
| R2 | B | R5 | 29 | 13[3] | <8[1] | 9[3] | <8[1] | <8[1] |
| JRCSF | B | R5 | 30 | 12[3] | 16 | 39 | 23 | 33 |
| GXC-44 | C | R5 | <8 | <8 | <8 | <8 | 18[4] | 8 |
| Z2Z6 | D | R5 | 667 | >667[4] | 485 | ND | 60[1] | 570 |
| CM243 | E | R5 | 635 | 156[3] | 9[1] | ND | <8[1] | <8[1] |
| GXE | E | R5 | — | >667 | 230[1] | 215[1] | 70[1] | 220[1] |

[1] At least 9-fold increase compared to m36
[2] At least 4-fold increase compared to m36
[3] At least 1-fold increase compared to m36
[4] At least 1-fold decrease compared to m36
— no significant neutralization observed at the highest concentration
ND not determined

TABLE 1B

Neutralization (%) of m36, m36.4, and their fusion proteins against HIV-1 pseudotyped from different clades.

| Viruses | Clade | Tropism | Neutralization (%) at the lowest concentration (8 nM) | | | | | |
|---|---|---|---|---|---|---|---|---|
| | | | m36 | m36.4 | m36L2CD4 | m36.4L2CD4 | m36L2CD4Fc | m36.4L2CD4Fc |
| 92UG037.8 | A | R5 | 0 | 43 | 35 | 26 | 31 | 34 |
| Bal | B | R5 | 17 | 23 | 68 | 75 | 92 | 93 |
| JRFL | B | R5 | 0 | 17 | 32 | 46 | 61 | 64 |
| IIIB | B | X4 | 62 | 79 | 100 | 100 | 100 | 100 |
| AD8 | B | R5 | 27 | 34 | 0 | ND | 31 | 27 |
| 92HT | B | R5X4 | 92 | 77 | 76 | ND | 56 | 59 |
| 89.6 | B | R5X4 | 36 | 30 | 84 | 75 | 90 | 96 |
| NL4-3 | B | X4 | 90 | 96 | 99 | 95 | 99 | 99 |
| R2 | B | R5 | 16 | 34 | 78 | 42 | 81 | 75 |
| JRCSF | B | R5 | 27 | 44 | 39 | 9 | 20 | 10 |
| GXC-44 | C | R5 | 62 | 53 | 71 | 59 | 34 | 50 |

TABLE 1B-continued

Neutralization (%) of m36, m36.4, and their fusion proteins against HIV-1 pseudotyped from different clades.

| | | | Neutralization (%) at the lowest concentration (8 nM) | | | | |
|---|---|---|---|---|---|---|---|
| Viruses | Clade | Tropism | m36 | m36.4 | m36L2CD4 | m36.4L2CD4 | m36L2CD4Fc | m36.4L2CD4Fc |
| Z2Z6 | D | R5 | 40 | 19 | 26 | ND | 25 | 24 |
| CM243 | E | R5 | 0 | 36 | 45 | ND | 70 | 59 |
| GXE | E | R5 | 0 | 0 | 0 | 0 | 0 | 28 |

ND not determined

TABLE 2A

Neutralization ($IC_{90}$) of m36, m36.4, and their fusion proteins against HIV-1 pseudotyped from different clades.

| | | | IC90 (nM) | | | | |
|---|---|---|---|---|---|---|---|
| Viruses | Clade | Tropism | m36 | m36.4 | m36L2CD4 | m36.4L2CD4 | m36L2CD4Fc | m36.4L2CD4Fc |
| 92UG037.8 | A | R5 | >667 | >667 | 75[1] | 78[1] | 225[3] | 153[2] |
| Bal | B | R5 | 130 | 77 | 23[2] | 18[2] | <8[1] | <8[1] |
| JRFL | B | R5 | 350 | 200 | 75[3] | 69[2] | 44[2] | 41[2] |
| IIIB | B | X4 | 30 | 20 | <8[1] | <8[1] | <8[1] | <8[1] |
| AD8 | B | R5 | 175 | 69[3] | 420[4] | ND | 115 | 76[3] |
| 92HT | B | R5X4 | 8 | 39[4] | 37[4] | ND | 223[4] | 230[4] |
| 89.6 | B | R5X4 | 170 | 76[3] | 19[2] | 151 | 81 | <81 |
| NL4-3 | B | X4 | 8 | <8 | <8 | <8 | <8 | <8 |
| R2 | B | R5 | 220 | 104[3] | 36[2] | 26[2] | 44[2] | 25[2] |
| JRCSF | B | R5 | 120 | 102 | 153 | 340[4] | 155 | 148 |
| GXC-44 | C | R5 | 74 | 50 | 100 | 125 | 220[4] | 225[4] |
| Z2Z6 | D | R5 | >667 | >667 | >667 | ND | >667 | >667 |
| CM243 | E | R5 | >667 | >667 | 170[2] | ND | 580[3] | >667 |
| GXE | E | R5 | — | >667[3] | >667[1] | >667[1] | >667[1] | >667[1] |

[1] At least 9-fold increase compared to m36
[2] At least 4-fold increase compared to m36
[3] At least 1-fold increase compared to m36
[4] At least 1-fold decrease compared to m36
— no significant neutralization observed at the highest concentration
ND not determined

TABLE 2B

Neutralization (%) of m36, m36.4, and their fusion proteins against HIV-1 pseudotyped from different clades.

| | | | Neutralization (%) at the highest concentration (667 nM) | | | | |
|---|---|---|---|---|---|---|---|
| Viruses | Clade | Tropism | m36 | m36.4 | m36L2CD4 | m36.4L2CD4 | m36L2CD4Fc | m36.4L2CD4Fc |
| 92UG037.8 | A | R5 | 80 | 87 | 94 | 97 | 95 | 94 |
| Bal | B | R5 | 99 | 99 | 100 | 100 | 100 | 100 |
| JRFL | B | R5 | 96 | 99 | 99 | 100 | 99 | 99 |
| IIIB | B | X4 | 100 | 100 | 100 | 100 | 100 | 100 |
| AD8 | B | R5 | 99 | 99 | 98 | ND | 99 | 97 |
| 92HT | B | R5X4 | 95 | 96 | 97 | ND | 91 | 91 |
| 89.6 | B | R5X4 | 96 | 90 | 99 | 98 | 95 | 96 |
| NL4-3 | B | X4 | 100 | 100 | 99 | 99 | 99 | 99 |
| R2 | B | R5 | 90 | 95 | 97 | 98 | 95 | 94 |
| JRCSF | B | R5 | 98 | 98 | 99 | 98 | 96 | 94 |
| GXC-44 | C | R5 | 98 | 97 | 97 | 98 | 95 | 91 |
| Z2Z6 | D | R5 | 48 | 37 | 59 | ND | 67 | 57 |
| CM243 | E | R5 | 57 | 75 | 92 | ND | 91 | 84 |
| GXE | E | R5 | 0 | 9 | 61 | 70 | 71 | 62 |

ND not determined

EXAMPLE 2

This example demonstrates the preparation of a fusion protein in accordance with the invention.

The fusion protein (m36hlFc) of m36 fused to the human IgG1 Fc previously had been prepared (see Chen et al., *Proc. Natl. Acad. Sci. U.S.A.*, 105: 17121-17126 (2008)). m36h1Fc exhibited higher binding to gp120 than m36. However, there was a decrease in neutralization against most of the isolates tested likely because of the sterically restricted nature of m36 epitope that limits access of large antibody derivatives.

Figure 3A:
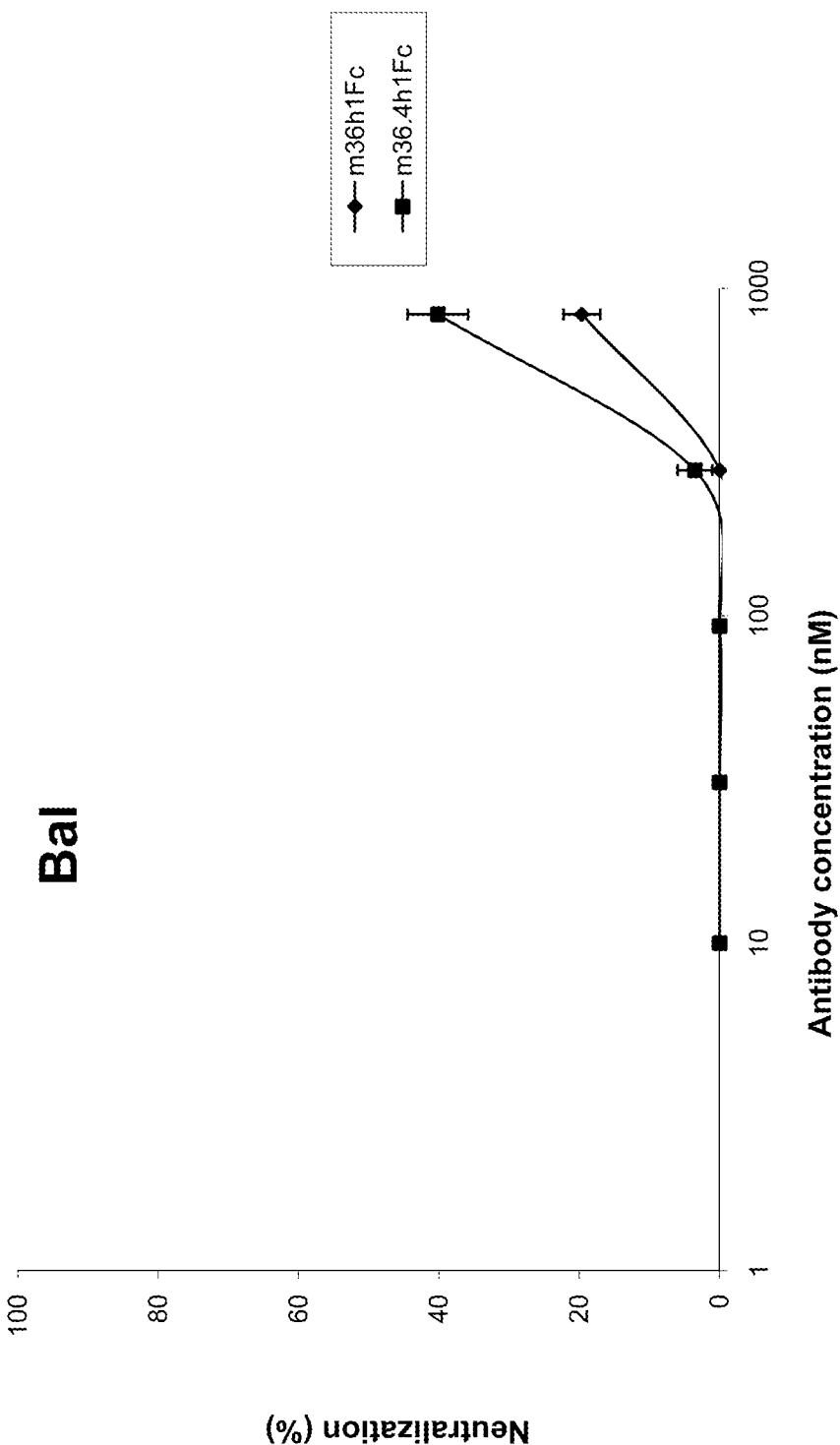
FIGS. 3A-C are graphs showing the dose-dependent neutralization of Bal (FIG. 3A), JRFL (FIG. 3B), and 89.6 (FIG. 3C) by m36h1Fc and m36.4h1Fc. Antibody concentration (nM) is on the x-axis and percent neutralization is on the y-axis. The assays were performed on HOS-CD4-CCR5 cells, and pseudotyped viruses were generated from 293T cells.
Figure 3B:
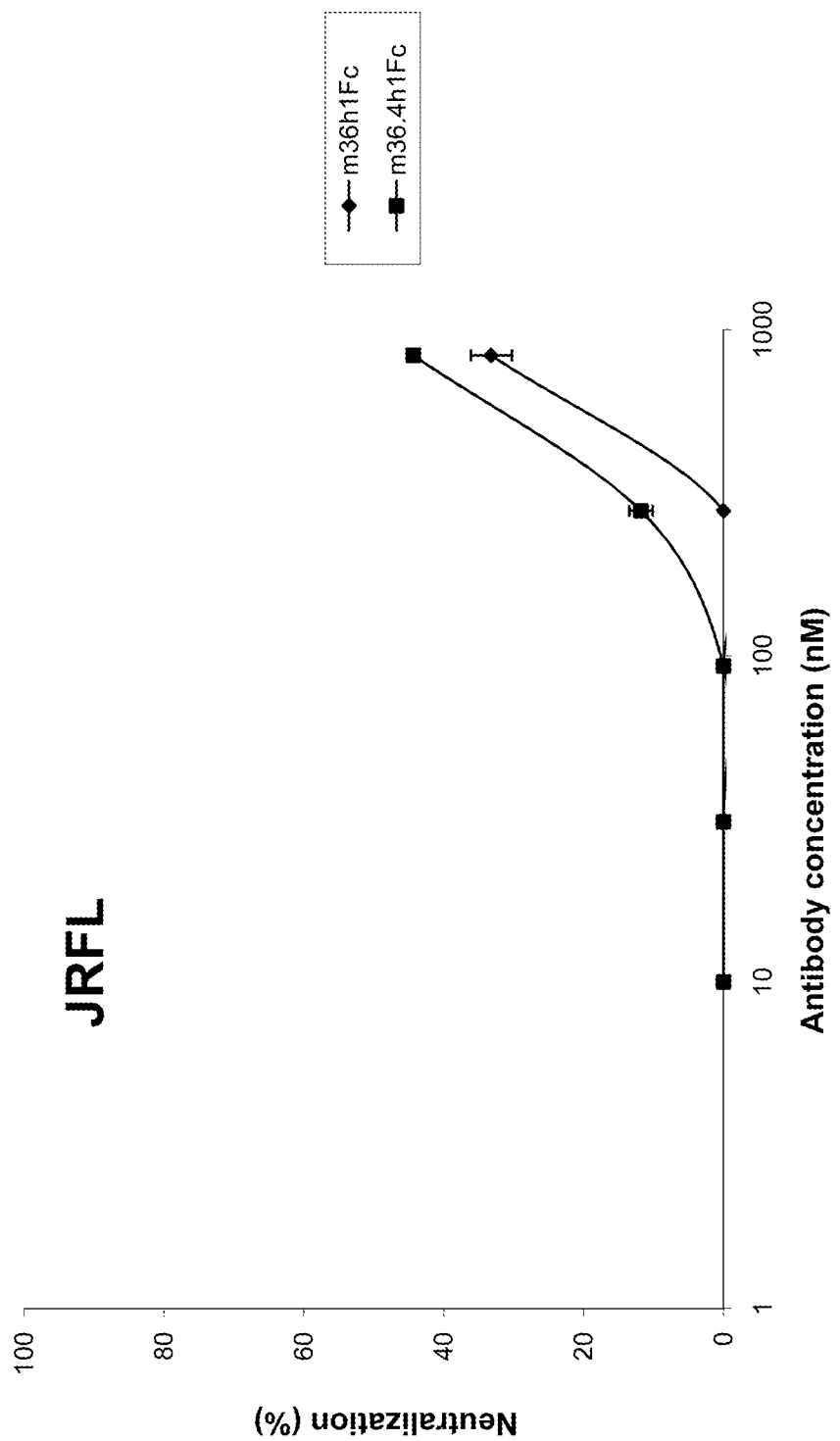
Figure 3C:
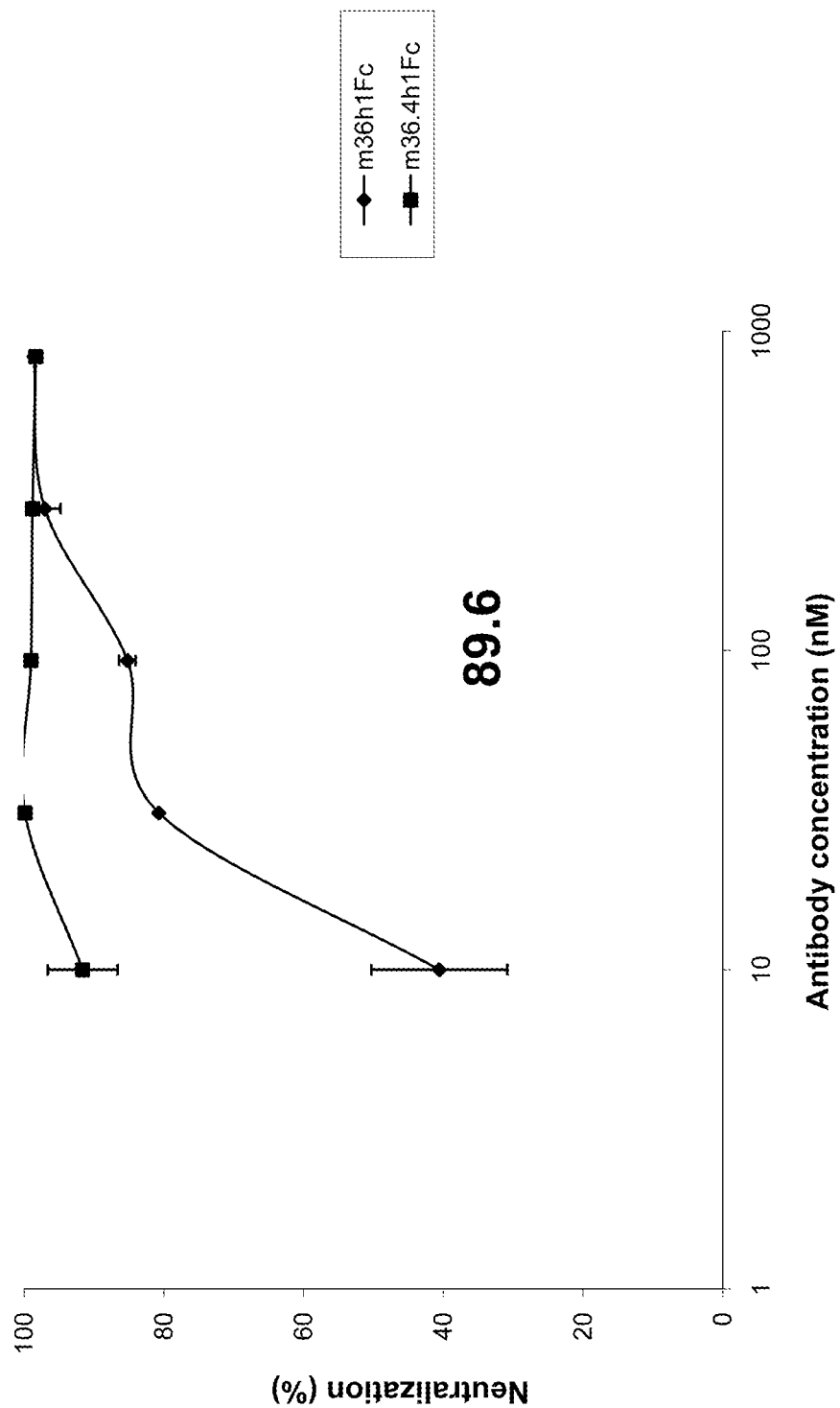

The same fusion protein was prepared for m36.4, designated m36.4h1Fc. It was tested side by side with m36h1Fc against three isolates, Bal, JRFL and 89.6, of which the first two were barely neutralized and the last one was efficiently neutralized by m36h1Fc in a previous study. The results showed that m36.4h1Fc exhibited better neutralization than m36h1Fc to Bal and JRFL while having a much greater increase in antiviral activity against 89.6 (see FIG. 3A-C).

Figure 4:
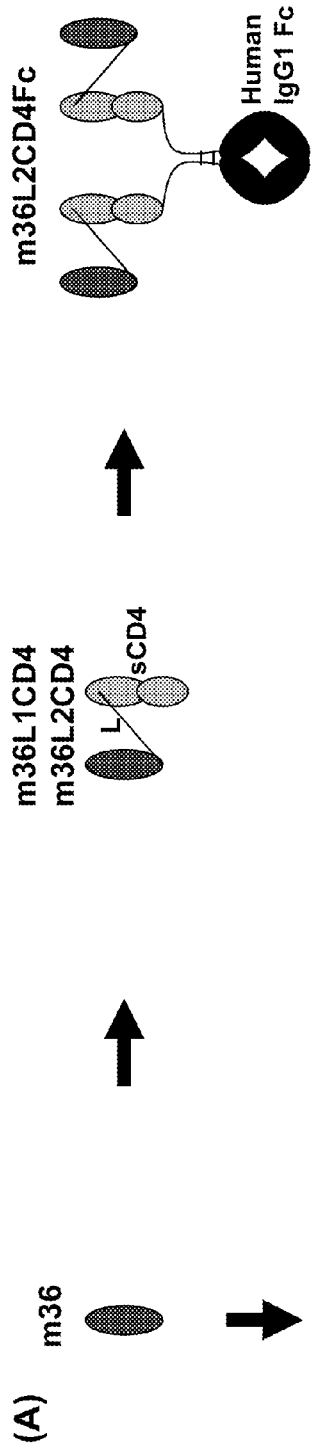
FIGS. 4A-B illustrate fusion proteins of m36 and m36.4.
Figure 4:
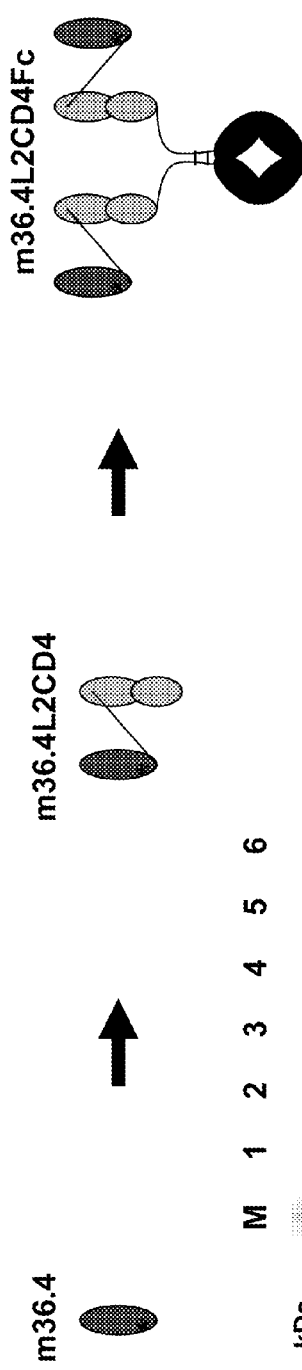
Figure 4:
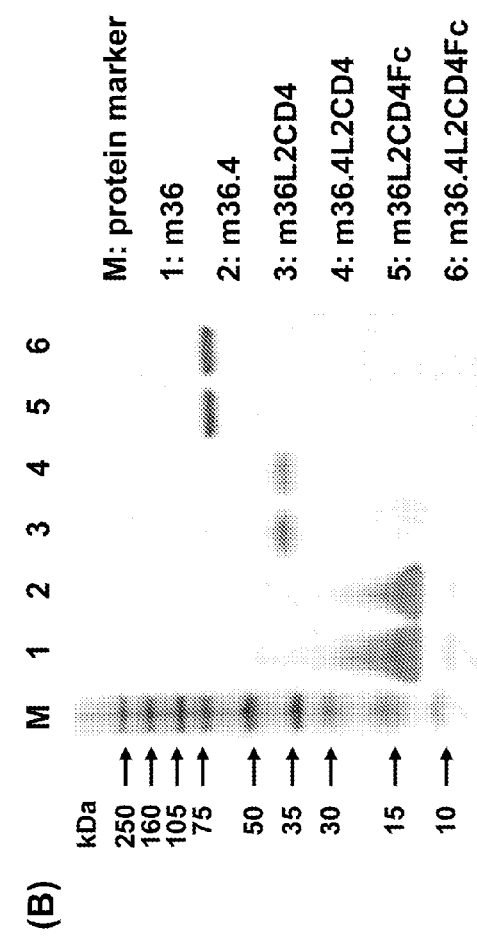

Additional fusion proteins were prepared using human sCD4. First, the appropriate order was determined of the eAd and sCD4 in the single-chain chimeric fusion proteins. In a separate experiment, two homodimers of m36 were made. In one construct (m36d1), two m36 molecules were covalently linked by a polypeptide composed of three repeats of $G_4S$ motif. In the other construct (m36d2), a single cysteine was introduced to a polypeptide tail at the C-terminal of m36 and dimerization of the purified protein via a disulfide bond was determined by size-exclusion chromatography and non-reducing and reducing SDS-PAGE. Binding to gp120s and neutralization of m36d1 were decreased by ~16 fold and ~3 fold, respectively, compared to those of m36, while m36d2 showed comparable or better binding and neutralization than m36. These results suggest that in m36d1 the linker could interrupt recognition of the second m36 molecule—possibly because the linker is in too close proximity to the antigen-binding site (N-terminal) of the second m36. Therefore, m36 was joined to the N-terminal of human sCD4 (FIG. 4A). Because the N-terminal of sCD4 is relatively far away from the binding site of gp120 according to the crystal structure of a gp120-sCD4 complex, it is assumed that the polypeptide linkers used will not interfere with interaction of sCD4 with gp120.

Figure 5B:
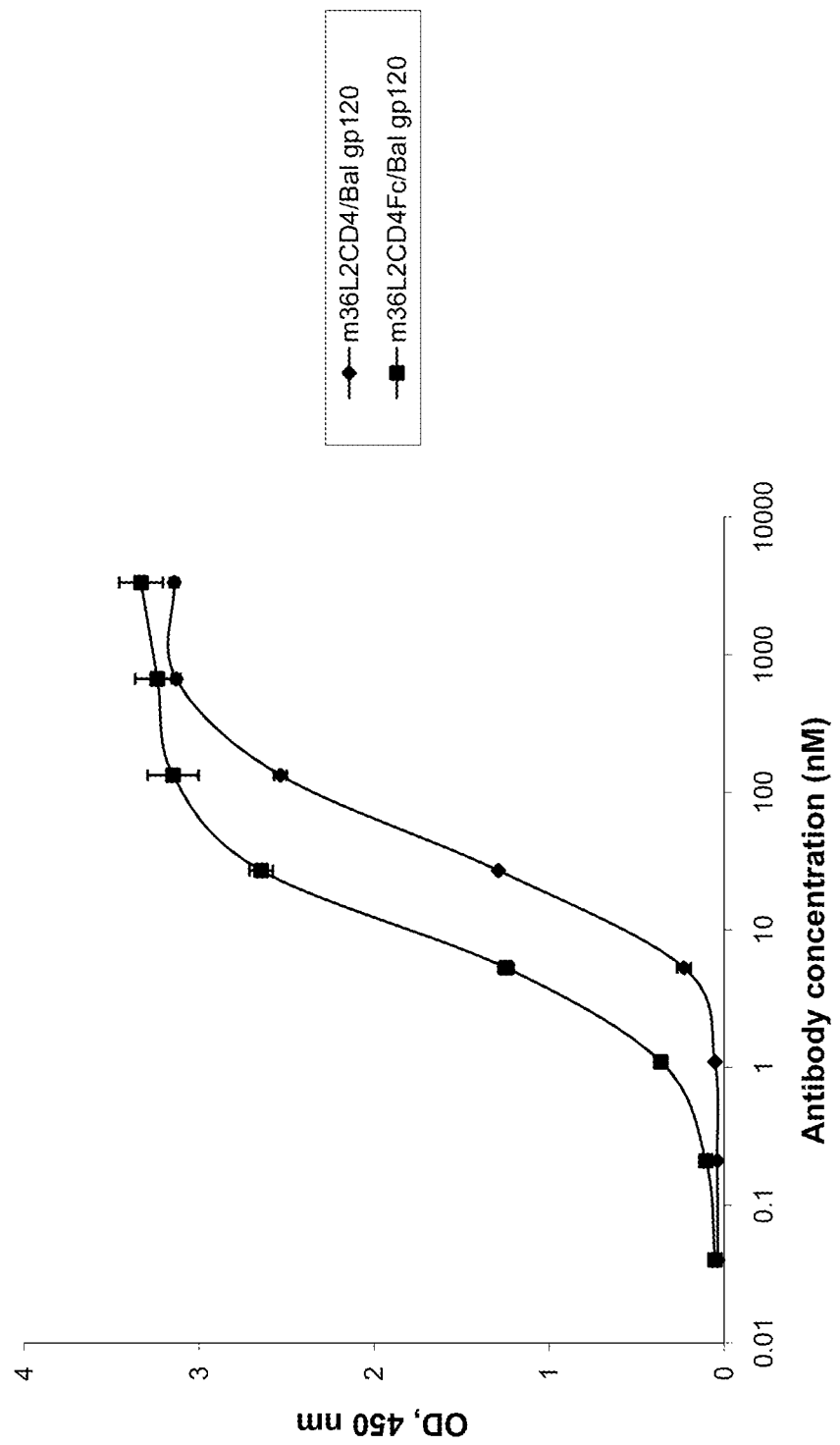

Second, a natural linker derived from the M13 bacteriophage was used, wherein the linker connects the second and third domains of capsid protein pIII. To explore the effects of linker length, full-length bacteriophage pIII linker (L1, 39 residues, SEQ ID NO: 11) was used in one construct (m36L1CD4) and an empirically shortened linker (L2, 27 residues, SEQ ID NO: 12) was used in the other construct (m36L2CD4) (see FIGS. 4A and B).

m36L1 CD4 and m36L2CD4 were expressed in the transiently transfected 293 free style cells. The proteins were secreted into the shaking culture supernatants. Both proteins ran on reducing SDS-PAGE with an apparent molecular weight (MWa) of ~40 kDa, which was close to the calculated MW (MWc) (37.192 kDa for m36L1CD4 and 36.417 kDa for m36L2CD4, including the His and FLAG tags) (see FIG. 4C). In an ELISA, the fusion proteins bound to gp120$_{Bal}$ much better than m36 or sCD4 alone, or a combination of m36 and sCD4 (in the same molarity), suggesting the synergistic and/or avidity effects between m36 and sCD4 on the fusion protein binding (see FIG. 5A). Notably, m36L2CD4 bound even better than m36L1CD4 indicating that the shortened linker L2 could provide better flexibility. However, obvious difference in neutralization potencies between the two constructs against several isolates tested were not observed. Linker L2 was selected for generation of additional m36-based fusion proteins.

Figure 5C:
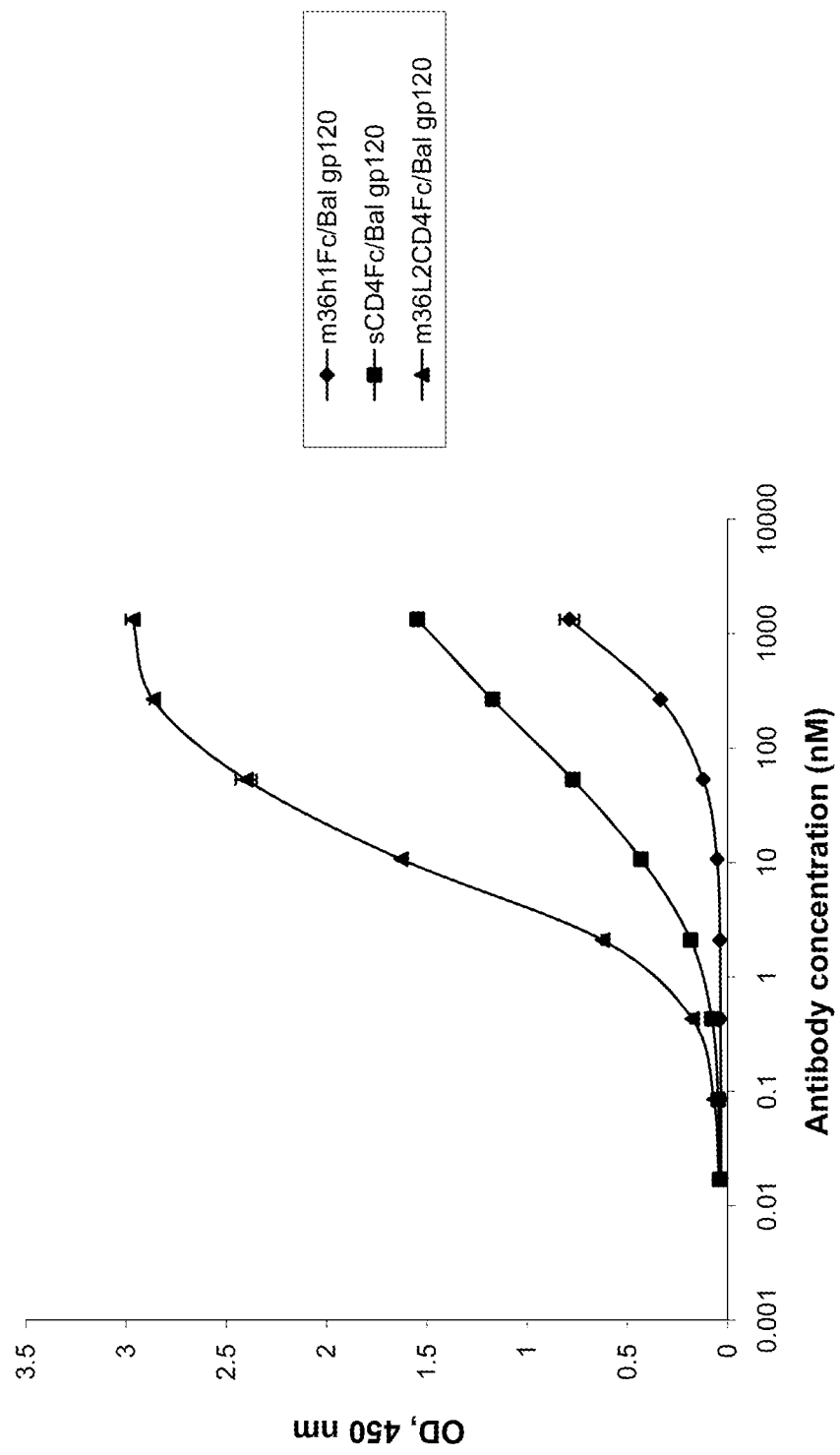

In an effort to achieve more avidity effects, increased serum half life, and biological effector functions, m36L2CD4 was further fused to the human IgG1 Fc (see FIG. 4A-B). The new construct, designated m36L2CD4Fc, was well expressed and easily purified from the shaking 293 free style cell culture supernatant. It bound to gp120$_{Bal}$ with an EC$_{50}$ (~8 nM) higher than that (20-30 nM) of m36L2CD4 (see FIG. 5B). To rule out the possibility that the strong binding resulted mainly from the dimerization of either m36 or sCD4, a fusion protein (sCD4Fc) of sCD4 with the human IgG1 Fc was prepared and the binding of m36L2CD4Fc was compared to that of m36h1Fc and sCD4Fc (see FIG. 5C). The results indicate that although sCD4Fc and m36h1Fc exhibited stronger binding than monomeric sCD4 and m36, respectively, their binding strengths were much lower than that of m36L2CD4Fc.

Figure 5D:
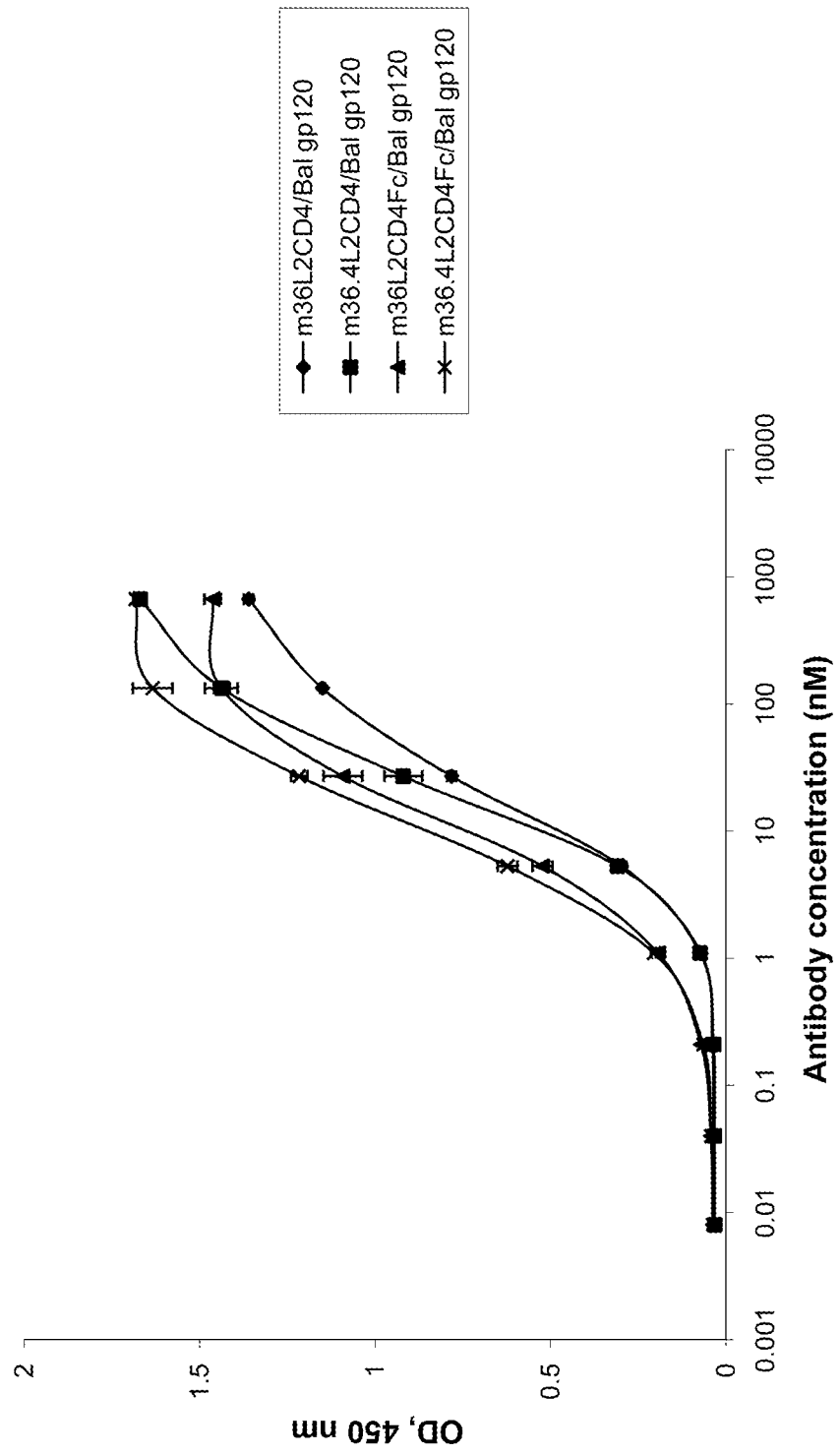

Similar m36.4 fusion constructs were created by replacing m36 with m36.4. The resultant proteins, m36.4L2CD4 and m36.4L2CD4Fc showed slightly higher binding to gp120$_{Bal}$ than their parent counterparts, respectively (see FIG. 5D).

EXAMPLE 3

This example demonstrates the potency and breadth of HIV-1 neutralization by the inventive fusion proteins.

Figure 6C:
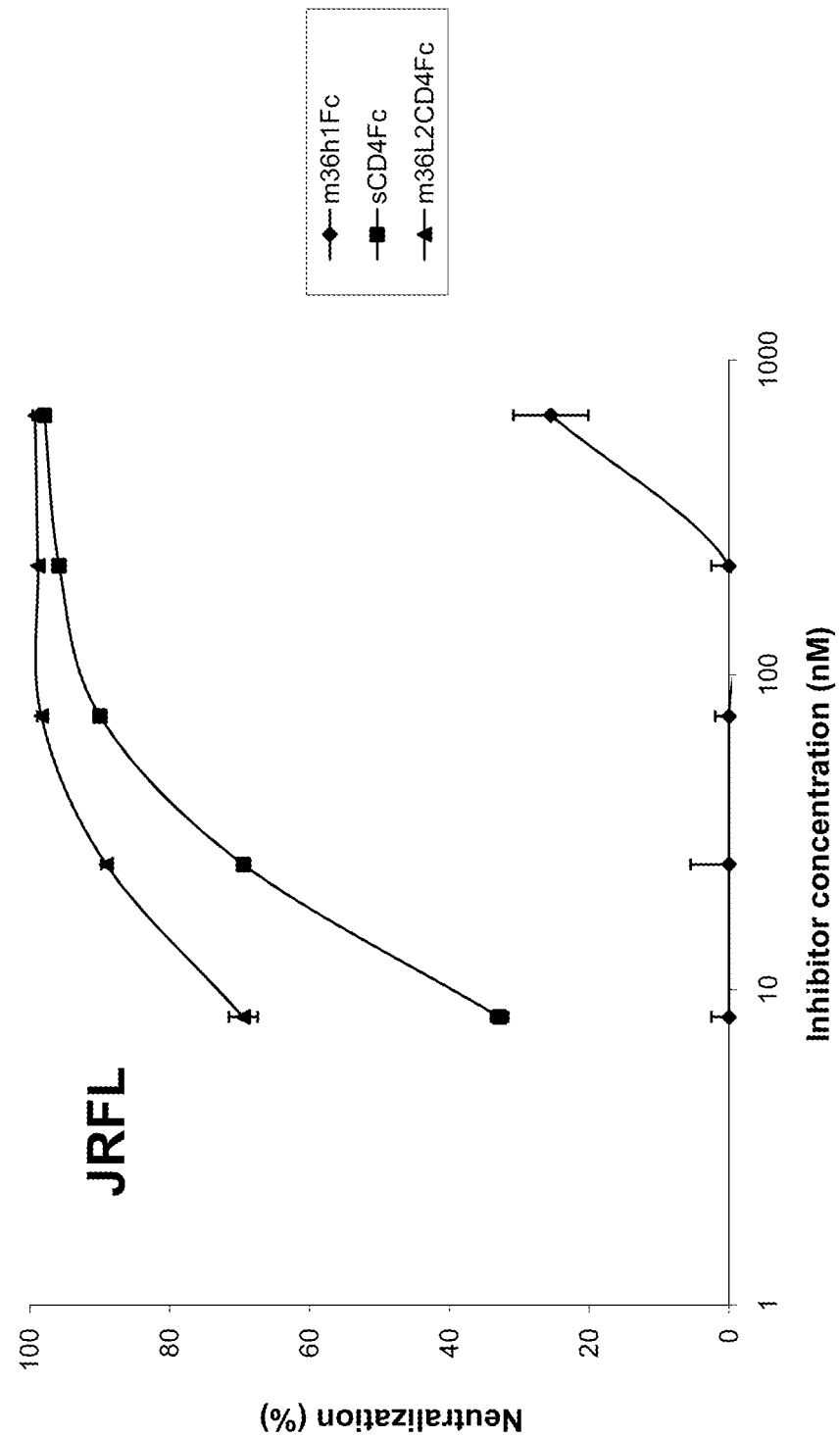
FIG. 6 provides graphs illustrating dose-dependent inhibition of 92UG037.8 (FIG. 6A), Bal (FIG. 6B), JRFL (FIG. 6C), and 89.6 (FIG. 6D) by m36h1Fc, sCD4Fc, and m36L2CD4Fc. Inhibitor concentration (nM) is on the x-axis and percent neutralization is on the y-axis.

Cell line-based pseudovirus neutralization assays were conducted with 14 HIV-1 isolates representing clade A-E. Although there was an increase in molecular size, all the fusion proteins were more effective than m36 against almost all the isolates tested, having IC$_{50}$s and IC$_{90}$s on average several fold lower than those of m36 (see Tables 1A, 1B, 2A, and 2B). m36L2CD4Fc and m36.4L2CD4Fc exhibited even more potent neutralization than m36L2CD4 and m36.4L2CD4 against some isolates while a slight decrease in potency was observed with GXC-44 (clade C) for m36L2CD4Fc and with 92UG037.8 (clade A) for m36.4L2CD4Fc. Overall, no significant difference in potency was seen between m36L2CD4 and m36.4L2CD4, and between m36L2CD4Fc and m36.4L2CD4Fc, whereas some isolates could be slightly more efficiently neutralized by one eAd and others could be better affected by the other eAd. Of particular note, GXE (clade E), which was insensitive to m36, could be relatively potently neutralized by the fusion proteins suggesting that the neutralizing activities of the fusion proteins could be broader than that of m36.

m36L2CD4Fc was compared to m36h1Fc and sCD4Fc in neutralization against four isolates (FIG. 6). m36h1Fc did not inhibit or poorly inhibited three isolates (92UG037.8, Bal, and JRFL), while it efficiently neutralized 89.6. sCD4Fc was highly efficient in neutralizing all the isolates with IC$_{50}$s less than 40 nM. As expected, even more potent neutralization occurred with m36L2CD4Fc; the IC$_{50}$s with 92UG037.8, Bal, and 89.6 were at least 9-fold lower than those for sCD4Fc; about 2 fold decrease in IC$_{50}$ with JRFL was also observed for m36L2CD4Fc compared to that for sCD4Fc. These results confirm that the increased potency of m36 and m36.4 after fusion with sCD4 or sCD4-Fc was attributed mainly to the synergistic and/or avidity effects between the eAd and sCD4 but not due to the dimerization of the eAd or sCD4.

EXAMPLE 4

This example describes the generation of a mutagenesis library of single-domain CD4 (D1).

A phage-displayed library (about 10$^9$ members) of D1 (SEQ ID NO: 12) was constructed by random mutagenesis. Four hydrophobic residues of D1 (residues 5L, 76I, 96L, and 98F of SEQ ID NO: 12), which strongly interact with the second domain (D2) according to a crystallographic analysis, were randomly mutated using degenerate primers:

D1mF sense:

(SEQ ID NO: 76)
5'-CGCTACCGTGGCCCAGGCGGCCAAGAAGGTGGTGNNSGGCAAGAAG

GGCGACACC-3'

D1mR1 antisense:

(SEQ ID NO: 77)
5'-GTGGTGGCCGGCCTGGCCGCCWNNCACWNNCAGCTGCACCTCCTCC

TTCTGGTCCTCCACCTCGCAGATGTA-3'

-continued

D1mR2 antisense:
(SEQ ID NO: 78)
5'-CTCGCAGATGTAGGTGTCGCTGTCCTCWNNCTTCAGGTTCTTGATG
ATCAG-3'

D1 gene fragment was first amplified by PCR with a D1D2-encoding plasmid as a template and primers D1mF and D1mR2. The PCR product was gel-purified and used as a template for amplification of full-length D1 gene by using primers D1mF and D1mR1.

To introduce point mutations in other positions, random DNA mutagenesis was performed with the purified full-length D1 gene as a template, primers D1mF and D1mR1, and the Gene-Morph PCR Mutagenesis Kit (Stratagene, La Jolla, Calif.) according to the manufacturer's instructions. The PCR products were gel-purified, digested with SfiI, and gel-purified again. The purified fragments then were cloned into phagemid pComb3X linearized by SfiI. A phage library was prepared by electroporation of *E. coli* strain TG1 electroporation-competent cells (Stratagene, La Jolla, Calif.) with desalted and concentrated ligation, as described in Chen et al., *J. Mol. Biol.*, 382: 779-789 (2008).

The library was used for selection of D1 mutants against HIV-1 antigens coated on 96-well plates as described in Feng et al., *Mol. Cancer Ther.*, 5: 114-120 (2006). The library was panned sequentially against two different envelope proteins (Envs) from clade-β isolates, gp140SC and gp140MS (see Chen et al., *Antiviral Res.*, 88: 107-115 (2010); and Garlick et al., *AIDS Res. Hum. Retroviruses*, 6: 465-479 (1990), respectively) in order that enriched D1 mutants could preserve cross-reactivity. For sequential panning, 200 ng, 100 ng, and 20 ng of $gp140_{SC}$, $gp140_{MS}$, and $gp140_{SC}$ were used in the first, second and third rounds, respectively.

To identify individual mutants that specifically bound to all antigens and were soluble in the *E. coli* periplasm, clones were randomly selected after three rounds of panning and subjected to screening by soluble expression-based monoclonal ELISA (semELISA). Sequencing of 40 highest affinity binders revealed that they represented 19 different clones. Notably, a majority (89%) of the mutants retained hydrophobic residues in positions 5 and 96 (where isoleucine dominated), while 58% and 68%, respectively, of the mutants contained hydrophobic residues in positions 76 and 98.

Two clones, designated mD1 and mD2, were chosen for further characterization because of their relatively high yields (about 0.5 mg/L and about 0.75 mg/L, respectively) from the soluble fraction of *E. coli* (strain HB2151) periplasm and their high affinity to all gp140s tested.

EXAMPLE 5

This example describes the characterization of mD1 and mD2.

The mD1 and mD2 mutants identified in Example 4 were cloned into a mammalian expression vector in order to compare the mutants with a recombinant soluble CD4 containing the first two domains (D1D2), which was produced from mammalian cell culture (expressed in *E. coli* as an insoluble inclusion body protein). To clone mD1 and mD2 for mammalian expression, the gene fragments were PCR amplified with their bacterial expression plasmids as templates and primer combinations D1-49F/D1-49R and D1-53F/D1-53R, respectively.

D1-49F sense:
(SEQ NO: 79)
5'-TGACGCGGCCCAGCCGGCCAAGAAGGTGGTGATCGGC-3'

D1-49R (antisense):
(SEQ ID NO: 80)
5'-CGGGTTTAAACTCAGTGGTGGTGGTGGTGGCCTAGCACTATCA
GCTG-3'

D1-53F (sense):
(SEQ ID NO: 81)
5'-TGACGCGGCCCAGCCGGCCAAGAAGGTGGTGTACGGC-3'

D1-53R (antisense):
(SEQ ID NO: 82)
5'-CGGGTTTAAACTCAGTGGTGGTGGTGGTGGCCTACCACTACCA
GCTG-3'

The PCR products were gel-purified, digested with SfiI and PmeI, cloned into a mammalian expression vector (pSecTagB-Fc), expressed in 293 cells, and purified from the cell culture supernatents. On a reducing SDS-PAGE gel, the mutants had apparent molecular weights (aMWs) of about 16 kDa, which were beyond their calculated MWs (cMWs) (12.040 and 12.061 kDa, respectively, including the hexahistidine tag). mD1 and mD2 were uniformly monomeric in PBS at pH 7.4 with aMWs similar to their cMWs as determined by size-exclusion chromatography. D1D2 also was monomeric but it was not eluted as a single peak.

The binding characteristics of mD1, mD2, and D1D2 with HIV-1 gp140 were assessed by surface plasmon resonance (SPR) analysis on Biacore X100 (GE Healthcare) using single-cycle approach according to the manufacture's instructions. Briefly, purified HIV-1 gp140 was diluted in sodium acetate (pH 5.0) and immobilized directly onto a CM5 sensor chip with standard amine coupling method. The reference cell was injected with N-hydroxysuccinimide/1-ethyl-3-(3-dimethyaminopropy) carbodiimide and ethanolamine without injection of gp140. The proteins were diluted in running buffer HBS-EP (100 mM HEPES, pH 7.4, 1.5 M NaCl, 30 mM EDTA, 0.5% surfactant 20). All analytes were tested at 500 nM, 100 nM, 20 nM, 4 nM, and 0.8 nM concentrations. The kinetic constants were calculated from the sensorgrams fitted with the monovalent binding model of BiacoreX100 Evaluation software 2.0.

The results from SPR showed that both D1 mutants bound to $gp140_{Con-s}$, which was a consensus gp140 designed by aligning >1,000 sequences of group M (see Liao et al., *Virology*, 353: 268-282 (2006)), with comparable pM affinity ($KD=1.6\times10^{10}$), which is about 47-fold higher than that ($KD=7.8\times10^9$ M) of D1D2. The mutants had much faster (about 30-fold) association rates and relatively slower (about 2-fold) dissociation rates.

To assess cross-reactivity and confirm the high affinity of mD1 and mD2, ELISAs were performed with two additional gp140s ($gp140_{CH12.0544.2}$ and $gp140_{SC}$) from clade B isolates. Bound D1D2 and D1 mutants were detected by HRP-conjugated anti-hexahistidine tag antibody (Sigma-Aldrich, St. Louis, Mo.). The half-maximal binding ($EC_{50}$) was calculated by fitting the data to the Langmuir adsorption isotherm. As expected, both mutants were cross-reactive against all three gp140s and in all cases, had $EC_{50}$s about 10-fold lower than those of D1D2.

EXAMPLE 6

This example describes the generation of fusion proteins comprising mD1 or mD2.

To determine whether the increased affinity of the D1 mutants is due to their decreased molecular size or mutation-induced structural refinement or both, two fusion proteins of mD1 with human IgG1 CH2 domain, one (mD1-CH2) without a linker and the other (mD1L3CH2) with a polypeptide linker composed of three repeats of $G_4S$ motif (SEQ ID NO: 38), were prepared.

To construct the mD1-CH2 fusion protein without a linker, mD1 fragment was PCR amplified by using primers D1-49F and D1R4. CH2 fragment was amplified with an IgG1-encoding plasmid as a template and primers CH2F1 and CH2R.

CH2F1 (sense):
(SEQ ID NO: 83)
5'-GCACCTGAACTCCTGGGG-3'

CH2F2 (sense):
(SEQ ID NO: 84)
TCAGGCGGAGGTGGCTCTGGCGGTGGCGGATCAGCACCTGAACTCCTGGGG-3'

CH2R (antisense):
(SEQ ID NO: 85)
5'-CGGGTTTAAACTCAGTGGTGGTGGTGGTGGTGTTTGGCTTTGGAGATGGT-3' mD1 was joined to CH2 by overlapping PCR performed in a volume of 50 μL by using both templates (in the same molarities) for 7 cycles in the absence of primers and 15 additional cycles in the presence of primers (500 pM of D1-49F and CH2R). In the same way, mD1-CH2 fusion protein with three repeats of G4S motif as a linker (mD1-L3-CH2) was constructed except for the use of primer combinations D1-49F/D1R5 and CH2F2/CH2R for amplification of mD1 and CH2 fragments, respectively. The resultant products appended with SfiI and PmeI restriction sites on both sides was digested and cloned into pSecTagB-Fc.

In the human IgG1, CH2 is independently folded. Isolated CH2 was solubly expressed in *E. coli* with high yield and had a MW of about 13 kDa, similar with that of the second domain of CD4, D2 (about 10 kDa). Therefore, the fusion proteins could mimic D1D2 in molecular size and shape.

The associate rate constants of mD1-CH2 and mD1-L3-CH2 ($Ka=6.1\times10^4$ and $5.5\times10^4$ Ms-1, respectively) were decreased by about 80-fold compared to that ($Ka=4.8\times10^6$ Ms-1) of mD1 as measured by SPR. The fusion proteins had the same dissociation rates constant ($Kd=9.0\times10^{-4}$ s$^{-1}$) comparable with that ($Kd=7.7\times10^{-4}$ s$^{-1}$) of mD1 and slightly lower than that ($Kd=1.3\times10^{-3}$ s$^{-1}$) of D1D2.

These results suggest that the improved binding kinetics of mD1 compared to D1D2 is mostly due to decreased molecular size although possible structural adjustments induced by the mutations could also contribute.

EXAMPLE 7

This example demonstrates that the D1 mutants maintain the functional activity of full-length CD4.

CD4 induces conformational changes in gp120 leading to exposure of CD4-inducible (CD4i) epitopes. To determine whether the D1 mutants induce such conformational changes, two CD4i antibody-based fusion proteins, m9Fc (see Zhang et al., *J. Mol. Biol.*, 35: 209-219 (2004)) and m36h1Fc (see Chen et al., *Proc. Natl. Acad. Sci. USA*, 105: 17121-17126 (2008)), were tested for binding to gp140Con-s in the absence or presence of mD1, mD2, or D1D2.

As expected, binding of the two CD4i antibody-based fusion proteins to gp140Con-s was dramatically increased in the presence of the D1 mutants. The increase in binding was significantly higher (about 3-fold) with the D1 mutants versus D1D2.

EXAMPLE 8

This example demonstrates that the D1 mutants can neutralize HIV-1 and sensitize the virus for neutralization by CD4i antibodies.

To determine the potency and breadth of HIV-1 neutralization by the D1 mutants, viruses pseudotyped with Envs from HIV-1 isolates representing clades A-E and using either CCR5 (R5) or CXCR4 (X4) or both (R5×4) as a coreceptor were included. Pseudoviruses were derived from 293T cells and a neutralization assay was performed in duplicate using HOS-CD4-CCR5 (for all R5 and dual tropic viruses) or HOS-CD4-CXCR4 cell lines as described in Chen et al., *Proc. Natl. Acad. Sci. USA*, 105: 17121-17126 (2008)). Luminescence was measured 48 hours post-infection and the percentage neutralization was calculated by the following formula: (1−average RLU of inhibitor-containing wells/average RLU or virus-only wells)×100. IC50 and IC90 of neutralization were assigned for the inhibitor concentration at which 50% and 90% neutralization were observed, respectively.

Of the 13 isolates tested, 8 were significantly better neutralized by mD1 and mD2 than by D1D2. Four (Bal, JRFL, IIIB and NL4-3) were neutralized with the same potency. Only one (GXC-44) showed reduced sensitivity to the D1 mutants (see Table 3).

The D1 mutants had on average about two-fold lower arithmetic and geometric means of both IC50s and IC90s compared to D1D2. The mutants also were more potent than Fab b12 (see Roben et al., *J. Virol.*, 68: 4821-4828 (1994)), a well-characterized broadly neutralizing monoclonal antibody (bnmAb) targeting the CD4-binding site on gp120, which neutralized mainly clade-β isolates. IgG1 m102.4 (see Zhu et al., *J. Infect. Dis.*, 197: 846-853 (2008)), a control antibody specific to Nipah and Hendra viruses, did not inhibit any of the viruses.

The synergistic effect of a combination of sCD4 and CD4i antibodies on HIV-1 neutralization has been described previously. The major mechanism of action is that sCD4 enhances the exposure of the antibody epitopes and therefore, the antibodies could better bind the Env. To find out whether there is synergy between the D1 mutants and CD4i antibodies, pseudoviruses were pre-incubated with a CD4i antibody, m36h1Fc, in the presence of low concentration of mD1, mD2, or D1D2. m36h1Fc alone at up to 1000 nM or IgG1 m102.4 combined with mD1 or mD2 at 2 nM exhibited very low or no neutralizing activity. As expected, pre-incubation of Bal with both m36h1Fc and the D1 mutants resulted in a dramatic increase in neutralization.

EXAMPLE 9

This example demonstrates the generation of fusion proteins comprising the D1 mutants and gp120.

gp120-sCD4 fusion proteins are potentially useful as vaccine immunogens because of the highly conserved neutralizing epitopes on gp120 exposed in the CD4-bound state. To assess the degree to which the D1 mutants could stabilize gp120 in this state, gp120$_{SC}$-mD2 and two control proteins, gp120$_{SC}$-D1D2 and gp120$_{SC}$, were prepared and their binding to CD4i antibodies was measured.

The following primers were used:

SCF (sense):
(SEQ ID NO: 107)
5'-TGACGCGGCCCAGCCGGCCGAGGTGGTGCTGGGCAAC-3'

SCR (antisense):
(SEQ ID NO: 108)
5'-TGAACCGCCTCCACCGCTTCCTCCTCCTCCGGATCCTCCTCCGCCGGATCCTCCTCCCCTCGATCTTCACCACCTT-3'

SCD1F (sense):
(SEQ ID NO: 109)
5'-GGTGGAGGCGGTTCAAAGAAGGTGGTGTACGGC-3'

SCD12F (sense):
(SEQ ID NO: 110)
5'-GGTGGAGGCGGTTCAAAGAAGGTGGTGCTGGGC-3'

SCD12R (antisense):
(SEQ ID NO: 111)
5'-CGGGTTTAAACTCAGTGGTGGTGGTGGTGGGCCAGCACCACGATGTC-3'

SCR1 (antisense):
(SEQ ID NO: 112)
5'-CGGGTTTAAACTCAGTGGTGGTGGTGGTGGTGCTCGATCTTCACCACCTT-3'

D1-53R (antisense):
(SEQ ID NO: 82)
5'-CGGGTTTAAACTCAGTGGTGGTGGTGGTGGCCTACCACTACCAGCTG-3'

For cloning of gp120$_{SC}$-mD2, gp120$_{SC}$ and mD2 gene fragments were PCR amplified by using primer pairs SCF/SCR and SCD1F/D1-53R. gp120$_{SC}$ was joined to mD2 by overlapping PCR using primers SCF/D1-53R. The resultant product was digested with SfiI and PmeI, and cloned into pSecTagB.

In the same way gp120$_{SC}$-D1D2 was constructed except the use of primers SCD12F/SCD12R for amplification of D1D2 and SCF/SCD12R for overlapping PCR. To generate gp120$_{SC}$, the gene fragment was amplified by PCR with primers SCF/SCR1, digested with SfiI and PmeI, and cloned into pSecTagB.

gp120$_{SC}$-mD2, gp120$_{SC}$-D1D2, and gp120$_{SC}$ were expressed in 293 cells and purified from the cell culture supernatants with yields of about 2.1, 2.4 and 1.7 mg/L, respectively. The proteins ran on a reducing SDS-PAGE gel as relatively broad bands due to glycosylation. Notably, m36h1Fc bound to gp120$_{SC}$-mD2 significantly stronger (about 6-fold) than to gp120$_{SC}$-D1D2. Another CD4i antibody, m9Fc, also bound to 120$_{SC}$-mD2 slightly better than to gp120$_{SC}$-D1D2.

These results suggest that D1 mutants (e.g., mD2) can induce and stabilize structural rearrangements in gp120 more efficiently than D1D2.

EXAMPLE 10

This example demonstrates the generation of fusion proteins comprising the m36.4 eAd and D1 mutant.

In an attempt to increase the neutralization potency of mD1, three fusion proteins of mD1 were produced with a CD4i eAd, m36.4, for synergistic effects by using three (m36.4L3D1), six (m36.4L6D1) and nine (m36.4L9D1) repeats of G4S motif as a linker, respectively.

```
m36.4F (sense):
                                         (SEQ ID NO: 86)
5'-TACCGTGGCCCAGGCGGCCCAGGTGCAGCTGGTGCAG-3' m36.4R1 (antisense):
                                         (SEQ ID NO: 87)
5'-ACTTCCCCCGCCTCCGCTGCCACCCCCTCCTGAGGAGACGGTGA

C-3'

D1F1 (sense):
                                         (SEQ ID NO: 88)
5'-AGCGGAGGCGGGGGAAGTGGCGGTGGAGGGAGCAAGAAGGTGGTGA

TC-3'

D1R (antisense):
                                         (SEQ ID NO: 89)
5'-GTGGTGGCCGGCCTGGCCGCCTAGCACTATCAG-3' m36.4R2 (antisense):
                                         (SEQ ID NO: 90)
5'-TGAACCGCCTCCACCGCTCCCTCCACCGCCACTTCCCCCGCCACCG

CTGCCACCCCCTCCTGAGGAGACGGTGAC-3'

D1F2 (sense):
                                         (SEQ ID NO: 91)
5'-AGCGGTGGAGGCGGTTCAGGCGGAGGTGGCTCTGGCGGTGGCGGAT

CAAAGAAGGTGGTGATC-3' m36.4R3 (antisense):
                                         (SEQ ID NO: 92)
5'-AGAGCCACCTCCGCCTGAACCGCCTCCACCGCTCCCTCCACCGCCA

CTTCCCCCGCCTCCGCTGCCACCCCCTCCTGAGGAGACGGTGAC-3'

D1F3 (sense):
                                         (SEQ ID NO: 93)
5'-TCAGGCGGAGGTGGCTCTGGCGGTGGCGGATCAGGGGGCGGAGGTA

GTGGGGGAGGGGGATCGGGTGGGGGAGGCAGCAAGAAGGTGGTGATC-3'
```

For cloning of m36.4L3D1, m36.4 and mD1 were PCR amplified by using primer pairs m36.4F/m36.4R1 and D1F1/D1R. mD1 was joined to m36.4 by overlapping PCR using primers m36.4F/D1R. The resultant product was digested with SfiI and cloned into pComb3X. In the same way, m36.4L6D1 and m36.4L9D1 were constructed except the use of primer pairs m36.4F/m36.4R2 (for amplification of m36.4 for m36.4L6D1), D1F2/D1R (for amplification of mD1 for m36.4L6D1), m36.4F/m36.4R3 (for amplification of m36.4 for m36.4L9D1), and D1F3/D1R (for amplification of mD1 for m36.4L9D1).

The resultant products were gel-purified, digested with SfiI and ApaI, and then cloned into pSecTagB. The fusion proteins were expressed in *E. coli* strain HB2151, and the proteins were purified from the *E. coli* periplasm fraction with yield of about 0.75 mg/L.

On an ELISA assay, the fusion proteins bound to $gp120_{Bal}$ with $EC_{50}$s much lower than those of m36.4 or mD1 alone or m36.4 plus mD1, suggesting synergistic and/or avidity effects. The results also showed that a long linker could confer stronger binding likely due to the higher flexibility it provided.

To determine whether and how much avidity effect could be achieved through dimerization, human IgG1 CH3 domain was used. Again, three (D1L3CH3), six (D1L6CH3) and nine (D1L9CH3) repeats of $G_4S$ motif were used explore the effects of linker length.

D1F4 (sense):
(SEQ ID NO: 94)
5'-TACCGTGGCCCAGGCGGCCAAGAAGGTGGTGATC-3'

D1R1 (antisense):
(SEQ ID NO: 95)
5'-ACTTCCCCCGCCTCCGCTGCCACCCCCTCCGCCTAGCACTATCAG-3'

CH3F1 (sense):
(SEQ ID NO: 96)
5'-AGCGGAGGCGGGGAAGTGGCGGTGGAGGGAGCGGGCAGCCCCGAGAA-3'

CH3R1 (antisense):
(SEQ ID NO: 97)
5'-GTGGTGGCCGGCCTGGCCTTTACCCGGAGACAG-3'

D1R2 (antisense):
(SEQ ID NO: 98)
5'-TGAACCGCCTCCACCGCTCCCTCCACCGCCACTTCCCCCGCCACCGCTGCCACCCCCTCCGCCTAGCACTATCAG-3'

CH3F2 (sense):
(SEQ ID NO: 99)
5'-AGCGGTGGAGGCGGTTCAGGCGGAGGTGGCTCTGGCGGTGGCGGATCAGGGCAGCCCCGAGAA-3'

D1R3 (antisense):
(SEQ ID NO: 100)
5'-AGAGCCACCTCCGCCTGAACCGCCTCCACCGCTCCCTCCACCGCCACTTCCCCCGCCTCCGCTGCCACCCCCTCCGCCTAGCACTATCAG-3'

CH3F3 (sense):
(SEQ ID NO: 101)
5'-TCAGGCGGAGGTGGCTCTGGCGGTGGCGGATCAGGGGGCGGAGGTAGTGGGGGAGGGGATCGGGTGGGGAGGCAGCGGGCAGCCCCGAGAA-3' mdcR (antisense):
(SEQ ID NO: 102)
5'-CGGGTTTAAACTCAGTGGTGGTGGTGGTGTTTACCCGGAGACAG-3' mF (sense):
(SEQ ID NO: 103)
5'-TGACGCGGCCCAGCCGGCCCAGGTGCAGCTGGTGCAG-3' mdR (antisense):
(SEQ ID NO: 104)
5'-GCCTAGCACTATCAGCTG-3' mdF (sense):
(SEQ ID NO: 105)
5'-CAGCTGATAGTGCTAGGC-3' mdR1 (antisense):
(SEQ ID NO: 106)
5'-TTTGTCGGGCCCGCCTAGCACTATCAGCTG-3'

To generate D1L3CH3, mD1 and CH3 were amplified by PCR (primer pairs D1F4/D1R1 and CH3F1/CH3R1, respectively). mD1 and CH3 fragments were overlapped by using PCR with primers D1F4 and CH3R1. The resultant product was used as a template for extension PCR (primers D1-49F/mdcR) to attach SfiI and PmeI restriction sites at both ends. The extension PCR product was purified, digested with SfiI and PmeI, and then cloned into pSecTagB.

In the same way, D1L6CH3 and D1L9CH3 were cloned except the use of primer combinations D1F4/D1R2 (for amplification of mD1 for D1L6CH3), CH3F2/CH3R1 (for amplification of CH3 for D1L6CH3), D I F4/D1R3 (for amplification of mD1 for D1L9CH3), and CH3F3/CH3R1 (for amplification of CH3 for D1L9CH3).

To make m36.4D1CH3, m36.4L3D1 fragment was PCR amplified by using primers mF/mdR. CH3 was amplified with primers mdF/mdcR. CH3 was joined to the 3' end of m36.4L3D1 by overlapping PCR (primers mF/mdcR). The product was purified, digested with SfiI and PmeI, and cloned into pSecTagB.

For cloning of m36.4D1Fc, m36.4L3D1 was PCR amplified with primers mF/mdR1. The resultant product was gel-purified, digested with SfiI and ApaI, and then cloned into pSecTagB-Fc.

The three m36.4-mD1 fusion proteins were expressed and purified from the shaking 293 free style cell culture supernatants with yields of about 9.1, 5.6 and 0.34 mg/L, respectively. Their ELISA binding activities with gp140$_{Cons}$ were increased by >10-fold compared to monomeric mD1, suggesting the avidity effects. In contrast to the fusion proteins of m36.4-mD1, the binding of mD1-CH3 fusion proteins was not significantly affected by linker length.

To explore the possibility of combining both synergistic and avidity effects observed in m36.4-mD1 fusion proteins and avidity effects from mD1 dimerization, two fusion proteins were generated by joining m36.4L3D1 to either IgG1 CH3 (m36.4D1CH3) or Fc (m36.4D1Fc). The fusion proteins were expressed and purified from the shaking 293 free style cell culture supernatants with yields of about 1.3 and 15 mg/L, respectively. Both fusion proteins bound to gp120$_{Bal}$ with higher activity than m36.4L3D1, but m36.4D1Fc showed weaker binding than m36.4D1CH3.

The neutralizing potency of the fusion proteins was assessed by using several HIV-1 isolates from different clades. As expected, all m36.4-mD1 fusion proteins neutralized the four tested isolates better than either mD1 or m36.4 alone and comparably with m36.4 plus D1D2, while no obvious difference in potency was seen among the fusion proteins (see Table 4).

Even greater increase in neutralizing activity was observed with the mD1-CH3 fusion proteins (see Table 5). Their potency was comparable although with different linker length. Unexpectedly, m36.4D1CH3 and m36.4D1Fc showed comparable or diminished neutralization compared to m36.4L3D1 (see Table 6) suggesting that the further increase in avidity effects may be compromised by their great increase in molecular weight.

EXAMPLE 11

This example demonstrates the generation of an additional construct comprising the m36.4 eAd and D1 mutant.

The following primers were used in the preparation of the fusion proteins:

m36.4L2 (sense):
(SEQ ID NO: 113)
5'-CTTACAGATGCCAGATGTCAGGTGCAGCTGGTGCAG-3' m36.4L4 (antisense):
(SEQ ID NO: 114)
5'-AGAGCCACCTCCGCCTGAACCGCCTCCACCTGAGGAGACGGTGACCAG-3'

CLF (sense):
(SEQ ID NO: 115)
5'-TCAGGCGGAGGTGGCTCTGGCGGTGGCGGATCACGAACTGTGGCTGCACCA-3'

-continued

D1L2 (sense):
(SEQ ID NO: 116)
5'-ACTACAGGTGTCCACTCCAAGAAGGTGGTGATCGGC-3'

D1L4 (antisense):
(SEQ ID NO: 117)
5'-CCTTGGAGCTCGATCCGCCACCGCCAGAGCCACCTCCGCCTGAACC
GCCTCCACCGCCTAGCACTATCAGCTG-3'

HleaderF (sense):
(SEQ ID NO: 118)
5'-TAATTCTCTAGAGCCGCCACCATG-3'

CH3R (antisense):
(SEQ ID NO: 119)
5'-AGAGCCACCTCCGCCTGAACCGCCTCCACCTTTACCCGGAGACAGG
GA-3'

D1F (sense):
(SEQ ID NO: 120)
5'-TCAGGCGGAGGTGGCTCTGGCGGTGGCGGATCAAAGAAGGTGGTGA
TCGGC-3'

D1R (antisense):
(SEQ ID NO: 121)
5'-CCGTCGCACTCAGCCTAGCACTATCAGCTG-3'

AAAF (sense):
(SEQ ID NO: 122)
5'-TGAGTGCGACGGCCGGCA-3'

AAAR (antisense):
(SEQ ID NO: 123)
5'-CCCGAGGTCGACGCTCTC-3'

CLR (antisense):
(SEQ ID NO: 124)
5'-ACTTCCCCGCCACCGCTGCCACCCCCTCCACACTCTCCCCTGTTG
AA-3'

CLD1F (sense):
(SEQ ID NO: 125)
5'-AGCGGTGGCGGGGGAAGTGGCGGTGGAGGGAGCAAGAAGGTGGTGA
TCGGC-3'

D1RR (antisense):
(SEQ ID NO: 126)
5'-ATCAATGAATTCATTAGCCTAGCACTATCAGCTG-3' bnIgG20L1 (sense):
(SEQ ID NO: 127)
5'-GTGTAAGCTTACCATGGGTGTGCCCACTCAGGTCCTGGGGTTGCT
G-3' bnIgG20L2 (sense):
(SEQ ID NO: 128)
5'-CTTACAGATGCCAGATGTGATGTTGTGATGACTCAG-3' bnIgG20L3 (antisense):
(SEQ ID NO: 129)
5'-ACATCTGGCATCTGTAAGCCACAGCAGCAGCAACCCCAGGAC-3' bnIgG20L4 (antisense):
(SEQ ID NO: 130)
5'-GTGTGAATTCATTAACACTCTCCCCTGTTGAA-3' bnIgG20H1 (sense):
(SEQ ID NO: 131)
5'-GTGTTCTAGAGCCGCCACCATGGAATGGAGCTGGGTCTTTCTCTT
C-3' bnIgG20H3 (antisense):
(SEQ ID NO: 132)
5'-GGAGTGGACACCTGTAGTTACTGACAGGAAGAAGAGAAAGAC-3'

To fuse mD1 to the N terminus of the human IgG1 heavy chain constant region, the mD1 gene fragment was PCR-amplified with an mD1-encoding plasmid as a template and primers D1L2 and D1L4. The heavy chain leader peptide gene fragment (Hleader) was amplified with primers bnIgG20H1 and bnIgG20H3. mD1 was joined to Hleader by overlapping PCR performed in a volume of 50 µL by using both templates (in the same molarities) for 7 cycles in the absence of primers and 15 additional cycles in the presence of primers (500 pM of bnIgG20H1 and D1L4). The product was digested with XbaI and SacI, and cloned into vector pDR12.

To fuse m36.4 to the N terminus of the human IgG1 light chain constant region, m36.4 was amplified by PCR with primers m36.4L2 and m36.4L4. The light chain leader peptide gene fragment (Lleader) was PCR amplified with primers bnIgG20L1 and bnIgG20L3. The human IgG1 kappa light chain constant region (CK) was obtained by using primers CLF and bnIgG20L4. Lleader was linked to m36.4 and CK by overlapping PCR with primers bnIgG20L1 and bnIgG20L4 as described above. The Lleader-m36.4-CK fragment was then digested with EcoRI and HindIII, and cloned into the pDR12 vector containing mD1. The resultant construct was designated as m36.4D1IgG1 and used as a template for further cloning.

To fuse another mD1 to the C terminus of human IgG1 heavy chain constant region, the full-length heavy chain of m36.4D1IgG1 (Hleader-mD1-Fc) was PCR amplified with m36.4D1IgG1 plasmid as a template and primer pair HleaderF/CH3R. mD1 and the polyA tail for translation were amplified by using primer pairs D1F/D1R and AAAF/AAAR, respectively. Hleader-mD1-Fc was then fused to the mD1 and the polyA tail by overlapping PCR with primers HleaderF and AAAR. The product was digested with XbaI and SalI, and cloned into pDR12. The new construct was designated as m36.4D1IgG1D1 and used as a template for further cloning.

To fuse another mD1 to the C terminus of CK, the m36.4-CK fragment was PCR amplified with m36.4D1IgG1 as a template and primer pair bnIgG20L1/CLR. mD1 was amplified with primers CLD1F and D1RR. m36.4-CK was fused with mD1 by overlapping PCR with primers bnIgG20L1 and D1RR. The product was digested with EcoRI and HindIII, and cloned into m36.4D1IgG1D1. The nucleic acid sequence and the amino acid sequence of the heavy chain fusion protein are SEQ ID NOs: 133 and 134, respectively. The nucleic acid sequence and the amino acid sequence of the light chain fusion protein are SEQ ID NOs: 135 and 136, respectively.

The resultant construct, which contains mD1 at the N and C terminuses of heavy chain and the C terminus of light chain, respectively, and m36.4 at the N terminus of light chain, was designated mD1m36.4Fc6. The structure of mD1m36.4Fc6, which is a bispecific octavalent IgG-like fusion protein of mD1 with m36.4, is depicted in FIG. 8.

mD1m36.4Fc6 was expressed and purified from 293 free style cell culture supernatant with yield of about 1 mg/L. Neutralization potency and breath was determined by using viruses pseudotyped with Envs from R5 HIV-1 isolates representing clades A, B, and C.

As shown in Table 7, mD1m36.4Fc6 potently neutralized all isolates tested. In comparison with IgG1 VRC01, which is one of the most potent and broadly cross-reactive human monoclonal antibodies against HIV-1, mD1m36.4Fc6 had significantly (two-four fold) lower $IC_{50}$s or $IC_{90}$s with three isolates (92UG037.8, Bal and JRFL). mD1m36.4Fc6 neutralized GXC with both $IC_{50}$ and $IC_{90}$ lower than those of IgG1 VRC01.

EXAMPLE 12

This example demonstrates the further characterization of the D1 mutants.

The solubility of mD1, mD2, and D1D2 was determined by the ultrafiltration method. mD1 and mD2 were concentrated up to 135.2 and 92.6 mg/mL, respectively, without visible precipitation after high-speed centrifugation. Higher concentrations were not tested because of the large amount of protein required. In contrast, precipitation was observed with D1D2, and its concentration in the supernatant after high-speed centrifugation was 49.9 mg/mL. The supernatants of the three samples were kept at 4° C. for 5 days without precipitation suggesting that they remain soluble at those concentrations and conditions.

The secondary structure and thermal stability of mD1, mD2, and D1D2 were determined by circular dichroism (CD) spectroscopy. The purified proteins were dissolved in PBS at the final concentration of 0.33 mg/mL, and the CD spectra were recorded on AVIV Model 202 CD Spectrometer (Aviv Biomedical). Wavelength spectra were recorded at 25° C. using a 0.1-cm path-length cuvette for native structure measurements. Thermal stability was measured at 216 nm by recording the CD signal in the temperature range of 25-90° C. with heating rate 1° C./min. The temperature was recorded with an external probe sensor and the temperature inside the microcuvette was calculated by calibration; it was about 2-3° C. (range from 1.9 to 3.8° C. for temperatures from 20 to 80° C.) lower than the one measured by the external sensor. After heating, wavelength spectra were recorded at 90° C.

The D1D2 unfolding started at about 46° C. and was completed at about 67° C. with a temperature of 50% unfolding ($T_m$) of about 58.5° C. The measurement was terminated at 70° C. where D1D2 aggregated. A relatively early start of unfolding was also observed with mD1 and mD2 but about 25% of them remained folded at 67° C., where D1D2 was completely denatured, and their unfolding was completed at about 82° C. The Tms for mD1 and mD2 were about 58.3 and 55.1° C., respectively, which were comparable to that of D1D2. The CD spectra of mD1 and mD2 were similar to that of D1D2 (although there was a shift) and suggested that the D1 mutants still consisted primarily of β strands at 25° C.

The proteins were further assessed for sensitivity to trypsin digestion and degradation by human serum at 37° C. Proteolytic digestion of sCD4 in PBS was performed using trypsin at a protease/substrate ratio of 1:600 (w/w). For each reaction, 5 ng of trypsin in 2 μl PBS was added to 3 μg sCD4 in 5.5 μl PBS. The samples were incubated for 15, 30 and 60 minutes, respectively. The reactions were stopped by adding 2.5 μl SDS-PAGE gel-loading buffer containing 100 mM DTT to each reaction and boiling the samples for 5 min at 100° C. Samples collected at different time points and stored at −20° C. were subjected together to SDS-PAGE electrophoresis followed by staining with Coomassie Brilliant Blue R250.

Samples in PBS were mixed at 1:1 ratio (v/v) with human serum (or PBS as a control) to make a total volume of 35 μL and final concentration of each sample equal to 8300 nM. After 5, 10, and 15 days of incubation at 37° C., reactions were stopped by immediately freezing the samples at −20° C. After all samples were collected, 35 μL of 4% milk were added to each sample and then used in ELISA assays with gp140$_{Con-s}$. Standard curves were made by using the original proteins to quantify functional sCD4 surviving different periods of serum incubation.

After 30 minutes of incubation with trypsin, most of D1D2 was digested while a large percentage of the D1 mutants remained intact and a significant portion of the proteins survived 60-minute digestion. With human serum, D1D2 was degraded slowly within the first 5-day inoculation and then vanished quickly thereafter until the 15$^{th}$ day post inoculation (p.i.) when less than 1000 nM of the protein was left. In contrast, the D1 mutants disappeared relatively more rapidly within the first five days but the degradation was decelerated within 10 days thereafter and more than 1000 nM of the proteins were detected 15 days p.i. In all cases, the degradation was specific to trypsin or human serum because incubation of the proteins in PBS only at 37° C. for 15 days caused no significant loss in quantity.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

TABLE 3

D1 mutants potently inhibited infection of viruses pseudotyped with HIV-1 Envs from different clades.

| | | | IgG1 m102.4 | | Fab b12 | | D1D2 | | mD1 | | mD2 | |
|---|---|---|---|---|---|---|---|---|---|---|---|---|
| Virus | Clade | Tropism | $IC_{50}$ | $IC_{90}$ | $IC_{50}$[1] | $IC_{90}$[2] | $IC_{50}$ | $IC_{90}$ | $IC_{50}$ | $IC_{90}$ | $IC_{50}$ | $IC_{90}$ |
| 92UG037.8 | A | R5 | —[3] | — | — | — | 15 ± 2.1 | 63 ± 9.5 | 6.5 ± 0.4 | 38 ± 2.0 | 9.8 ± 3.1 | 40 ± 2.5 |
| Bal | B | R5 | — | — | 4.0 ± 0.2 | 29 ± 1.4 | 2.4 ± 0.7 | 17 ± 4.9 | 2.3 ± 0.9 | 13 ± 1.7 | 1.6 ± 0.2 | 11 ± 0.6 |
| JRFL | B | R5 | — | — | 1.4 ± 0.1 | 13 ± 2.7 | 14 ± 0.8 | 111 ± 7.5 | 12 ± 1.6 | 85 ± 6.4 | 15 ± 2.0 | 103 ± 5.6 |
| JRCSF | B | R5 | — | — | 30 ± 2.2 | 144 ± 23 | 41 ± 2.9 | 160 ± 8.5 | 17 ± 1.3 | 72 ± 5.0 | 11 ± 0.3 | 65 ± 1.4 |
| R2 | B | R5 | — | — | 720 ± 55 | >1667 | 3.3 ± 0.9 | 45 ± 7.0 | 1.0 ± 0.9 | 8.0 ± 3.5 | 0.6 ± 0.4 | 7.9 ± 1.5 |
| AD8 | B | R5 | — | — | 73 ± 11 | 280 ± 44 | 76 ± 9.1 | 150 ± 22 | 28 ± 4.5 | 136 ± 19 | 30 ± 1.7 | 125 ± 7.6 |
| 92HT | B | R5X4 | — | — | 10 ± 0.6 | 610 ± 39 | 6.0 ± 0.4 | 117 ± 10 | 1.1 ± 0.2 | 12 ± 3.4 | 1.8 ± 0.3 | 32 ± 8.5 |
| IIIB | B | X4 | — | — | <0.2 | 1.1 ± 0.2 | 0.3 ± 0.1 | 1.3 ± 0.2 | <0.2 | 1.1 ± 0.2 | <0.2 | 0.9 ± 0.3 |
| NL4-3 | B | X4 | — | — | 1.2 ± 0.4 | 30 ± 5.8 | <0.2 | 4.5 ± 0.7 | 0.4 ± 0.1 | 5.0 ± 0.9 | 0.3 ± 0.1 | 5.3 ± 1.6 |
| GXC-44 | C | R5 | — | — | — | — | 27 ± 0.3 | 1000 ± 68 | 155 ± 17 | >1667 | 50 ± 0.9 | >1667 |
| Z2Z6 | D | R5 | — | — | 145 ± 18 | >1667 | 72 ± 5.6 | >1667 | 12 ± 0.9 | 660 ± 34 | 60 ± 7.7 | 783 ± 15 |
| GXE | E | R5 | — | — | 630 ± 45 | >1667 | 154 ± 8.9 | 1080 ± 46 | 54 ± 3.2 | 280 ± 6.3 | 44 ± 1.5 | 150 ± 17 |
| CM243 | E | R5 | — | — | — | — | 43 ± 2.5 | 670 ± 50 | 3.6 ± 0.2 | 150 ± 9.2 | 18 ± 2.1 | 161 ± 4.0 |
| Arithmatic mean[4] | | | — | — | 161 | 711 | 35 | 417 | 23 | 266 | 19 | 268 |
| Geometric mean[4] | | | — | — | 16 | 138 | 10 | 102 | 5.0 | 50 | 5.6 | 51 |

[1]Antibody concentration (nM) resulting in 50% inhibition of virus infection.
[2]Antibody concentration (nM) resulting in 90% inhibition of virus infection.
[3]No significant neutralization at the highest antibody concentration (2000 nM) tested.
[4]Arithmetic and geometric means were calculated for sCD4 constructs and all viruses including those with values <0.2 nM, which were assigned a value of 0.1, and those with values >1667 nM, which were assigned a value of 2000. The means for Fab b12 were calculated based on the values of 10 isolates that were significantly neutralized.

TABLE 4

Neutralization of HIV-1 pseudotyped from different clades by m36.4-mD1 fusion proteins.

| | | | m36.4 | | D1D2 | | m36.4 + D1D2 | |
|---|---|---|---|---|---|---|---|---|
| Virus | Clade | Tropism | $IC_{50}$[1] | $IC_{90}$[2] | $IC_{50}$ | $IC_{90}$ | $IC_{50}$ | $IC_{90}$ |
| 92UG037.8 | A | R5 | 58 ± 9.5 | 150 ± 14 | 17 ± 3.6 | 121 ± 13 | 25 ± 8.3 | 115 ± 7.0 |
| Bal | B | R5 | 14 ± 0.8 | 101 ± 13 | 7.4 ± 2.0 | 26 ± 3.7 | 3.0 ± 0.2 | 13 ± 2.5 |
| JRFL | B | R5 | 27 ± 2.5 | 136 ± 18 | 30 ± 0.9 | 140 ± 21 | 8.5 ± 0.7 | 29 ± 3.1 |
| GXC | C | R5 | 3.5 ± 0.2 | 32 ± 1.8 | 28 ± 3.7 | 670 ± 34 | 6.0 ± 0.4 | 30 ± 1.9 |
| Arithmatic mean | | | 26 | 105 | 21 | 239 | 11 | 47 |
| Geometric mean | | | 17 | 90 | 18 | 131 | 7.9 | 34 |
| | | | m36.4L3D1 | | m36.4L6D1 | | m36.4L9D1 | |
| Virus | Clade | Tropism | $IC_{50}$ | $IC_{90}$ | $IC_{50}$ | $IC_{90}$ | $IC_{50}$ | $IC_{90}$ |
| 92UG037.8 | A | R5 | 9.0 ± 0.7 | 71 ± 5.6 | 6.0 ± 0.7 | 36 ± 1.5 | 13 ± 0.6 | 110 ± 18 |
| Bal | B | R5 | 3.3 ± 0.4 | 13 ± 0.9 | 3.1 ± 0.8 | 16 ± 2.7 | 3.0 ± 0.5 | 14 ± 1.8 |
| JRFL | B | R5 | 11 ± 1.3 | 40 ± 4.2 | 9.5 ± 2.2 | 39 ± 5.0 | 6.1 ± 0.8 | 33 ± 1.6 |
| GXC | C | R5 | 1.2 ± 0.3 | 34 ± 2.5 | 2.0 ± 0.6 | 21 ± 3.6 | 3.2 ± 0.5 | 63 ± 5.8 |
| Arithmatic mean | | | 6.1 | 40 | 5.2 | 28 | 6.3 | 55 |
| Geometric mean | | | 4.4 | 33 | 4.3 | 26 | 5.0 | 42 |

[1]Antibody concentration (nM) resulting in 50% inhibition of virus infection.
[2]Antibody concentration (nM) resulting in 90% inhibition of virus infection.

TABLE 5

Neutralization of HIV-1 pseudotyped from different clades by mD1-CH3 fusion proteins.

| | | | IgG1 m102.4 | | mD1 | | D1L3CH3 | | D1L6CH3 | | D1L9CH3 | |
|---|---|---|---|---|---|---|---|---|---|---|---|---|
| Virus | Clade | Tropism | $IC_{50}$[1] | $IC_{90}$[2] | $IC_{50}$ | $IC_{90}$ | $IC_{50}$ | $IC_{90}$ | $IC_{50}$ | $IC_{90}$ | $IC_{50}$ | $IC_{90}$ |
| 92UG037.8 | A | R5 | —[3] | — | 7.0 ± 1.2 | 65 ± 4.3 | 1.4 ± 0.7 | 20 ± 3.3 | 3.9 ± 0.5 | 40 ± 2.7 | 2.5 ± 0.4 | 16 ± 1.5 |
| Bal | B | R5 | — | — | 5.8 ± 1.1 | 14 ± 2.6 | 0.5 ± 0.1 | 1.7 ± 0.4 | 0.6 ± 0.2 | 2.4 ± 0.5 | 0.7 ± 0.1 | 3.5 ± 0.2 |
| JRFL | B | R5 | — | — | 29 ± 0.8 | 117 ± 9.5 | 2.5 ± 0.3 | 13 ± 1.6 | 1.6 ± 0.4 | 14 ± 2.0 | 1.4 ± 0.1 | 9.8 ± 0.5 |
| GXE | C | R5 | — | — | 300 ± 37 | >1667 | 22 ± 4.5 | >1667 | 26 ± 2.8 | >1667 | 15 ± 0.5 | 830 ± 44 |
| Arithmatic mean[4] | | | | | 85 | 549 | 6.6 | 509 | 8.0 | 514 | 4.9 | 215 |
| Geometric mean[4] | | | | | 24 | 121 | 2.5 | 31 | 3.1 | 40 | 2.5 | 26 |

[1]Antibody concentration (nM) resulting in 50% inhibition of virus infection.
[2]Antibody concentration (nM) resulting in 90% inhibition of virus infection.
[3]No significant neutralization at the highest antibody concentration (2000 nM) tested.
[4]Arithmetic and geometric means were calculated for all viruses including those with values >1667 nM, which were assigned a value of 2000.

TABLE 6

Neutralization of HIV-1 pseudotyped from different clades by m36.4-mD1-CH3 or -Fc fusion proteins.

| | | | m36.4L3D1 | | D1L3CH3 | | m36.4D1CH3 | | m36.4D1Fc | | m36.4L2CD4Fc | |
|---|---|---|---|---|---|---|---|---|---|---|---|---|
| Virus | Clade | Tropism | $IC_{50}$[1] | $IC_{90}$[2] | $IC_{50}$ | $IC_{90}$ | $IC_{50}$ | $IC_{90}$ | $IC_{50}$ | $IC_{90}$ | $IC_{50}$ | $IC_{90}$ |
| 92UG037.8 | A | R5 | 8.7 ± 0.5 | 52 ± 6.1 | 11 ± 0.9 | 113 ± 15 | 62 ± 9.4 | 240 ± 21 | 66 ± 3.8 | 372 ± 30 | 155 ± 1.3 | 1333 ± 56 |
| Bal | B | R5 | 6.5 ± 1.3 | 13 ± 0.7 | 0.4 ± 0.1 | 3.0 ± 0.5 | 6.7 ± 1.8 | 14 ± 0.9 | 12 ± 0.8 | 95 ± 7.0 | 7.3 ± 0.4 | 35 ± 4.2 |
| JRFL | B | R5 | 19 ± 0.7 | 100 ± 23 | 5.2 ± 1.5 | 26 ± 2.9 | 14 ± 0.8 | 96 ± 7.3 | 38 ± 3.4 | 122 ± 17 | 26 ± 1.5 | 150 ± 19 |
| Arithmatic mean | | | 11 | 55 | 5.5 | 47 | 28 | 117 | 39 | 196 | 63 | 506 |
| Geometric mean | | | 10 | 41 | 1.3 | 21 | 18 | 69 | 31 | 163 | 31 | 191 |

[1]Antibody concentration (nM) resulting in 50% inhibition of virus infection.
[2]Antibody concentration (nM) resulting in 90% inhibition of virus infection.

TABLE 7

Neutralization of HIV-1 pseudotyped with Envs from different clades.

| | | | IgG1 VRC01 | | mD1m36.4Fc6 | |
|---|---|---|---|---|---|---|
| Virus | Clade | Tropism | $IC_{50}$[1] | $IC_{90}$[2] | $IC_{50}$ | $IC_{90}$ |
| 92UG037.8 | A | R5 | 0.21 ± 0.03 | 2.0 ± 0.4 | 0.05 ± 0.01 | 2.0 ± 0.2 |
| Bal | B | R5 | 0.06 ± 0.001 | 0.75 ± 0.17 | 0.05 ± 0.02 | 0.32 ± 0.03 |
| JRFL | B | R5 | 0.24 ± 0.04 | 1.1 ± 0.2 | 0.12 ± 0.01 | 1.0 ± 0.4 |
| GXC | C | R5 | 2.1 ± 0.5 | 11 ± 2 | 0.44 ± 0.06 | 4.8 ± 1.0 |
| Arithmatic mean | | | 0.65 | 3.7 | 0.17 | 2.0 |
| Geometric mean | | | 0.28 | 2.1 | 0.11 | 1.3 |

[1]Antibody concentration (nM) resulting in 50% inhibition of virus infection.
[2]Antibody concentration (nM) resulting in 90% inhibition of virus infection.

The invention claimed is:

1. An isolated polypeptide comprising the amino acid sequence of SEQ ID NO: 11, provided that the polypeptide does not comprise the amino acid sequence of SEQ ID NO: 12.

2. An isolated polypeptide comprising the amino acid sequence of SEQ ID NO: 13 or SEQ ID NO: 14.

3. A composition comprising the polypeptide of claim 1.

4. A fusion protein comprising (i) the polypeptide of claim 1 and (ii) one or more fusion partners, wherein the one or more fusion partners optionally is fused to (i) via a linker.

5. The fusion protein of claim 4, wherein the linker comprises the amino acid sequence of one of SEQ ID NOs: 36-40.

6. The fusion protein of claim 4, wherein the fusion partner is selected from an engineered antibody domain (eAd), an HIV envelope glycoprotein, CD4 or a fragment or mimic thereof, an Fc region or portion thereof, an immunoglobulin heavy chain constant region, an immunoglobulin light chain constant region, or a combination thereof.

7. A composition comprising the fusion protein of claim 4 and a carrier.

8. A construct comprising two or more fusion proteins of claim 4.

9. The polypeptide of claim 1, comprising the amino acid sequence of SEQ ID NO: 17.

10. The polypeptide of claim 1, comprising the amino acid sequence of SEQ ID NO: 21.

11. The polypeptide of claim 1, comprising the amino acid sequence of SEQ ID NO: 23.

12. The polypeptide of claim 1, comprising the amino acid sequence of SEQ ID NO: 26.

13. The polypeptide of claim 1, comprising the amino acid sequence of SEQ ID NO: 27.

14. The polypeptide of claim 1, comprising the amino acid sequence of SEQ ID NO: 28.

15. An isolated polypeptide comprising the amino acid sequence of KKVVx$^1$x$^2$x$^3$x$^4$GDTVELx$^5$CTASQKKx$^6$IQFx$^7$WKx$^8$SNQIKILGNQGSFLTKGPSKLNDRx$^9$DSRRSLWDQGx$^{10}$FPLIIKNLKx$^{11}$EDSx$^{12}$TYICEVEDQKEEVQLx$^{13}$Vx$^{14}$G (SEQ ID NO: 11), wherein $x^1$ selected from the group consisting of I, Y, V, E, W, F, and T;
$x^2$ is G or A;
$x^3$ is K or Q;
$x^4$ is K or E;
$x^5$ is T or A;
$x^6$ is S or N;
$x^7$ is H or Q;
$x^8$ is N or D;
$x^9$ is A or V;
$x^{10}$ is N or S;
$x^{11}$ is selected from the group consisting of I, P, L, Y, V, S, and E;
$x^{12}$ is D or G;
$x^{13}$ is selected from the group consisting of L, I, V, H, and C; and
$x^{14}$ is selected from the group consisting of F, L, V, Q, R, I, and T.

16. The polypeptide of claim 15, wherein
$x^1$ is Y;
$x^2$ is G;
$x^3$ is K;
$x^4$ is K;
$x^5$ is T;
$x^6$ is N;
$x^7$ is H;
$x^8$ is N;
$x^9$ is V;
$x^{10}$ is N;
$x^{11}$ is P;
$x^{12}$ is D;
$x^{13}$ is V; and
$x^{14}$ is V.

17. The polypeptide of claim 15, wherein
$x^1$ is Y;
$x^2$ is G;
$x^3$ is K;
$x^4$ is K;
$x^5$ is T;
$x^6$ is N;
$x^7$ is H;
$x^8$ is D;
$x^9$ is A;
$x^{10}$ is N;
$x^{11}$ is P;
$x^{12}$ is D;
$x^{13}$ is V; and
$x^{14}$ is V.

* * * * *

SEQUENCE LISTING

```
<160> NUMBER OF SEQ ID NOS: 139

<210> SEQ ID NO 1
<211> LENGTH: 117
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

<210> SEQ ID NO 2
```

<211> LENGTH: 117
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Gly Gly Leu Val Gln Pro Gly Gly
1               5                   10                  15

Ser Leu Arg Leu Ser Cys Ala Ala Ser Thr Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Asn Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

<210> SEQ ID NO 3
<211> LENGTH: 117
<212> TYPE: PRT
<213> ORGANISM: Artificial Sequence
<220> FEATURE:
<223> OTHER INFORMATION: Synthetic

<400> SEQUENCE: 3

Gln Val Gln Leu Val Gln Ser Gly Gly Gly Leu Ile Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Asp Pro Gly Lys Gly Leu Glu Trp Ile
        35                  40                  45

Gly Glu Ile Asn Asp Arg Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

<210> SEQ ID NO 4
<211> LENGTH: 117
<212> TYPE: PRT
<213> ORGANISM: Artificial Sequence
<220> FEATURE:
<223> OTHER INFORMATION: Synthetic

<400> SEQUENCE: 4

Gln Val Gln Leu Val Gln Ser Gly Gly Gly Leu Val Gln Pro Gly Gly
1               5                   10                  15

```
Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
 50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

<210> SEQ ID NO 5
<211> LENGTH: 117
<212> TYPE: PRT
<213> ORGANISM: Artificial Sequence
<220> FEATURE:
<223> OTHER INFORMATION: Synthetic

<400> SEQUENCE: 5

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
 50                  55                  60

Ser Arg Val Thr Ile Ser Arg Asp Asn Ser Lys Asn Thr Leu Tyr Leu
65                  70                  75                  80

Gln Met Asn Thr Leu Ser Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser
        115

<210> SEQ ID NO 6
<211> LENGTH: 351
<212> TYPE: DNA
<213> ORGANISM: Artificial Sequence
<220> FEATURE:
<223> OTHER INFORMATION: Synthetic

<400> SEQUENCE: 6
caggtgcagc tggtgcagtc tgggggaggc ttggtacagc ctggagggtc cctgagactc      60
tcctgtgcag cctctgcttt cgatttctct gattatgaaa tgagctgggt ccgccaggct     120
ccagggaagg ggctggagtg gattgggaa atcaatgata gtggaaacac catttacaat     180
ccgtccctca agagtcgagt caccatctcc agagacaatt ccaagaacac gctgtatctg     240
caaatgaaca ccctgagagc cgaggacaca gccatatatt actgtgcgat atatggtggt     300
aactccgggg gagagtactg gggccagggc accctggtca ccgtctcctc a             351

<210> SEQ ID NO 7
```

<211> LENGTH: 351
<212> TYPE: DNA
<213> ORGANISM: Artificial Sequence
<220> FEATURE:
<223> OTHER INFORMATION: Synthetic

<400> SEQUENCE: 7

```
caggtgcagc tggtgcagtc tgggggaggc ttggtacagc ctggagggtc cctgagactc      60
tcctgtgcag cctctacttt cgatttctct gattatgaaa tgagctgggt ccgcgaggct     120
ccagggaagg ggctggagtg gattggggaa atcaatgata gtggaaacac catttacaat     180
ccgtccctca agaatcgagt caccatctcc agagacaatt ccaagaacac gctgtatctg     240
caaatgaaca ccctgagagc cgaggacaca gccatatatt actgtgcgat atatggtggt     300
aactccgggg gagagtactg gggccagggc accctggtca ccgtctcctc a              351
```

<210> SEQ ID NO 8
<211> LENGTH: 351
<212> TYPE: DNA
<213> ORGANISM: Artificial Sequence
<220> FEATURE:
<223> OTHER INFORMATION: Synthetic

<400> SEQUENCE: 8

```
caggtgcagc tggtgcagtc tgggggaggc ttgatacagc ctggagggtc cctgagactc      60
tcctgtgcag cctctgcttt cgatttctct gattatgaaa tgagctgggt ccgccaggat     120
ccagggaagg ggctggagtg gattggggaa atcaatgata gaggaaacac catttacaat     180
ccgtccctca agagtcgagt caccatctcc agagacaatt ccaagaacac gctgtatctg     240
caaatgaaca ccctgagagc cgaggacaca gccatatatt actgtgcgat atatggtggt     300
aactccgggg gagagtactg gggccagggc accctggtca ccgtctcctc a              351
```

<210> SEQ ID NO 9
<211> LENGTH: 351
<212> TYPE: DNA
<213> ORGANISM: Artificial Sequence
<220> FEATURE:
<223> OTHER INFORMATION: Synthetic

<400> SEQUENCE: 9

```
caggtgcagc tggtgcagtc tgggggaggc ttggtacagc ctggagggtc cctgagactc      60
tcctgtgcag cctctgcttt cgatttctct gattatgaaa tgagctgggt ccgcgaggct     120
ccagggaagg ggctggagtg gattggggaa atcaatgata gtggaaacac catttacaat     180
ccgtccctca agagtcgagt caccatctcc agagacaatt ccaagaacac actgtatctg     240
caaatgaaca ccctgagagc cgaggacaca gccatatatt actgtgcgat atatggtggt     300
aactccgggg gagagtactg gggccagggc accctggtca ccgtctcctc a              351
```

<210> SEQ ID NO 10
<211> LENGTH: 351
<212> TYPE: DNA
<213> ORGANISM: Artificial Sequence
<220> FEATURE:
<223> OTHER INFORMATION: Synthetic

<400> SEQUENCE: 10

```
caggtgcagc tggtgcagtc tgggggaggc ttggtacagc ctggagggtc cctgagactc      60
tcctgtgcag cctctgcttt cgatttctct gattatgaaa tgagctgggt ccgcgaggct     120
ccagggaagg ggctggagtg gattggggaa atcaatgata gtggaaacac catttacaat     180
```

-continued

```
ccgtccctca agagtcgagt caccatctcc agagacaatt ccaagaacac gctgtatctg      240
caaatgaaca ccctgagtgc cgaggacaca gccatatatt actgtgcgat atatggtggt      300
aactccgggg gagagtactg gggccagggc accctggtca ccgtctcctc a               351
```

<210> SEQ ID NO 11
<211> LENGTH: 99
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa at position 5 is any amino acid
<220> FEATURE:
<221> NAME/KEY: misc_feature
<222> LOCATION: (6)..(6)
<223> OTHER INFORMATION: Xaa at position 6 is any amino acid
<220> FEATURE:
<221> NAME/KEY: misc_feature
<222> LOCATION: (7)..(7)
<223> OTHER INFORMATION: Xaa at position 7 is any amino acid
<220> FEATURE:
<221> NAME/KEY: misc_feature
<222> LOCATION: (8)..(8)
<223> OTHER INFORMATION: Xaa at position 8 is any amino acid
<220> FEATURE:
<221> NAME/KEY: misc_feature
<222> LOCATION: (15)..(15)
<223> OTHER INFORMATION: Xaa at position 15 is any amino acid
<220> FEATURE:
<221> NAME/KEY: misc_feature
<222> LOCATION: (23)..(23)
<223> OTHER INFORMATION: Xaa at position 23 is any amino acid
<220> FEATURE:
<221> NAME/KEY: misc_feature
<222> LOCATION: (27)..(27)
<223> OTHER INFORMATION: Xaa at position 27 is any amino acid
<220> FEATURE:
<221> NAME/KEY: misc_feature
<222> LOCATION: (30)..(30)
<223> OTHER INFORMATION: Xaa at position 30 is any amino acid
<220> FEATURE:
<221> NAME/KEY: misc_feature
<222> LOCATION: (55)..(55)
<223> OTHER INFORMATION: Xaa at position 55 is any amino acid
<220> FEATURE:
<221> NAME/KEY: misc_feature
<222> LOCATION: (66)..(66)
<223> OTHER INFORMATION: Xaa at position 66 is any amino acid
<220> FEATURE:
<221> NAME/KEY: misc_feature
<222> LOCATION: (76)..(76)
<223> OTHER INFORMATION: Xaa at position 76 is any amino acid
<220> FEATURE:
<221> NAME/KEY: misc_feature
<222> LOCATION: (80)..(80)
<223> OTHER INFORMATION: Xaa at position 80 is any amino acid
<220> FEATURE:
<221> NAME/KEY: misc_feature
<222> LOCATION: (96)..(96)
<223> OTHER INFORMATION: Xaa at position 96 is any amino acid
<220> FEATURE:
<221> NAME/KEY: misc_feature
<222> LOCATION: (98)..(98)
<223> OTHER INFORMATION: Xaa at position 98 is any amino acid

<400> SEQUENCE: 11

```
Lys Lys Val Val Xaa Xaa Xaa Xaa Gly Asp Thr Val Glu Leu Xaa Cys
1               5                   10                  15

Thr Ala Ser Gln Lys Lys Xaa Ile Gln Phe Xaa Trp Lys Xaa Ser Asn
            20                  25                  30
```

```
Gln Ile Lys Ile Leu Gly Asn Gln Gly Ser Phe Leu Thr Lys Gly Pro
            35                  40                  45

Ser Lys Leu Asn Asp Arg Xaa Asp Ser Arg Arg Ser Leu Trp Asp Gln
 50                  55                  60

Gly Xaa Phe Pro Leu Ile Ile Lys Asn Leu Lys Xaa Glu Asp Ser Xaa
 65              70                  75                  80

Thr Tyr Ile Cys Glu Val Glu Asp Gln Lys Glu Glu Val Gln Leu Xaa
                85                  90                  95

Val Xaa Gly
```

<210> SEQ ID NO 12
<211> LENGTH: 99
<212> TYPE: PRT
<213> ORGANISM: Artificial Sequence
<220> FEATURE:
<223> OTHER INFORMATION: Synthetic

<400> SEQUENCE: 12

```
Lys Lys Val Val Leu Gly Lys Lys Gly Asp Thr Val Glu Leu Thr Cys
 1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ile Glu Asp Ser Asp
 65              70                  75                  80

Thr Tyr Ile Cys Glu Val Glu Asp Gln Lys Glu Glu Val Gln Leu Leu
                85                  90                  95

Val Phe Gly
```

<210> SEQ ID NO 13
<211> LENGTH: 99
<212> TYPE: PRT
<213> ORGANISM: Artificial Sequence
<220> FEATURE:
<223> OTHER INFORMATION: Synthetic

<400> SEQUENCE: 13

```
Lys Lys Val Val Ile Gly Lys Lys Gly Asp Thr Val Glu Leu Thr Cys
 1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
            35                  40                  45

Ser Lys Leu Asn Asp Arg Val Asp Ser Arg Arg Ser Leu Trp Asp Gln
 50                  55                  60

Gly Asn Phe Pro Leu Ile Ile Lys Asn Leu Lys Pro Glu Asp Ser Asp
 65              70                  75                  80

Thr Tyr Ile Cys Glu Val Glu Asp Gln Lys Glu Glu Val Gln Leu Ile
                85                  90                  95

Val Leu Gly
```

<210> SEQ ID NO 14
<211> LENGTH: 99
<212> TYPE: PRT
<213> ORGANISM: Artificial Sequence
<220> FEATURE:
<223> OTHER INFORMATION: Synthetic

<400> SEQUENCE: 14

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly

<210> SEQ ID NO 15
<211> LENGTH: 99
<212> TYPE: PRT
<213> ORGANISM: Artificial Sequence
<220> FEATURE:
<223> OTHER INFORMATION: Synthetic

<400> SEQUENCE: 15

Lys Lys Val Val Val Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Glu Val Gln Leu Ile
                85                  90                  95

Val Gln Gly

<210> SEQ ID NO 16
<211> LENGTH: 99
<212> TYPE: PRT
<213> ORGANISM: Artificial Sequence
<220> FEATURE:
<223> OTHER INFORMATION: Synthetic

<400> SEQUENCE: 16

Lys Lys Val Val Glu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Leu Glu Asp Ser Asp
65                  70                  75                  80

```
Thr Tyr Ile Cys Glu Val Glu Asp Gln Lys Glu Val Gln Leu Ile
                85                  90                  95

Val Arg Gly

<210> SEQ ID NO 17
<211> LENGTH: 99
<212> TYPE: PRT
<213> ORGANISM: Artificial Sequence
<220> FEATURE:
<223> OTHER INFORMATION: Synthetic

<400> SEQUENCE: 17

Lys Lys Val Val Trp Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
        50                  55                  60

Gly Asn Phe Pro Leu Ile Ile Lys Asn Leu Lys Ile Glu Asp Ser Asp
65                  70                  75                  80

Thr Tyr Ile Cys Glu Val Glu Asp Gln Lys Glu Val Gln Leu Val
                85                  90                  95

Val Leu Gly

<210> SEQ ID NO 18
<211> LENGTH: 99
<212> TYPE: PRT
<213> ORGANISM: Artificial Sequence
<220> FEATURE:
<223> OTHER INFORMATION: Synthetic

<400> SEQUENCE: 18

Lys Lys Val Val Tyr Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
        50                  55                  60

Gly Asn Phe Pro Leu Ile Ile Lys Asn Leu Lys Tyr Glu Asp Ser Asp
65                  70                  75                  80

Thr Tyr Ile Cys Glu Val Glu Asp Gln Lys Glu Val Gln Leu Ile
                85                  90                  95

Val Ile Gly

<210> SEQ ID NO 19
<211> LENGTH: 99
<212> TYPE: PRT
<213> ORGANISM: Artificial Sequence
<220> FEATURE:
<223> OTHER INFORMATION: Synthetic

<400> SEQUENCE: 19

Lys Lys Val Val Tyr Gly Lys Lys Gly Asp Thr Val Glu Leu Thr Cys
1               5                   10                  15
```

```
Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Leu Glu Asp Ser Asp
65                  70                  75                  80

Thr Tyr Ile Cys Glu Val Glu Asp Gln Lys Glu Glu Val Gln Leu Ile
                85                  90                  95

Val Thr Gly

<210> SEQ ID NO 20
<211> LENGTH: 99
<212> TYPE: PRT
<213> ORGANISM: Artificial Sequence
<220> FEATURE:
<223> OTHER INFORMATION: Synthetic

<400> SEQUENCE: 20

Lys Lys Val Val Tyr Gly Gln Glu Gly Asp Thr Val Glu Leu Thr Cys
1               5                   10                  15

Thr Ala Ser Gln Lys Lys Ser Ile Gln Phe Gln Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Val Glu Asp Ser Asp
65                  70                  75                  80

Thr Tyr Ile Cys Glu Val Asp Gln Lys Glu Glu Val Gln Leu Ile
                85                  90                  95

Val Leu Gly

<210> SEQ ID NO 21
<211> LENGTH: 99
<212> TYPE: PRT
<213> ORGANISM: Artificial Sequence
<220> FEATURE:
<223> OTHER INFORMATION: Synthetic

<400> SEQUENCE: 21

Lys Lys Val Val Val Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Ile
                85                  90                  95

Val Phe Leu

<210> SEQ ID NO 22
```

```
<211> LENGTH: 99
<212> TYPE: PRT
<213> ORGANISM: Artificial Sequence
<220> FEATURE:
<223> OTHER INFORMATION: Synthetic

<400> SEQUENCE: 22

Lys Lys Val Val Tyr Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Val Glu Asp Ser Asp
65                  70                  75                  80

Thr Tyr Ile Cys Glu Val Glu Asp Gln Lys Glu Glu Val Gln Leu His
                85                  90                  95

Val Ile Gly

<210> SEQ ID NO 23
<211> LENGTH: 99
<212> TYPE: PRT
<213> ORGANISM: Artificial Sequence
<220> FEATURE:
<223> OTHER INFORMATION: Synthetic

<400> SEQUENCE: 23

Lys Lys Val Val Ile Gly Lys Lys Gly Asp Thr Val Glu Leu Thr Cys
1               5                   10                  15

Thr Ala Ser Gln Lys Lys Ser Ile Gln Phe His Trp Lys Asp Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
    50                  55                  60

Gly Ser Phe Pro Leu Ile Ile Lys Asn Leu Lys Leu Glu Asp Ser Asp
65                  70                  75                  80

Thr Tyr Ile Cys Glu Val Glu Asp Gln Lys Glu Glu Val Gln Leu Cys
                85                  90                  95

Val Val Gly

<210> SEQ ID NO 24
<211> LENGTH: 99
<212> TYPE: PRT
<213> ORGANISM: Artificial Sequence
<220> FEATURE:
<223> OTHER INFORMATION: Synthetic

<400> SEQUENCE: 24

Lys Lys Val Val Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
                20                  25                  30

Gln Ile Lys Ile Leu Gly Asn Gln Gly Ser Phe Leu Thr Lys Gly Pro
            35                  40                  45

Ser Lys Leu Asn Asp Arg Ala Asp Ser Arg Arg Ser Leu Trp Asp Gln
    50                  55                  60
```

```
Gly Asn Phe Pro Leu Ile Ile Lys Asn Leu Lys Leu Glu Asp Ser Asp
 65                  70                  75                  80

Thr Tyr Ile Cys Glu Val Glu Asp Gln Lys Glu Val Gln Leu Ile
                 85                  90                  95

Val Ile Gly

<210> SEQ ID NO 25
<211> LENGTH: 99
<212> TYPE: PRT
<213> ORGANISM: Artificial Sequence
<220> FEATURE:
<223> OTHER INFORMATION: Synthetic

<400> SEQUENCE: 25

Lys Lys Val Val Val Gly Lys Lys Gly Asp Thr Val Glu Leu Thr Cys
 1               5                  10                  15

Thr Ala Ser Gln Lys Lys Ser Ile Gln Phe His Trp Lys Asn Ser Asn
                 20                  25                  30

Gln Ile Lys Ile Leu Gly Asn Gln Gly Ser Phe Leu Thr Lys Gly Pro
             35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Ser Glu Asp Ser Asp
 65                  70                  75                  80

Thr Tyr Ile Cys Glu Val Glu Asp Gln Lys Glu Val Gln Leu Ile
                 85                  90                  95

Val Val Gly

<210> SEQ ID NO 26
<211> LENGTH: 99
<212> TYPE: PRT
<213> ORGANISM: Artificial Sequence
<220> FEATURE:
<223> OTHER INFORMATION: Synthetic

<400> SEQUENCE: 26

Lys Lys Val Val Val Gly Lys Lys Gly Asp Thr Val Glu Leu Thr Cys
 1               5                  10                  15

Thr Ala Ser Gln Lys Lys Asn Ile Gln Phe His Trp Lys Asn Ser Asn
                 20                  25                  30

Gln Ile Lys Ile Leu Gly Asn Gln Gly Ser Phe Leu Thr Lys Gly Pro
             35                  40                  45

Ser Lys Leu Asn Asp Arg Ala Asp Ser Arg Arg Ser Leu Trp Asp Gln
 50                  55                  60

Gly Asn Phe Pro Leu Ile Ile Lys Asn Leu Lys Pro Glu Asp Ser Asp
 65                  70                  75                  80

Thr Tyr Ile Cys Glu Val Glu Asp Gln Lys Glu Val Gln Leu Leu
                 85                  90                  95

Val Thr Gly

<210> SEQ ID NO 27
<211> LENGTH: 99
<212> TYPE: PRT
<213> ORGANISM: Artificial Sequence
<220> FEATURE:
<223> OTHER INFORMATION: Synthetic

<400> SEQUENCE: 27
```

Lys Lys Val Val Phe Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Leu Glu Asp Ser Asp
65                  70                  75                  80

Thr Tyr Ile Cys Glu Val Glu Asp Gln Lys Glu Glu Val Gln Leu Ile
                85                  90                  95

Val Thr Gly

<210> SEQ ID NO 28
<211> LENGTH: 99
<212> TYPE: PRT
<213> ORGANISM: Artificial Sequence
<220> FEATURE:
<223> OTHER INFORMATION: Synthetic

<400> SEQUENCE: 28

Lys Lys Val Val Tyr Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Leu Glu Asp Ser Asp
65                  70                  75                  80

Thr Tyr Ile Cys Glu Val Glu Asp Gln Lys Glu Glu Val Gln Leu Ile
                85                  90                  95

Val Leu Gly

<210> SEQ ID NO 29
<211> LENGTH: 99
<212> TYPE: PRT
<213> ORGANISM: Artificial Sequence
<220> FEATURE:
<223> OTHER INFORMATION: Synthetic

<400> SEQUENCE: 29

Lys Lys Val Val Gly Lys Lys Gly Asp Thr Val Glu Leu Ala Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Val Glu Asp Ser Asp
65                  70                  75                  80

Thr Tyr Ile Cys Glu Val Glu Asp Gln Lys Glu Glu Val Gln Leu Val
                85                  90                  95

Val Val Gly

```
<210> SEQ ID NO 30
<211> LENGTH: 99
<212> TYPE: PRT
<213> ORGANISM: Artificial Sequence
<220> FEATURE:
<223> OTHER INFORMATION: Synthetic

<400> SEQUENCE: 30

Lys Lys Val Val Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Glu Glu Asp Ser Gly
65                  70                  75                  80

Thr Tyr Ile Cys Glu Val Glu Asp Gln Lys Glu Glu Val Gln Leu Val
                85                  90                  95

Val Val Gly

<210> SEQ ID NO 31
<211> LENGTH: 99
<212> TYPE: PRT
<213> ORGANISM: Artificial Sequence
<220> FEATURE:
<223> OTHER INFORMATION: Synthetic

<400> SEQUENCE: 31

Lys Lys Val Val Thr Ala Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Arg Ser Leu Trp Asp Gln
    50                  55                  60

Gly Asn Phe Pro Leu Ile Ile Lys Asn Leu Lys Leu Glu Asp Ser Asp
65                  70                  75                  80

Thr Tyr Ile Cys Glu Val Glu Asp Gln Lys Glu Glu Val Gln Leu Ile
                85                  90                  95

Val Gln Gly

<210> SEQ ID NO 32
<211> LENGTH: 178
<212> TYPE: PRT
<213> ORGANISM: Artificial Sequence
<220> FEATURE:
<223> OTHER INFORMATION: Synthetic

<400> SEQUENCE: 32

Lys Lys Val Val Leu Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45
```

```
Ser Lys Leu Asn Asp Arg Ala Asp Ser Arg Arg Ser Leu Trp Asp Gln
 50                  55                  60
Gly Asn Phe Pro Leu Ile Ile Lys Asn Leu Lys Ile Glu Asp Ser Asp
 65                  70                  75                  80
Thr Tyr Ile Cys Glu Val Glu Asp Gln Lys Glu Glu Val Gln Leu Leu
                 85                  90                  95
Val Phe Gly Leu Thr Ala Asn Ser Asp Thr His Leu Leu Gln Gly Gln
                100                 105                 110
Ser Leu Thr Leu Thr Leu Glu Ser Pro Pro Gly Ser Ser Pro Ser Val
            115                 120                 125
Gln Cys Arg Ser Pro Arg Gly Lys Asn Ile Gln Gly Gly Lys Thr Leu
        130                 135                 140
Ser Val Ser Gln Leu Glu Leu Gln Asp Ser Gly Thr Trp Thr Cys Thr
145                 150                 155                 160
Val Leu Gln Asn Gln Lys Lys Val Glu Phe Lys Ile Asp Ile Val Val
                165                 170                 175
Leu Ala
```

<210> SEQ ID NO 33
<211> LENGTH: 297
<212> TYPE: DNA
<213> ORGANISM: Artificial Sequence
<220> FEATURE:
<223> OTHER INFORMATION: Synthetic

<400> SEQUENCE: 33

```
aagaaggtgg tgatcggcaa gaagggcgac accgtggagc tgacctgcac cgccagccag      60
aagaagagca tccagttcca ctggaagaac agcaaccaga tcaagatcct gggcaaccag     120
ggcagcttcc tgaccaaggg acctagcaag ctgaacgaca gggtagacag ccggcggagc     180
ctgtgggacc agggaaactt cccactgatc atcaagaacc tgaagcctga ggacagcgac     240
acctacatct gcgaggtgga ggaccagaag gaggaggtgc agctgatagt gctaggc       297
```

<210> SEQ ID NO 34
<211> LENGTH: 297
<212> TYPE: DNA
<213> ORGANISM: Artificial Sequence
<220> FEATURE:
<223> OTHER INFORMATION: Synthetic

<400> SEQUENCE: 34

```
aagaaggtgg tgtacggcaa gaagggcgac accgtggagc tgacctgcac cgccagccag      60
aagaagaaca tccagttcca ctggaagaac agcaaccaga tcaagatcct gggcaaccag     120
ggcagcttcc tgaccaaggg acctagcaag ctgaacgaca gggcagacag ccggcggagc     180
ctgtgggacc agggaaactt cccactgatc atcaagaacc tgaagccaga ggacagcgac     240
acctacatct gcgaggtgga ggaccagaag gaggaggtgc agctggtagt ggtaggc       297
```

<210> SEQ ID NO 35
<211> LENGTH: 178
<212> TYPE: PRT
<213> ORGANISM: Artificial Sequence
<220> FEATURE:
<223> OTHER INFORMATION: Synthetic

<400> SEQUENCE: 35

```
Lys Lys Val Val Leu Gly Lys Lys Gly Asp Thr Val Glu Leu Thr Cys
  1               5                  10                  15
```

```
Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Ala Asp Ser Arg Ser Leu Trp Asp Gln
 50                  55                  60

Gly Asn Phe Pro Leu Ile Ile Lys Asn Leu Lys Ile Glu Asp Ser Asp
 65                  70                  75                  80

Thr Tyr Ile Cys Glu Val Asp Gln Lys Glu Val Gln Leu Leu
                85                  90                  95

Val Phe Gly Leu Thr Ala Asn Ser Asp Thr His Leu Leu Gln Gly Gln
            100                 105                 110

Ser Leu Thr Leu Thr Leu Glu Ser Pro Pro Gly Ser Ser Pro Ser Val
        115                 120                 125

Gln Cys Arg Ser Pro Arg Gly Lys Asn Ile Gln Gly Gly Lys Thr Leu
130                 135                 140

Ser Val Ser Gln Leu Glu Leu Gln Asp Ser Gly Thr Trp Thr Cys Thr
145                 150                 155                 160

Val Leu Gln Asn Gln Lys Lys Val Glu Phe Lys Ile Asp Ile Val Val
                165                 170                 175

Leu Ala

<210> SEQ ID NO 36
<211> LENGTH: 39
<212> TYPE: PRT
<213> ORGANISM: Artificial Sequence
<220> FEATURE:
<223> OTHER INFORMATION: Synthetic

<400> SEQUENCE: 36

Gly Gly Gly Ser Gly Gly Gly Ser Gly Gly Gly Ser Glu Gly Gly
1               5                   10                  15

Ser Glu Gly Gly Gly Ser Gly Gly Gly Ser Glu Gly Gly Gly Ser
                20                  25                  30

Gly Gly Gly Ser Gly Ser Gly
            35

<210> SEQ ID NO 37
<211> LENGTH: 27
<212> TYPE: PRT
<213> ORGANISM: Artificial Sequence
<220> FEATURE:
<223> OTHER INFORMATION: Synthetic

<400> SEQUENCE: 37

Glu Gly Gly Gly Ser Glu Gly Gly Gly Ser Glu Gly Gly Ser Glu
1               5                   10                  15

Gly Gly Gly Ser Gly Gly Gly Ser Gly Ser Gly
            20                  25

<210> SEQ ID NO 38
<211> LENGTH: 15
<212> TYPE: PRT
<213> ORGANISM: Artificial Sequence
<220> FEATURE:
<223> OTHER INFORMATION: Synthetic

<400> SEQUENCE: 38

Gly Gly Gly Gly Ser Gly Gly Gly Gly Ser Gly Gly Gly Gly Ser
```

<210> SEQ ID NO 39
<211> LENGTH: 30
<212> TYPE: PRT
<213> ORGANISM: Artificial Sequence
<220> FEATURE:
<223> OTHER INFORMATION: Synthetic

<400> SEQUENCE: 39

Gly Gly Gly Gly Ser Gly Gly Gly Ser Gly Gly Gly Ser Gly
1               5                  10                  15

Gly Gly Ser Gly Gly Gly Ser Gly Gly Gly Ser
            20                  25                  30

<210> SEQ ID NO 40
<211> LENGTH: 45
<212> TYPE: PRT
<213> ORGANISM: Artificial Sequence
<220> FEATURE:
<223> OTHER INFORMATION: Synthetic

<400> SEQUENCE: 40

Gly Gly Gly Gly Ser Gly Gly Gly Ser Gly Gly Gly Ser Gly
1               5                  10                  15

Gly Gly Ser Gly Gly Gly Ser Gly Gly Gly Ser Gly Gly
            20                  25                  30

Gly Ser Gly Gly Gly Gly Ser Gly Gly Gly Ser
    35                  40                  45

<210> SEQ ID NO 41
<211> LENGTH: 227
<212> TYPE: PRT
<213> ORGANISM: Artificial Sequence
<220> FEATURE:
<223> OTHER INFORMATION: Synthetic

<400> SEQUENCE: 41

Asp Lys Thr His Thr Cys Pro Pro Cys Pro Ala Pro Glu Leu Leu Gly
1               5                  10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys
225

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 43
<211> LENGTH: 408
<212> TYPE: PRT
<213> ORGANISM: Artificial Sequence
<220> FEATURE:
<223> OTHER INFORMATION: Synthetic

<400> SEQUENCE: 43

Glu Val Val Leu Gly Asn Val Thr Glu Asn Phe Asn Met Trp Lys Asn
1               5                   10                  15

Asn Met Val Glu Gln Met His Glu Asp Ile Ile Ser Leu Trp Asp Gln
            20                  25                  30

Ser Leu Lys Pro Cys Val Lys Leu Thr Pro Leu Cys Val Thr Leu Asn
        35                  40                  45

Cys Thr Asp Glu Leu Arg Asn Gly Thr Tyr Ala Asn Val Thr Val Thr
    50                  55                  60

Glu Lys Gly Glu Ile Lys Asn Cys Ser Phe Asn Ile Thr Thr Ala Ile
65                  70                  75                  80

Arg Asp Lys Val Gln Lys Thr Tyr Ala Leu Phe Tyr Arg Leu Asp Val
                85                  90                  95

Val Pro Ile Asp Asn Asn His Gly Asn Ser Ser Ser Asn Tyr Ser Asn
            100                 105                 110

Tyr Arg Leu Ile Asn Cys Asn Thr Ser Val Ile Thr Gln Ala Cys Pro
        115                 120                 125

Lys Val Ser Phe Glu Pro Ile Pro Ile His Tyr Cys Ala Pro Ala Gly

```
                130               135               140
    Phe Ala Ile Leu Lys Cys Asn Asn Lys Phe Asn Gly Thr Gly Pro
145                 150                 155                 160

Cys Lys Asn Val Ser Thr Val Gln Cys Thr His Gly Ile Arg Pro Val
                    165                 170                 175

Val Ser Thr Gln Leu Leu Leu Asn Gly Ser Leu Ala Glu Glu Val
                    180                 185                 190

Val Ile Arg Ser Glu Asn Phe Thr Asp Asn Ala Lys Thr Ile Ile Val
                    195                 200                 205

Gln Leu Asn Asp Ser Val Ile Ile Asn Cys Thr Arg Pro Asn Asn Asn
                    210                 215                 220

Thr Arg Lys Gly Ile Thr Ile Gly Pro Gly Arg Val Phe Tyr Thr Gly
225                 230                 235                 240

Glu Ile Val Gly Asp Ile Arg Gln Val His Cys Asn Leu Ser Ser Ala
                    245                 250                 255

Lys Trp Asn Ser Thr Leu Lys Gln Val Val Thr Lys Leu Arg Glu Gln
                    260                 265                 270

Phe Gly Asn Lys Thr Ile Val Phe Asn Gln Ser Ser Gly Gly Asp Pro
                    275                 280                 285

Glu Ile Val Met His Ser Phe Asn Cys Gly Gly Glu Phe Phe Cys
290                 295                 300

Asn Thr Thr Gln Leu Phe Asn Ser Thr Trp Asn Ile Asn Gly Thr Trp
305                 310                 315                 320

His Gly Thr Thr Val Ser Asn Lys Thr Ile Ile Leu Pro Cys Arg Ile
                    325                 330                 335

Lys Gln Ile Ile Asn Met Trp Gln Glu Val Gly Lys Ala Met Tyr Ala
                    340                 345                 350

Pro Pro Ile Arg Gly Gln Ile Arg Cys Ser Ser Asn Ile Thr Gly Leu
                    355                 360                 365

Leu Leu Thr Arg Asp Gly Gly Asn Asn Asn Ser Thr Thr Glu Ile Phe
                    370                 375                 380

Arg Pro Gly Gly Gly Asp Met Arg Asp Asn Trp Arg Ser Glu Leu Tyr
385                 390                 395                 400

Lys Tyr Lys Val Val Lys Ile Glu
                    405

<210> SEQ ID NO 44
<211> LENGTH: 1008
<212> TYPE: DNA
<213> ORGANISM: Artificial Sequence
<220> FEATURE:
<223> OTHER INFORMATION: Synthetic

<400> SEQUENCE: 44
caggtgcagc tggtgcagtc tggggaggc ttggtacagc ctggagggtc cctgagactc    60
tcctgtgcag cctctgcttt cgatttctct gattatgaaa tgagctgggt ccgccaggct   120
ccagggaagg ggctggagtg gattggggaa atcaatgata gtggaaacac catttacaat   180
ccgtccctca gagtcgagt caccatctcc agagacaatt ccaagaacac gctgtatctg   240
caaatgaaca ccctgagagc cgaggacaca gccatatatt actgtgcgat atatggtggt   300
aactccgggg gagagtactg gggccagggc accctggtca ccgtctcctc agggcccggc   360 ggcggtctg gtggtggttc tgtggccggc tctgaggggtg gtggctctga gggtggcggt   420 tctgaggggtg gcggctctga gggaggcggt tccggtggtg gctctggttc cggtaagaag   480
```

```
gtggtgctgg gcaagaaggg cgacaccgtg gagctgacct gcaccgccag ccagaagaag      540
agcatccagt tccactggaa gaacagcaac cagatcaaga tcctgggcaa ccagggcagc      600
ttcctgacca agggacctag caagctgaac gacagggcag acagccggcg gagcctgtgg      660
gaccagggaa acttcccact gatcatcaag aacctgaaga tcgaggacag cgacacctac      720
atctgcgagg tggaggacca gaaggaggag gtgcagctgc tggtgttcgg cctgaccgcc      780
aacagcgaca cccacctgct gcagggccag agcctgaccc tgaccctgga gagcccacca      840
ggaagcagcc caagcgtgca gtgccggagc ccaaggggca gaacatcca gggaggcaag       900 accctgagcg tgagccagct ggagctgcag gacagcggca cctggacctg caccgtgctg      960
cagaaccaga agaaggtgga gttcaagatc gacatcgtgg tgctggcc               1008
```

<210> SEQ ID NO 45
<211> LENGTH: 336
<212> TYPE: PRT
<213> ORGANISM: Artificial Sequence
<220> FEATURE:
<223> OTHER INFORMATION: Synthetic

<400> SEQUENCE: 45

```
Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Pro Gly Gly Ser Gly Gly Gly Ser Gly
        115                 120                 125

Gly Gly Ser Glu Gly Gly Gly Ser Glu Gly Gly Gly Ser Glu Gly Gly
    130                 135                 140

Gly Ser Glu Gly Gly Gly Ser Gly Gly Gly Ser Gly Ser Gly Lys Lys
145                 150                 155                 160

Val Val Leu Gly Lys Lys Gly Asp Thr Val Glu Leu Thr Cys Thr Ala
                165                 170                 175

Ser Gln Lys Lys Ser Ile Gln Phe His Trp Lys Asn Ser Asn Gln Ile
            180                 185                 190

Lys Ile Leu Gly Asn Gln Gly Ser Phe Leu Thr Lys Gly Pro Ser Lys
        195                 200                 205

Leu Asn Asp Arg Ala Asp Ser Arg Arg Ser Leu Trp Asp Gln Gly Asn
    210                 215                 220

Phe Pro Leu Ile Ile Lys Asn Leu Lys Ile Glu Asp Ser Asp Thr Tyr
225                 230                 235                 240

Ile Cys Glu Val Glu Asp Gln Lys Glu Glu Val Gln Leu Leu Val Phe
                245                 250                 255

Gly Leu Thr Ala Asn Ser Asp Thr His Leu Leu Gln Gly Gln Ser Leu
            260                 265                 270
```

Thr Leu Thr Leu Glu Ser Pro Pro Gly Ser Ser Pro Ser Val Gln Cys
            275                 280                 285

Arg Ser Pro Arg Gly Lys Asn Ile Gln Gly Gly Lys Thr Leu Ser Val
    290                 295                 300

Ser Gln Leu Glu Leu Gln Asp Ser Gly Thr Trp Thr Cys Thr Val Leu
305                 310                 315                 320

Gln Asn Gln Lys Lys Val Glu Phe Lys Ile Asp Ile Val Val Leu Ala
                325                 330                 335

<210> SEQ ID NO 46
<211> LENGTH: 972
<212> TYPE: DNA
<213> ORGANISM: Artificial Sequence
<220> FEATURE:
<223> OTHER INFORMATION: Synthetic

<400> SEQUENCE: 46
caggtgcagc tggtgcagtc tgggggaggc ttggtacagc ctggagggtc cctgagactc     60
tcctgtgcag cctctgcttt cgatttctct gattatgaaa tgagctgggt ccgccaggct    120
ccagggaagg ggctggagtg gattgggaa atcaatgata gtggaaacac catttacaat     180
ccgtccctca gagtcgagt caccatctcc agagacaatt ccaagaacac gctgtatctg     240
caaatgaaca ccctgagagc cgaggacaca gccatatatt actgtgcgat atatggtggt    300
aactccgggg gagagtactg gggccagggc accctggtca ccgtctcctc agggcccgag    360
ggtggtggct ctgagggtgg cggttctgag ggtggcggct ctgagggagg cggttccggt    420
ggtggctctg gttccggtaa gaaggtggtg ctgggcaaga agggcgacac cgtggagctg    480
acctgcaccg ccagccagaa gagagcatc cagttccact ggaagaacag caaccagatc    540
aagatcctgg caaccagggg cagcttcctg accaagggac ctagcaagct gaacgacagg    600
gcagacagcc ggcggagcct gtgggaccag ggaaacttcc cactgatcat caagaacctg    660
aagatcgagg acagcgacac ctacatctgc gaggtggagg accagaagga ggaggtgcag    720
ctgctggtgt tcggcctgac cgccaacagc gacacccacc tgctgcaggg ccagagcctg    780
accctgaccc tggagagccc caggaagc agcccaagcg tgcagtgccg gagcccaagg    840
ggcaagaaca tccagggagg caagaccctg agcgtgagcc agctggagct gcaggacagc    900
ggcacctgga cctgcaccgt gctgcagaac cagaagaagg tggagttcaa gatcgacatc    960
gtggtgctgg cc                                                         972

<210> SEQ ID NO 47
<211> LENGTH: 324
<212> TYPE: PRT
<213> ORGANISM: Artificial Sequence
<220> FEATURE:
<223> OTHER INFORMATION: Synthetic

<400> SEQUENCE: 47

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu

Gln Met Asn Thr Leu Arg Ala Glu Asp Thr Ala Ile Tyr Tyr Cys Ala
65                  70                  75                  80

Ile Tyr Gly Gly Asn Ser Gly Gly Glu Tyr Trp Gly Gln Gly Thr Leu
            85                  90                  95

Val Thr Val Ser Ser Gly Pro Glu Gly Gly Ser Glu Gly Gly Gly
        100                 105                 110

Ser Glu Gly Gly Gly Ser Glu Gly Gly Gly Ser Gly Gly Gly Ser Gly
        115                 120                 125

Ser Gly Lys Lys Val Val Leu Gly Lys Lys Gly Asp Thr Val Glu Leu
130                 135                 140

Thr Cys Thr Ala Ser Gln Lys Lys Ser Ile Gln Phe His Trp Lys Asn
145                 150                 155                 160

Ser Asn Gln Ile Lys Ile Leu Gly Asn Gln Gly Ser Phe Leu Thr Lys
            165                 170                 175

Gly Pro Ser Lys Leu Asn Asp Arg Ala Asp Ser Arg Arg Ser Leu Trp
        180                 185                 190

Asp Gln Gly Asn Phe Pro Leu Ile Ile Lys Asn Leu Lys Ile Glu Asp
            195                 200                 205

Ser Asp Thr Tyr Ile Cys Glu Val Glu Asp Gln Lys Glu Glu Val Gln
225             210                 215                 220

Leu Leu Val Phe Gly Leu Thr Ala Asn Ser Asp Thr His Leu Leu Gln
            225                 230                 235                 240

Gly Gln Ser Leu Thr Leu Thr Leu Glu Ser Pro Pro Gly Ser Ser Pro
            245                 250                 255

Ser Val Gln Cys Arg Ser Pro Arg Gly Lys Asn Ile Gln Gly Gly Lys
            260                 265                 270

Thr Leu Ser Val Ser Gln Leu Glu Leu Gln Asp Ser Gly Thr Trp Thr
            275                 280                 285

Cys Thr Val Leu Gln Asn Gln Lys Lys Val Glu Phe Lys Ile Asp Ile
305             290                 295                 300

Val Val Leu Ala
                305                 310                 315                 320

<210> SEQ ID NO 48
<211> LENGTH: 972
<212> TYPE: DNA
<213> ORGANISM: Artificial Sequence
<220> FEATURE:
<223> OTHER INFORMATION: Synthetic

<400> SEQUENCE: 48
caggtgcagc tggtgcagtc tgggggaggc ttggtacagc ctggagggtc cctgagactc      60
tcctgtgcag cctctgcttt cgatttctct gattatgaaa tgagctgggt ccgcgaggct     120
ccagggaagg gcctggagtg gattgggaa tcaatgata gtggaaacac catttacaat       180
ccgtccctca agagtcgagt caccatctcc agagacaatt ccaagaacac actgtatctg     240
caaatgaaca cccctgagagc cgaggacaca gccatatatt actgtgcgat atatggtggt     300
aactccgggg gagagtactg gggccagggc accctggtca ccgtctcctc agggcccgag     360
ggtggtggct ctgagggtgg cggttctgag ggtggcggct ctgagggagg cggttccggt     420
ggtggctctg gttccggtaa aaggtggtg ctgggcaaga aggggcgacac cgtggagctg     480
acctgcaccg ccagccagaa gaagagcatc cagttccact ggaagaacag caaccagatc     540
aagatcctgg gcaaccaggg cagcttcctg accaagggac ctagcaagct gaacgacagg     600

```
gcagacagcc ggcggagcct gtgggaccag ggaaacttcc cactgatcat caagaacctg    660
aagatcgagg acagcgacac ctacatctgc gaggtggagg accagaagga ggaggtgcag    720
ctgctggtgt tcggcctgac cgccaacagc gacacccacc tgctgcaggg ccagagcctg    780
accctgaccc tggagagccc accaggaagc agcccaagcg tgcagtgccg gagcccaagg    840
ggcaagaaca tccagggagg caagaccctg agcgtgagcc agctggagct gcaggacagc    900
ggcacctgga cctgcaccgt gctgcagaac cagaagaagg tggagttcaa gatcgacatc    960
gtggtgctgg cc                                                        972
```

<210> SEQ ID NO 49
<211> LENGTH: 324
<212> TYPE: PRT
<213> ORGANISM: Artificial Sequence
<220> FEATURE:
<223> OTHER INFORMATION: Synthetic

<400> SEQUENCE: 49

```
Gln Val Gln Leu Val Gln Ser Gly Gly Gly Leu Val Gln Pro Gly Gly
  1               5                  10                  15

Ser Leu Arg Leu Ser Cys Ala Ala Ser Ala Phe Asp Phe Ser Asp Tyr
             20                  25                  30

Glu Met Ser Trp Val Arg Glu Ala Pro Gly Lys Gly Leu Glu Trp Ile
         35                  40                  45

Gly Glu Ile Asn Asp Ser Gly Asn Thr Ile Tyr Asn Pro Ser Leu Lys
     50                  55                  60

Ser Arg Val Thr Ile Ser Arg Asp Asn Ser Lys Asn Thr Leu Tyr Leu
 65                  70                  75                  80

Gln Met Asn Thr Leu Arg Ala Glu Asp Thr Ala Ile Tyr Tyr Cys Ala
                 85                  90                  95

Ile Tyr Gly Gly Asn Ser Gly Gly Glu Tyr Trp Gly Gln Gly Thr Leu
            100                 105                 110

Val Thr Val Ser Ser Gly Pro Glu Gly Gly Ser Glu Gly Gly Gly
        115                 120                 125

Ser Glu Gly Gly Gly Ser Glu Gly Gly Ser Gly Gly Ser Gly
    130                 135                 140

Ser Gly Lys Lys Val Val Leu Gly Lys Lys Gly Asp Thr Val Glu Leu
145                 150                 155                 160

Thr Cys Thr Ala Ser Gln Lys Lys Ser Ile Gln Phe His Trp Lys Asn
                165                 170                 175

Ser Asn Gln Ile Lys Ile Leu Gly Asn Gln Gly Ser Phe Leu Thr Lys
            180                 185                 190

Gly Pro Ser Lys Leu Asn Asp Arg Ala Asp Ser Arg Arg Ser Leu Trp
        195                 200                 205

Asp Gln Gly Asn Phe Pro Leu Ile Ile Lys Asn Leu Lys Ile Glu Asp
    210                 215                 220

Ser Asp Thr Tyr Ile Cys Glu Val Glu Asp Gln Lys Glu Glu Val Gln
225                 230                 235                 240

Leu Leu Val Phe Gly Leu Thr Ala Asn Ser Asp Thr His Leu Leu Gln
                245                 250                 255

Gly Gln Ser Leu Thr Leu Thr Leu Glu Ser Pro Pro Gly Ser Ser Pro
            260                 265                 270

Ser Val Gln Cys Arg Ser Pro Arg Gly Lys Asn Ile Gln Gly Gly Lys
        275                 280                 285

Thr Leu Ser Val Ser Gln Leu Glu Leu Gln Asp Ser Gly Thr Trp Thr
```

```
              290                 295                 300
Cys Thr Val Leu Gln Asn Gln Lys Lys Val Glu Phe Lys Ile Asp Ile
305                 310                 315                 320

Val Val Leu Ala

<210> SEQ ID NO 50
<211> LENGTH: 1659
<212> TYPE: DNA
<213> ORGANISM: Artificial Sequence
<220> FEATURE:
<223> OTHER INFORMATION: Synthetic

<400> SEQUENCE: 50
caggtgcagc tggtgcagtc tgggggaggc ttggtacagc ctggagggtc cctgagactc      60
tcctgtgcag cctctgcttt cgatttctct gattatgaaa tgagctgggt ccgccaggct     120
ccagggaagg gctggagtg gattgggaa atcaatgata gtggaaacac catttacaat       180
ccgtccctca agagtcgagt caccatctcc agagacaatt ccaagaacac gctgtatctg     240
caaatgaaca ccctgagagc cgaggacaca gccatatatt actgtgcgat atatggtggt     300
aactccgggg gagagtactg gggccagggc accctggtca ccgtctcctc agggcccgag     360
ggtggtggct ctgagggtgg cggttctgag ggtggcggct ctgaggagg cggttccggt      420 ggtggctctg gttccggtaa gaaggtggtg ctgggcaaga agggcgacac cgtggagctg     480
acctgcaccg ccagccagaa gagagcatc cagttccact ggaagaacag caaccagatc     540
aagatcctgg caaccaggg cagcttcctg accaagggac ctagcaagct gaacgacagg     600
gcagacagcc ggcggagcct gtgggaccag ggaaacttcc cactgatcat caagaacctg     660
aagatcgagg acagcgacac ctacatctgc gaggtgagg accagaagga ggaggtgcag      720
ctgctggtgt tcggcctgac cgccaacagc gacacccacc tgctgcaggg ccagagcctg     780
accctgaccc tggagagccc accaggaagc agcccaagcg tgcagtgccg gagcccaagg     840
ggcaagaaca tccagggagg caagaccctg agcgtgagcc agctggagct gcaggacagc     900
ggcacctgga cctgcaccgt gctgcagaac cagaagaagg tggagttcaa gatcgacatc     960
gtggtgctgg ccgggcccga caaaactcac acatgcccac cgtgcccagc acctgaactc    1020
ctggggggac cgtcagtctt cctcttcccc ccaaaaccca aggacaccct catgatctcc    1080
cggacccctg aggtcacatg cgtggtggtg gacgtgagcc acgaagaccc tgaggtcaag    1140
ttcaactggt acgtggacgg cgtggaggtg cataatgcca agacaaagcc gcgggaggag    1200
cagtacaaca gcacgtaccg tgtggtcagc gtcctcaccg tcctgcacca ggactggctg    1260
aatggcaagg agtacaagtg caaggtctcc aacaaagccc tcccagcccc catcgagaaa    1320
accatctcca aagccaaagg gcagccccga gaaccacagg tgtacaccct gcccccatcc    1380
cgggatgagc tgaccaagaa ccaggtcagc ctgacctgcc tggtcaaagg cttctatccc    1440
agcgacatcg ccgtggagtg ggagagcaat gggcagccgg agaacaacta caagaccacg    1500
cctcccgtgc tggactccga cggctccttc ttcctctaca gcaagctcac cgtggacaag    1560
agcaggtggc agcaggggaa cgtcttctca tgctccgtga tgcatgaggc tctgcacaac    1620
cactacacgc agaagagcct ctccctgtct ccgggtaaa                           1659

<210> SEQ ID NO 51
<211> LENGTH: 553
<212> TYPE: PRT
<213> ORGANISM: Artificial Sequence
<220> FEATURE:
```

<223> OTHER INFORMATION: Synthetic

<400> SEQUENCE: 51

```
Gln Val Gln Leu Val Gln Ser Gly Gly Gly Leu Val Gln Pro Gly Gly
 1               5                  10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Pro Glu Gly Gly Ser Glu Gly Gly Gly
        115                 120                 125

Ser Glu Gly Gly Ser Glu Gly Gly Ser Gly Gly Ser Gly
    130                 135                 140

Ser Gly Lys Lys Val Val Leu Gly Lys Lys Gly Asp Thr Val Glu Leu
145                 150                 155                 160

Thr Cys Thr Ala Ser Gln Lys Lys Ser Ile Gln Phe His Trp Lys Asn
                165                 170                 175

Ser Asn Gln Ile Lys Ile Leu Gly Asn Gln Gly Ser Phe Leu Thr Lys
            180                 185                 190

Gly Pro Ser Lys Leu Asn Asp Arg Ala Asp Ser Arg Arg Ser Leu Trp
        195                 200                 205

Asp Gln Gly Asn Phe Pro Leu Ile Ile Lys Asn Leu Lys Ile Glu Asp
    210                 215                 220

Ser Asp Thr Tyr Ile Cys Glu Val Glu Asp Gln Lys Glu Glu Val Gln
225                 230                 235                 240

Leu Leu Val Phe Gly Leu Thr Ala Asn Ser Asp Thr His Leu Leu Gln
                245                 250                 255

Gly Gln Ser Leu Thr Leu Thr Leu Glu Ser Pro Pro Gly Ser Ser Pro
            260                 265                 270

Ser Val Gln Cys Arg Ser Pro Arg Gly Lys Asn Ile Gln Gly Gly Lys
        275                 280                 285

Thr Leu Ser Val Ser Gln Leu Glu Leu Gln Asp Ser Gly Thr Trp Thr
    290                 295                 300

Cys Thr Val Leu Gln Asn Gln Lys Lys Val Glu Phe Lys Ile Asp Ile
305                 310                 315                 320

Val Val Leu Ala Gly Pro Asp Lys Thr His Thr Cys Pro Pro Cys Pro
                325                 330                 335

Ala Pro Glu Leu Leu Gly Gly Pro Ser Val Phe Leu Phe Pro Pro Lys
            340                 345                 350

Pro Lys Asp Thr Leu Met Ile Ser Arg Thr Pro Glu Val Thr Cys Val
        355                 360                 365

Val Val Asp Val Ser His Glu Asp Pro Glu Val Lys Phe Asn Trp Tyr
    370                 375                 380

Val Asp Gly Val Glu Val His Asn Ala Lys Thr Lys Pro Arg Glu Glu
385                 390                 395                 400
```

Gln Tyr Asn Ser Thr Tyr Arg Val Val Ser Val Leu Thr Val Leu His
                405                 410                 415

Gln Asp Trp Leu Asn Gly Lys Glu Tyr Lys Cys Lys Val Ser Asn Lys
            420                 425                 430

Ala Leu Pro Ala Pro Ile Glu Lys Thr Ile Ser Lys Ala Lys Gly Gln
        435                 440                 445

Pro Arg Glu Pro Gln Val Tyr Thr Leu Pro Pro Ser Arg Asp Glu Leu
    450                 455                 460

Thr Lys Asn Gln Val Ser Leu Thr Cys Leu Val Lys Gly Phe Tyr Pro
465                 470                 475                 480

Ser Asp Ile Ala Val Glu Trp Glu Ser Asn Gly Gln Pro Glu Asn Asn
                485                 490                 495

Tyr Lys Thr Thr Pro Pro Val Leu Asp Ser Asp Gly Ser Phe Phe Leu
            500                 505                 510

Tyr Ser Lys Leu Thr Val Asp Lys Ser Arg Trp Gln Gln Gly Asn Val
        515                 520                 525

Phe Ser Cys Ser Val Met His Glu Ala Leu His Asn His Tyr Thr Gln
    530                 535                 540

Lys Ser Leu Ser Leu Ser Pro Gly Lys
545                 550

<210> SEQ ID NO 52
<211> LENGTH: 1659
<212> TYPE: DNA
<213> ORGANISM: Artificial Sequence
<220> FEATURE:
<223> OTHER INFORMATION: Synthetic

<400> SEQUENCE: 52
caggtgcagc tggtgcagtc tggggggaggc ttggtacagc ctggagggtc cctgagactc        60
tcctgtgcag cctctgcttt cgatttctct gattatgaaa tgagctgggt ccgcgaggct       120
ccagggaagg gctggagtg gattggggaa atcaatgata gtggaaacac catttacaat       180
ccgtccctca agagtcgagt caccatctcc agagacaatt ccaagaacac actgtatctg       240
caaatgaaca ccctgagagc cgaggacaca gccatatatt actgtgcgat atatggtggt       300
aactccgggg gagagtactg gggccagggc accctggtca ccgtctcctc agggcccgag       360
ggtggtggct ctgagggtgg cggttctgag gtggcggct ctgagggagg cggttccggt       420
ggtggctctg gttccggtaa gaaggtggtg ctgggcaaga agggcgacac cgtggagctg       480
acctgcaccg ccagccagaa gaagagcatc cagttccact ggaagaacag caaccagatc       540
aagatcctgg gcaaccaggg cagcttcctg accaagggac tagcaagct gaacgacagg       600 gcagacagcc ggcggagcct gtgggaccag ggaaacttcc cactgatcat caagaacctg       660
aagatcgagg acagcgacac ctacatctgc gaggtggagg accagaagga ggaggtgcag       720
ctgctggtgt tcggcctgac cgccaacagc gacacccacc tgctgcaggg ccagagcctg       780
accctgaccc tggagagccc accaggaagc agcccaagcg tgcagtgccg agcccaagg       840 ggcaagaaca tccagggagg caagaccctg agcgtgagcc agctggagct gcaggacagc       900
ggcacctgga cctgcaccgt gctgcagaac cagaagaagg tggagttcaa gatcgacatc       960
gtggtgctgg ccgggcccga caaaactcac acatgcccac cgtgcccagc acctgaactc      1020
ctggggggac cgtcagtctt cctcttcccc ccaaaaccca aggacaccct catgatctcc      1080
cggacccctg aggtcacatg cgtggtggtg gacgtgagcc acgaagaccc tgaggtcaag      1140
ttcaactggt acgtggacgg cgtggaggtg cataatgcca agacaaagcc gcgggaggag      1200

```
cagtacaaca gcacgtaccg tgtggtcagc gtcctcaccg tcctgcacca ggactggctg   1260
aatggcaagg agtacaagtg caaggtctcc aacaaagccc tcccagcccc catcgagaaa   1320
accatctcca agccaaagg gcagccccga gaaccacagg tgtacaccct gcccccatcc    1380
cgggatgagc tgaccaagaa ccaggtcagc ctgacctgcc tggtcaaagg cttctatccc   1440
agcgacatcg ccgtggagtg ggagagcaat gggcagccgg agaacaacta caagaccacg   1500
cctcccgtgc tggactccga cggctccttc ttcctctaca gcaagctcac cgtggacaag   1560
agcaggtggc agcaggggaa cgtcttctca tgctccgtga tgcatgaggc tctgcacaac   1620
cactacacgc agaagagcct ctccctgtct ccgggtaaa                          1659
```

```
<210> SEQ ID NO 53
<211> LENGTH: 553
<212> TYPE: PRT
<213> ORGANISM: Artificial Sequence
<220> FEATURE:
<223> OTHER INFORMATION: Synthetic

<400> SEQUENCE: 53

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Gln Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Pro Glu Gly Gly Gly Ser Glu Gly Gly Gly
        115                 120                 125

Ser Glu Gly Gly Ser Glu Gly Gly Ser Gly Gly Ser Gly
    130                 135                 140

Ser Gly Lys Lys Val Val Leu Gly Lys Lys Gly Asp Thr Val Glu Leu
145                 150                 155                 160

Thr Cys Thr Ala Ser Gln Lys Lys Ser Ile Gln Phe His Trp Lys Asn
                165                 170                 175

Ser Asn Gln Ile Lys Ile Leu Gly Asn Gln Gly Ser Phe Leu Thr Lys
            180                 185                 190

Gly Pro Ser Lys Leu Asn Asp Arg Ala Asp Ser Arg Arg Ser Leu Trp
        195                 200                 205

Asp Gln Gly Asn Phe Pro Leu Ile Ile Lys Asn Leu Lys Ile Glu Asp
    210                 215                 220

Ser Asp Thr Tyr Ile Cys Glu Val Glu Asp Gln Lys Glu Glu Val Gln
225                 230                 235                 240

Leu Leu Val Phe Gly Leu Thr Ala Asn Ser Asp Thr His Leu Leu Gln
                245                 250                 255

Gly Gln Ser Leu Thr Leu Thr Leu Glu Ser Pro Pro Gly Ser Ser Pro
            260                 265                 270

Ser Val Gln Cys Arg Ser Pro Arg Gly Lys Asn Ile Gln Gly Gly Lys
```

```
            275                 280                 285
Thr Leu Ser Val Ser Gln Leu Glu Leu Gln Asp Ser Gly Thr Trp Thr
    290                 295                 300
Cys Thr Val Leu Gln Asn Gln Lys Val Glu Phe Lys Ile Asp Ile
305                 310                 315                 320
Val Val Leu Ala Gly Pro Asp Lys Thr His Thr Cys Pro Pro Cys Pro
                325                 330                 335
Ala Pro Glu Leu Leu Gly Gly Pro Ser Val Phe Leu Phe Pro Pro Lys
            340                 345                 350
Pro Lys Asp Thr Leu Met Ile Ser Arg Thr Pro Glu Val Thr Cys Val
                355                 360                 365
Val Val Asp Val Ser His Glu Asp Pro Glu Val Lys Phe Asn Trp Tyr
            370                 375                 380
Val Asp Gly Val Glu Val His Asn Ala Lys Thr Lys Pro Arg Glu Glu
385                 390                 395                 400
Gln Tyr Asn Ser Thr Tyr Arg Val Val Ser Val Leu Thr Val Leu His
                405                 410                 415
Gln Asp Trp Leu Asn Gly Lys Glu Tyr Lys Cys Lys Val Ser Asn Lys
            420                 425                 430
Ala Leu Pro Ala Pro Ile Glu Lys Thr Ile Ser Lys Ala Lys Gly Gln
                435                 440                 445
Pro Arg Glu Pro Gln Val Tyr Thr Leu Pro Pro Ser Arg Asp Glu Leu
            450                 455                 460
Thr Lys Asn Gln Val Ser Leu Thr Cys Leu Val Lys Gly Phe Tyr Pro
465                 470                 475                 480
Ser Asp Ile Ala Val Glu Trp Glu Ser Asn Gly Gln Pro Glu Asn Asn
                485                 490                 495
Tyr Lys Thr Thr Pro Pro Val Leu Asp Ser Asp Gly Ser Phe Phe Leu
            500                 505                 510
Tyr Ser Lys Leu Thr Val Asp Lys Ser Arg Trp Gln Gln Gly Asn Val
            515                 520                 525
Phe Ser Cys Ser Val Met His Glu Ala Leu His Asn His Tyr Thr Gln
            530                 535                 540
Lys Ser Leu Ser Leu Ser Pro Gly Lys
545                 550

<210> SEQ ID NO 54
<211> LENGTH: 43
<212> TYPE: DNA
<213> ORGANISM: Artificial Sequence
<220> FEATURE:
<223> OTHER INFORMATION: Synthetic

<400> SEQUENCE: 54
tggtttcgct accgtggccc aggcggccca ggtgcagctg gtg                           43

<210> SEQ ID NO 55
<211> LENGTH: 41
<212> TYPE: DNA
<213> ORGANISM: Artificial Sequence
<220> FEATURE:
<223> OTHER INFORMATION: Synthetic

<400> SEQUENCE: 55
gtcgccgtgg tggtggtggt ggtggccggc ctggccactt g                             41

<210> SEQ ID NO 56
```

<211> LENGTH: 1581
<212> TYPE: DNA
<213> ORGANISM: Artificial Sequence
<220> FEATURE:
<223> OTHER INFORMATION: Synthetic

<400> SEQUENCE: 56

```
gaggtggtgc tgggcaacgt gaccgagaac ttcaacatgt ggaagaacaa catggtggag    60
cagatgcacg aggacatcat cagcctgtgg gaccagagcc tgaagccctg cgtgaagctg   120
accccctgt gcgtgaccct gaactgcacc gacgagctgc ggaacggcac ctacgccaac   180
gtgaccgtga ccgagaaggg cgagatcaag aactgcagct caacatcac caccgccatc   240
cgggacaagg tgcagaagac ctacgccctg ttctaccggc tggacgtggt gcccatcgac   300
aacaaccacg gcaacagcag cagcaactac agcaactacc ggctgatcaa ctgcaacacc   360
agcgtgatca cccaggcctg cccaaaggtg agcttcgagc caatcccaat ccactactgc   420
gcaccagcag gcttcgccat cctgaagtgc aacaacaaga gttcaacgg aaccggcccc   480
tgcaagaacg tgagcaccgt gcagtgcacc cacggaatca ggccagtggt gagcacccag   540
ctgctgctga cggcagcct ggcagaggag gaggtggtca tccggagcga aacttcacc   600
gacaacgcca agaccatcat cgtgcagctg aacgacagcg tgatcatcaa ctgcacccgg   660
cccaacaaca cacccggaa gggcatcacc atcggacctg gccgggtgtt ctacaccggc   720
gagatcgtgg gcgacatccg gcaggtgcac tgcaacctga gcgcgccaa gtggaacagc   780
accctgaagc aggtggtgac caagctgcgg gagcagttcg gcaacaagac catcgtgttc   840
aaccagagca gcggcggcga ccccgagatc gtgatgcaca gcttcaactg cggcggcgag   900
ttcttttttct gcaacaccac ccagctgttc aacagcacct ggaacatcaa cggcacctgg   960
cacggcacca ccgtgagcaa caagaccatc atcctgccct gccggatcaa gcagatcatc  1020
aacatgtggc aggaagtggg caaggcaatg tacgcaccac caatcagggg acagatcagg  1080
tgcagcagca acatcaccgg actgctgctg accaggacg gaggaaacaa caacagcacc  1140
accgagatct tccggccagg aggaggcgac atgagggaca ctggcggag cgagctgtac  1200
aagtacaagg tggtgaagat cgaggggagga ggaggatccg gcggaggagg atccggagga  1260
ggaggaagcg gtggaggcgg ttcaaagaag gtggtgtacg gcaagaaggg cgacaccgtg  1320
gagctgacct gcaccgccag ccagaagaag aacatccagt ccactgaa gaacagcaac  1380
cagatcaaga tcctgggcaa ccagggcagc ttcctgacca agggacctag caagctgaac  1440
gacagggcag acagccggcg gagcctgtgg gaccagggaa acttcccact gatcatcaag  1500
aacctgaagc cagaggacag cgacacctac atctgcgagg tggaggacca gaaggaggag  1560
gtgcagctgg tagtggtagg c                                              1581
```

<210> SEQ ID NO 57
<211> LENGTH: 527
<212> TYPE: PRT
<213> ORGANISM: Artificial Sequence
<220> FEATURE:
<223> OTHER INFORMATION: Synthetic

<400> SEQUENCE: 57

Glu Val Val Leu Gly Asn Val Thr Glu Asn Phe Asn Met Trp Lys Asn
1               5                   10                  15

Asn Met Val Glu Gln Met His Glu Asp Ile Ile Ser Leu Trp Asp Gln
            20                  25                  30

Ser Leu Lys Pro Cys Val Lys Leu Thr Pro Leu Cys Val Thr Leu Asn

-continued

```
                35                  40                  45
Cys Thr Asp Glu Leu Arg Asn Gly Thr Tyr Ala Asn Val Thr Val Thr
 50                  55                  60

Glu Lys Gly Glu Ile Lys Asn Cys Ser Phe Asn Ile Thr Thr Ala Ile
 65                  70                  75                  80

Arg Asp Lys Val Gln Lys Thr Tyr Ala Leu Phe Tyr Arg Leu Asp Val
                 85                  90                  95

Val Pro Ile Asp Asn Asn His Gly Asn Ser Ser Asn Tyr Ser Asn
                100                 105                 110

Tyr Arg Leu Ile Asn Cys Asn Thr Ser Val Ile Thr Gln Ala Cys Pro
                115                 120                 125

Lys Val Ser Phe Glu Pro Ile Pro Ile His Tyr Cys Ala Pro Ala Gly
            130                 135                 140

Phe Ala Ile Leu Lys Cys Asn Asn Lys Phe Asn Gly Thr Gly Pro
145                 150                 155                 160

Cys Lys Asn Val Ser Thr Val Gln Cys Thr His Gly Ile Arg Pro Val
                165                 170                 175

Val Ser Thr Gln Leu Leu Leu Asn Gly Ser Leu Ala Glu Glu Glu Val
                180                 185                 190

Val Ile Arg Ser Glu Asn Phe Thr Asp Asn Ala Lys Thr Ile Ile Val
            195                 200                 205

Gln Leu Asn Asp Ser Val Ile Ile Asn Cys Thr Arg Pro Asn Asn Asn
210                 215                 220

Thr Arg Lys Gly Ile Thr Ile Gly Pro Gly Arg Val Phe Tyr Thr Gly
225                 230                 235                 240

Glu Ile Val Gly Asp Ile Arg Gln Val His Cys Asn Leu Ser Ser Ala
                245                 250                 255

Lys Trp Asn Ser Thr Leu Lys Gln Val Val Thr Lys Leu Arg Glu Gln
                260                 265                 270

Phe Gly Asn Lys Thr Ile Val Phe Asn Gln Ser Ser Gly Gly Asp Pro
            275                 280                 285

Glu Ile Val Met His Ser Phe Asn Cys Gly Gly Glu Phe Phe Cys
290                 295                 300

Asn Thr Thr Gln Leu Phe Asn Ser Thr Trp Asn Ile Asn Gly Thr Trp
305                 310                 315                 320

His Gly Thr Thr Val Ser Asn Lys Thr Ile Ile Leu Pro Cys Arg Ile
                325                 330                 335

Lys Gln Ile Ile Asn Met Trp Gln Glu Val Gly Lys Ala Met Tyr Ala
                340                 345                 350

Pro Pro Ile Arg Gly Gln Ile Arg Cys Ser Ser Asn Ile Thr Gly Leu
            355                 360                 365

Leu Leu Thr Arg Asp Gly Gly Asn Asn Asn Ser Thr Thr Glu Ile Phe
            370                 375                 380

Arg Pro Gly Gly Gly Asp Met Arg Asp Asn Trp Arg Ser Glu Leu Tyr
385                 390                 395                 400

Lys Tyr Lys Val Val Lys Ile Glu Gly Gly Gly Ser Gly Gly Gly
                    405                 410                 415

Gly Ser Gly Gly Gly Ser Gly Gly Gly Ser Lys Val Val
                420                 425                 430

Tyr Gly Lys Lys Gly Asp Thr Val Glu Leu Thr Cys Thr Ala Ser Gln
            435                 440                 445

Lys Lys Asn Ile Gln Phe His Trp Lys Asn Ser Asn Gln Ile Lys Ile
            450                 455                 460
```

Leu Gly Asn Gln Gly Ser Phe Leu Thr Lys Gly Pro Ser Lys Leu Asn
465                 470                 475                 480

Asp Arg Ala Asp Ser Arg Arg Ser Leu Trp Asp Gln Gly Asn Phe Pro
            485                 490                 495

Leu Ile Ile Lys Asn Leu Lys Pro Glu Asp Ser Asp Thr Tyr Ile Cys
        500                 505                 510

Glu Val Glu Asp Gln Lys Glu Glu Val Gln Leu Val Val Val Gly
    515                 520                 525

<210> SEQ ID NO 58
<211> LENGTH: 1818
<212> TYPE: DNA
<213> ORGANISM: Artificial Sequence
<220> FEATURE:
<223> OTHER INFORMATION: Synthetic

<400> SEQUENCE: 58

| | |
|---|---|
| gaggtggtgc tgggcaacgt gaccgagaac ttcaacatgt ggaagaacaa catggtggag | 60 |
| cagatgcacg aggacatcat cagcctgtgg gaccagagcc tgaagccctg cgtgaagctg | 120 |
| accccccctgt gcgtgaccct gaactgcacc gacgagctgc ggaacggcac ctacgccaac | 180 |
| gtgaccgtga ccgagaaggg cgagatcaag aactgcagct tcaacatcac caccgccatc | 240 |
| cgggacaagg tgcagaagac ctacgccctg ttctaccggc tggacgtggt gcccatcgac | 300 |
| aacaaccacg gcaacagcag cagcaactac agcaactacc ggctgatcaa ctgcaacacc | 360 |
| agcgtgatca cccaggcctg cccaaaggtg agcttcgagc caatcccaat ccactactgc | 420 |
| gcaccagcag gcttcgccat cctgaagtgc aacaacaaga agttcaacgg aaccggcccc | 480 |
| tgcaagaacg tgagcaccgt gcagtgcacc cacggaatca ggccagtggt gagcacccag | 540 |
| ctgctgctga cggcagcct gcagaggag gaggtggtca tccggagcga aacttcacc | 600 |
| gacaacgcca agaccatcat cgtgcagctg aacgacagcg tgatcatcaa ctgcacccgg | 660 |
| cccaacaaca cacccggaa gggcatcacc atcggacctg gccgggtgtt ctacaccggc | 720 |
| gagatcgtgg gcgacatccg gcaggtgcac tgcaacctga gcagcgccaa gtggaacagc | 780 |
| accctgaagc aggtggtgac caagctgcgg gagcagttcg gcaacaagac catcgtgttc | 840 |
| aaccagagca gcggcggcga ccccgagatc gtgatgcaca gcttcaactg cggcggcgag | 900 |
| ttcttttct gcaacaccac ccagctgttc aacagcacct ggaacatcaa cggcacctgg | 960 |
| cacggcacca ccgtgagcaa caagaccatc atcctgccct gccggatcaa gcagatcatc | 1020 |
| aacatgtggc aggaagtggg caaggcaatg tacgcaccac caatcagggg acagatcagg | 1080 |
| tgcagcagca acatcaccgg actgctgctg accagggacg aggaaacaa caacagcacc | 1140 |
| accgagatct tccggccagg aggaggcgac atgagggaca ctggcggag cgagctgtac | 1200 |
| aagtacaagg tggtgaagat cgagggagga ggaggatccg gcggaggagg atccggagga | 1260 |
| ggaggaagcg gtgaggcgg ttcaaagaag gtggtgctgg gcaagaaggg cgacaccgtg | 1320 |
| gagctgacct gcaccgccag ccagaagaag agcatccagt tccactggaa gaacagcaac | 1380 |
| cagatcaaga tcctgggcaa ccagggcagc ttcctgacca agggacctag caagctgaac | 1440 |
| gacagggcag acagccggcg gagcctgtgg gaccaggaa acttcccact gatcatcaag | 1500 |
| aacctgaaga tcgaggacag cgacacctac atctgcgagg tggaggacca gaaggaggag | 1560 |
| gtgcagctgc tggtgttcgg cctgaccgcc aacagcgaca cccacctgct gcagggccag | 1620 |
| agcctgaccc tgaccctgga gagcccacca ggaagcagcc caagcgtgca gtgccggagc | 1680 |

```
ccaaggggca agaacatcca gggaggcaag accctgagcg tgagccagct ggagctgcag    1740
gacagcggca cctggacctg caccgtgctg cagaaccaga agaaggtgga gttcaagatc    1800
gacatcgtgg tgctggcc                                                  1818
```

<210> SEQ ID NO 59
<211> LENGTH: 606
<212> TYPE: PRT
<213> ORGANISM: Artificial Sequence
<220> FEATURE:
<223> OTHER INFORMATION: Synthetic

<400> SEQUENCE: 59

```
Glu Val Val Leu Gly Asn Val Thr Glu Asn Phe Asn Met Trp Lys Asn
1               5                   10                  15

Asn Met Val Glu Gln Met His Glu Asp Ile Ile Ser Leu Trp Asp Gln
            20                  25                  30

Ser Leu Lys Pro Cys Val Lys Leu Thr Pro Leu Cys Val Thr Leu Asn
        35                  40                  45

Cys Thr Asp Glu Leu Arg Asn Gly Thr Tyr Ala Asn Val Thr Val Thr
    50                  55                  60

Glu Lys Gly Glu Ile Lys Asn Cys Ser Phe Asn Ile Thr Thr Ala Ile
65                  70                  75                  80

Arg Asp Lys Val Gln Lys Thr Tyr Ala Leu Phe Tyr Arg Leu Asp Val
                85                  90                  95

Val Pro Ile Asp Asn Asn His Gly Asn Ser Ser Asn Tyr Ser Asn
            100                 105                 110

Tyr Arg Leu Ile Asn Cys Asn Thr Ser Val Ile Thr Gln Ala Cys Pro
        115                 120                 125

Lys Val Ser Phe Glu Pro Ile Pro Ile His Tyr Cys Ala Pro Ala Gly
    130                 135                 140

Phe Ala Ile Leu Lys Cys Asn Asn Lys Lys Phe Asn Gly Thr Gly Pro
145                 150                 155                 160

Cys Lys Asn Val Ser Thr Val Gln Cys Thr His Gly Ile Arg Pro Val
                165                 170                 175

Val Ser Thr Gln Leu Leu Leu Asn Gly Ser Leu Ala Glu Glu Glu Val
            180                 185                 190

Val Ile Arg Ser Glu Asn Phe Thr Asp Asn Ala Lys Thr Ile Ile Val
        195                 200                 205

Gln Leu Asn Asp Ser Val Ile Ile Asn Cys Thr Arg Pro Asn Asn Asn
    210                 215                 220

Thr Arg Lys Gly Ile Thr Ile Gly Pro Gly Arg Val Phe Tyr Thr Gly
225                 230                 235                 240

Glu Ile Val Gly Asp Ile Arg Gln Val His Cys Asn Leu Ser Ser Ala
                245                 250                 255

Lys Trp Asn Ser Thr Leu Lys Gln Val Val Thr Lys Leu Arg Glu Gln
            260                 265                 270

Phe Gly Asn Lys Thr Ile Val Phe Asn Gln Ser Ser Gly Gly Asp Pro
        275                 280                 285

Glu Ile Val Met His Ser Phe Asn Cys Gly Gly Glu Phe Phe Cys
    290                 295                 300

Asn Thr Thr Gln Leu Phe Asn Ser Thr Trp Asn Ile Asn Gly Thr Trp
305                 310                 315                 320

His Gly Thr Thr Val Ser Asn Lys Thr Ile Ile Leu Pro Cys Arg Ile
                325                 330                 335
```

Lys Gln Ile Ile Asn Met Trp Gln Glu Val Gly Lys Ala Met Tyr Ala
                340                 345                 350

Pro Pro Ile Arg Gly Gln Ile Arg Cys Ser Ser Asn Ile Thr Gly Leu
            355                 360                 365

Leu Leu Thr Arg Asp Gly Gly Asn Asn Asn Ser Thr Thr Glu Ile Phe
        370                 375                 380

Arg Pro Gly Gly Gly Asp Met Arg Asp Asn Trp Arg Ser Glu Leu Tyr
385                 390                 395                 400

Lys Tyr Lys Val Val Lys Ile Glu Gly Gly Gly Ser Gly Gly
                405                 410                 415

Gly Ser Gly Gly Gly Ser Gly Gly Gly Ser Lys Lys Val Val
            420                 425                 430

Leu Gly Lys Lys Gly Asp Thr Val Glu Leu Thr Cys Thr Ala Ser Gln
        435                 440                 445

Lys Lys Ser Ile Gln Phe His Trp Lys Asn Ser Asn Gln Ile Lys Ile
    450                 455                 460

Leu Gly Asn Gln Gly Ser Phe Leu Thr Lys Gly Pro Ser Lys Leu Asn
465                 470                 475                 480

Asp Arg Ala Asp Ser Arg Arg Ser Leu Trp Asp Gln Gly Asn Phe Pro
                485                 490                 495

Leu Ile Ile Lys Asn Leu Lys Ile Glu Asp Ser Asp Thr Tyr Ile Cys
            500                 505                 510

Glu Val Glu Asp Gln Lys Glu Glu Val Gln Leu Leu Val Phe Gly Leu
        515                 520                 525

Thr Ala Asn Ser Asp Thr His Leu Leu Gln Gly Gln Ser Leu Thr Leu
530                 535                 540

Thr Leu Glu Ser Pro Pro Gly Ser Ser Pro Ser Val Gln Cys Arg Ser
545                 550                 555                 560

Pro Arg Gly Lys Asn Ile Gln Gly Gly Lys Thr Leu Ser Val Ser Gln
                565                 570                 575

Leu Glu Leu Gln Asp Ser Gly Thr Trp Thr Cys Thr Val Leu Gln Asn
            580                 585                 590

Gln Lys Lys Val Glu Phe Lys Ile Asp Ile Val Val Leu Ala
        595                 600                 605

<210> SEQ ID NO 60
<211> LENGTH: 693
<212> TYPE: DNA
<213> ORGANISM: Artificial Sequence
<220> FEATURE:
<223> OTHER INFORMATION: Synthetic

<400> SEQUENCE: 60
caggtgcagc tggtgcagtc tgggggaggc ttggtacagc ctggagggtc cctgagactc     60
tcctgtgcag cctctgcttt cgatttctct gattatgaaa tgagctgggt ccgcgaggct    120
ccagggaagg ggctggagtg gattggggaa atcaatgata gtggaaacac catttacaat    180
ccgtccctca agagtcgagt caccatctcc agagacaatt ccaagaacac actgtatctg    240
caaatgaaca ccctgagagc cgaggacaca gccatatatt actgtgcgat atatggtggt    300
aactccgggg gagagtactg gggccagggc accctggtca ccgtctcctc aggagggggt    360
ggcagcggag gcgggggaag tggcggtgga gggagcaaga aggtggtgat cggcaagaag    420
ggcgacaccg tggagctgac ctgcaccgcc agcagaagag agcatcca gttccactgg    480 aagaacagca accagatcaa gatcctgggc aaccagggca gcttcctgac caagggacct    540

```
agcaagctga acgacagggt agacagccgg cggagcctgt gggaccaggg aaacttccca    600
ctgatcatca agaacctgaa gcctgaggac agcgacacct acatctgcga ggtggaggac    660
cagaaggagg aggtgcagct gatagtgcta ggc                                 693
```

<210> SEQ ID NO 61
<211> LENGTH: 231
<212> TYPE: PRT
<213> ORGANISM: Artificial Sequence
<220> FEATURE:
<223> OTHER INFORMATION: Synthetic

<400> SEQUENCE: 61

```
Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Lys Lys Val Val Ile Gly Lys Lys Gly Asp Thr Val
    130                 135                 140

Glu Leu Thr Cys Thr Ala Ser Gln Lys Lys Ser Ile Gln Phe His Trp
145                 150                 155                 160

Lys Asn Ser Asn Gln Ile Lys Ile Leu Gly Asn Gln Gly Ser Phe Leu
                165                 170                 175

Thr Lys Gly Pro Ser Lys Leu Asn Asp Arg Val Asp Ser Arg Arg Ser
            180                 185                 190

Leu Trp Asp Gln Gly Asn Phe Pro Leu Ile Ile Lys Asn Leu Lys Pro
        195                 200                 205

Glu Asp Ser Asp Thr Tyr Ile Cys Glu Val Glu Asp Gln Lys Glu Glu
    210                 215                 220

Val Gln Leu Ile Val Leu Gly
225                 230
```

<210> SEQ ID NO 62
<211> LENGTH: 738
<212> TYPE: DNA
<213> ORGANISM: Artificial Sequence
<220> FEATURE:
<223> OTHER INFORMATION: Synthetic

<400> SEQUENCE: 62

```
caggtgcagc tggtgcagtc tgggggaggc ttggtacagc ctggagggtc cctgagactc     60
tcctgtgcag cctctgcttt cgatttctct gattatgaaa tgagctgggt ccgcgaggct    120
ccagggaagg ggctggagtg gattggggaa atcaatgata gtggaaacac catttacaat    180
ccgtccctca agagtcgagt caccatctcc agagacaatt ccaagaacac actgtatctg    240
```

```
caaatgaaca ccctgagagc cgaggacaca gccatatatt actgtgcgat atatggtggt    300
aactccgggg gagagtactg gggccagggc accctggtca ccgtctcctc aggagggggt    360
ggcagcggtg gcgggggaag tggcggtgga gggagcggtg gaggcggttc aggcggaggt    420
ggctctggcg gtggcggatc aaagaaggtg gtgatcggca agaagggcga caccgtggag    480
ctgacctgca ccgccagcca gaagaagagc atccagttcc actggaagaa cagcaaccag    540
atcaagatcc tgggcaacca gggcagcttc ctgaccaagg gacctagcaa gctgaacgac    600
agggtagaca gccggcggag cctgtgggac cagggaaact tcccactgat catcaagaac    660
ctgaagcctg aggacagcga cacctacatc tgcgaggtgg aggaccagaa ggaggaggtg    720
cagctgatag tgctaggc                                                  738
```

<210> SEQ ID NO 63
<211> LENGTH: 246
<212> TYPE: PRT
<213> ORGANISM: Artificial Sequence
<220> FEATURE:
<223> OTHER INFORMATION: Synthetic

<400> SEQUENCE: 63

```
Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Gly Gly Gly Gly Ser Gly Gly Gly Gly Ser Gly Gly
    130                 135                 140

Gly Gly Ser Lys Lys Val Val Ile Gly Lys Lys Gly Asp Thr Val Glu
145                 150                 155                 160

Leu Thr Cys Thr Ala Ser Gln Lys Lys Ser Ile Gln Phe His Trp Lys
                165                 170                 175

Asn Ser Asn Gln Ile Lys Ile Leu Gly Asn Gln Gly Ser Phe Leu Thr
            180                 185                 190

Lys Gly Pro Ser Lys Leu Asn Asp Arg Val Asp Ser Arg Arg Ser Leu
        195                 200                 205

Trp Asp Gln Gly Asn Phe Pro Leu Ile Ile Lys Asn Leu Lys Pro Glu
    210                 215                 220

Asp Ser Asp Thr Tyr Ile Cys Glu Val Glu Asp Gln Lys Glu Glu Val
225                 230                 235                 240

Gln Leu Ile Val Leu Gly
                245
```

<210> SEQ ID NO 64
<211> LENGTH: 783

```
<212> TYPE: DNA
<213> ORGANISM: Artificial Sequence
<220> FEATURE:
<223> OTHER INFORMATION: Synthetic

<400> SEQUENCE: 64
caggtgcagc tggtgcagtc tgggggaggc ttggtacagc ctggagggtc cctgagactc      60
tcctgtgcag cctctgcttt cgatttctct gattatgaaa tgagctgggt ccgcgaggct     120
ccagggaagg ggctggagtg gattggggaa atcaatgata gtggaaacac catttacaat     180
ccgtccctca agagtcgagt caccatctcc agagacaatt ccaagaacac actgtatctg     240
caaatgaaca ccctgagagc cgaggacaca gccatatatt actgtgcgat atatggtggt     300
aactccgggg gagagtactg gggccagggc accctggtca ccgtctcctc aggagggggt     360
ggcagcggtg gcggggaag tggcggtgga gggagcggtg gaggcggttc aggcggaggt     420
ggctctggcg gtggcggatc agggggcgga ggtagtgggg gaggggatc gggtggggga     480 ggcagcaaga aggtggtgat cggcaagaag ggcgacaccg tggagctgac ctgcaccgcc     540
agccagaaga agagcatcca gttccactgg aagaacagca accagatcaa gatcctgggc     600
aaccagggca gcttcctgac caagggacct agcaagctga cgacagggt agacagccgg     660 cggagcctgt gggaccaggg aaacttccca ctgatcatca agaacctgaa gcctgaggac     720
agcgacacct acatctgcga ggtggaggac cagaaggagg aggtgcagct gatagtgcta     780
ggc                                                                    783

<210> SEQ ID NO 65
<211> LENGTH: 261
<212> TYPE: PRT
<213> ORGANISM: Artificial Sequence
<220> FEATURE:
<223> OTHER INFORMATION: Synthetic

<400> SEQUENCE: 65

Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Gly Gly Gly Gly Ser Gly Gly Gly
    130                 135                 140

Gly Gly Ser Gly Gly Gly Gly Ser Gly Gly Gly Gly Ser Gly Gly Gly
145                 150                 155                 160

Gly Ser Lys Lys Val Val Ile Gly Lys Lys Gly Asp Thr Val Glu Leu
                165                 170                 175

Thr Cys Thr Ala Ser Gln Lys Lys Ser Ile Gln Phe His Trp Lys Asn
```

```
                180             185             190
Ser Asn Gln Ile Lys Ile Leu Gly Asn Gln Gly Ser Phe Leu Thr Lys
            195                 200                 205

Gly Pro Ser Lys Leu Asn Asp Arg Val Asp Ser Arg Ser Leu Trp
        210                 215                 220

Asp Gln Gly Asn Phe Pro Leu Ile Ile Lys Asn Leu Lys Pro Glu Asp
225                 230                 235                 240

Ser Asp Thr Tyr Ile Cys Glu Val Glu Asp Gln Lys Glu Glu Val Gln
                245                 250                 255

Leu Ile Val Leu Gly
            260

<210> SEQ ID NO 66
<211> LENGTH: 663
<212> TYPE: DNA
<213> ORGANISM: Artificial Sequence
<220> FEATURE:
<223> OTHER INFORMATION: Synthetic

<400> SEQUENCE: 66
aagaaggtgg tgatcggcaa gaagggcgac accgtggagc tgacctgcac cgccagccag      60
aagaagagca tccagttcca ctggaagaac agcaaccaga tcaagatcct gggcaaccag     120
ggcagcttcc tgaccaaggg acctagcaag ctgaacgaca gggtagacag ccggcggagc     180
ctgtgggacc agggaaactt cccactgatc atcaagaacc tgaagcctga ggacagcgac     240
acctacatct gcgaggtgga ggaccagaag gaggaggtgc agctgatagt gctaggcgga     300
gggggtggca gcggaggcgg gggaagtggc ggtggaggga gcgggcagcc ccgagaacca     360
caggtgtaca ccctgccccc atcccgggat gagctgacca agaaccaggt cagcctgacc     420
tgcctggtca aaggcttcta tcccagcgac atcgccgtgg agtgggagag caatgggcag     480
ccggagaaca actacaagac cacgcctccc gtgctggact ccgacggctc cttcttcctc     540
tacagcaagc tcaccgtgga caagagcagg tggcagcagg gaacgtcttt ctcatgctcc     600
gtgatgcatg aggctctgca caaccactac acgcagaaga gcctctccct gtctccgggt     660
aaa                                                                   663

<210> SEQ ID NO 67
<211> LENGTH: 221
<212> TYPE: PRT
<213> ORGANISM: Artificial Sequence
<220> FEATURE:
<223> OTHER INFORMATION: Synthetic

<400> SEQUENCE: 67

Lys Lys Val Val Ile Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Ile
                85                  90                  95
```

Val Leu Gly Gly Gly Gly Ser Gly Gly Gly Ser Gly Gly Gly
            100                 105                 110

Gly Ser Gly Gln Pro Arg Glu Pro Gln Val Tyr Thr Leu Pro Pro Ser
        115                 120                 125

Arg Asp Glu Leu Thr Lys Asn Gln Val Ser Leu Thr Cys Leu Val Lys
130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly Lys
    210                 215                 220

<210> SEQ ID NO 68
<211> LENGTH: 708
<212> TYPE: DNA
<213> ORGANISM: Artificial Sequence
<220> FEATURE:
<223> OTHER INFORMATION: Synthetic

<400> SEQUENCE: 68
aagaaggtgg tgatcggcaa gaagggcgac accgtggagc tgacctgcac cgccagccag    60
aagaagagca tccagttcca ctggaagaac agcaaccaga tcaagatcct gggcaaccag   120
ggcagcttcc tgaccaaggg acctagcaag ctgaacgaca gggtagacag ccggcggagc   180
ctgtgggacc aggaaaactt ccccactgat catcaagaacc tgaagcctga ggacagcgac   240
acctacatct gcgaggtgga ggaccagaag gaggaggtgc agctgatagt gctaggcgga   300
gggggtggca gcgtggcgg gggaagtggc ggtggaggga gcgtggagg cggttcaggc   360 ggaggtggct ctggcggtgg cggatcaggg cagccccgag aaccacaggt gtacaccctg   420
cccccatccc gggatgagct gaccaagaac caggtcagcc tgacctgcct ggtcaaaggc   480
ttctatccca gcgacatcgc cgtggagtgg gagagcaatg gcagccggga gaacaactac   540
aagaccacgc ctcccgtgct ggactccgac ggctccttct cctctacag caagctcacc   600 gtggacaaga gcaggtggca gcaggggaac gtcttctcat gctccgtgat gcatgaggct   660
ctgcacaacc actacacgca gaagagcctc tccctgtctc cgggtaaa              708

<210> SEQ ID NO 69
<211> LENGTH: 236
<212> TYPE: PRT
<213> ORGANISM: Artificial Sequence
<220> FEATURE:
<223> OTHER INFORMATION: Synthetic

<400> SEQUENCE: 69

Lys Lys Val Val Ile Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Asp Gln Lys Glu Val Gln Leu Ile
                85                  90                  95

Val Leu Gly Gly Gly Gly Ser Gly Gly Gly Ser Gly Gly Gly
            100                 105                 110

Gly Ser Gly Gly Gly Gly Ser Gly Gly Gly Ser Gly Gly Gly
            115                 120                 125

Ser Gly Gln Pro Arg Glu Pro Gln Val Tyr Thr Leu Pro Pro Ser Arg
    130                 135                 140

Asp Glu Leu Thr Lys Asn Gln Val Ser Leu Thr Cys Leu Val Lys Gly
145                 150                 155                 160

Phe Tyr Pro Ser Asp Ile Ala Val Glu Trp Glu Ser Asn Gly Gln Pro
                165                 170                 175

Glu Asn Asn Tyr Lys Thr Thr Pro Pro Val Leu Asp Ser Asp Gly Ser
            180                 185                 190

Phe Phe Leu Tyr Ser Lys Leu Thr Val Asp Lys Ser Arg Trp Gln Gln
        195                 200                 205

Gly Asn Val Phe Ser Cys Ser Val Met His Glu Ala Leu His Asn His
    210                 215                 220

Tyr Thr Gln Lys Ser Leu Ser Leu Ser Pro Gly Lys
225                 230                 235

<210> SEQ ID NO 70
<211> LENGTH: 753
<212> TYPE: DNA
<213> ORGANISM: Artificial Sequence
<220> FEATURE:
<223> OTHER INFORMATION: Synthetic

<400> SEQUENCE: 70
aagaaggtgg tgatcggcaa gaagggcgac accgtggagc tgacctgcac cgccagccag      60
aagaagagca tccagttcca ctggaagaac agcaaccaga tcaagatcct gggcaaccag     120
ggcagcttcc tgaccaaggg acctagcaag ctgaacgaca gggtagacag ccggcggagc     180
ctgtgggacc agggaaactt cccactgatc atcaagaacc tgaagcctga ggacagcgac     240
acctacatct gcgaggtgga ggaccagaag gaggaggtgc agctgatagt gctaggcgga     300
gggggtggca gcggtggcgg gggaagtggc ggtggaggga gcggtggagg cggttcaggc     360
ggaggtggct ctggcggtgg cggatcaggg ggcgaggta gtgggggagg gggatcgggt     420 ggggaggca gcgggcagcc ccgagaacca caggtgtaca ccctgccccc atcccgggat     480
gagctgacca gaaccaggt cagcctgacc tgcctggtca aaggcttcta tcccagcgac     540
atcgccgtgg agtgggagag caatgggcag ccggagaaca actacaagac cacgcctccc     600
gtgctggact ccgacggctc cttcttcctc tacagcaagc tcaccgtgga caagagcagg     660
tggcagcagg ggaacgtctt ctcatgctcc gtgatgcatg aggctctgca caaccactac     720
acgcagaaga gcctctccct gtctccgggt aaa                                  753

<210> SEQ ID NO 71
<211> LENGTH: 251
<212> TYPE: PRT
<213> ORGANISM: Artificial Sequence
<220> FEATURE:
<223> OTHER INFORMATION: Synthetic

<400> SEQUENCE: 71

Lys Lys Val Val Ile Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Ser Leu Trp Asp Gln
50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Ile
                85                  90                  95

Val Leu Gly Gly Gly Gly Ser Gly Gly Gly Ser Gly Gly
            100                 105                 110

Gly Ser Gly Gly Gly Ser Gly Gly Gly Ser Gly Gly Gly
        115                 120                 125

Ser Gly Gly Gly Gly Ser Gly Gly Gly Ser Gly Gly Gly Ser
    130                 135                 140

Gly Gln Pro Arg Glu Pro Gln Val Tyr Thr Leu Pro Pro Ser Arg Asp
145                 150                 155                 160

Glu Leu Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Val Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys
                245                 250

<210> SEQ ID NO 72
<211> LENGTH: 1059
<212> TYPE: DNA
<213> ORGANISM: Artificial Sequence
<220> FEATURE:
<223> OTHER INFORMATION: Synthetic

<400> SEQUENCE: 72
caggtgcagc tggtgcagtc tgggggaggc ttggtacagc ctggagggtc cctgagactc      60
tcctgtgcag cctctgcttt cgatttctct gattatgaaa tgagctgggt ccgcgaggct     120
ccagggaagg ggctggagtg gattgggaa atcaatgata gtggaaacac catttacaat     180
ccgtccctca agagtcgagt caccatctcc agagacaatt ccaagaacac actgtatctg     240
caaatgaaca ccctgagagc cgaggacaca gccatatatt actgtgcgat atatggtggt     300
aactccgggg gagagtactg ggccagggc accctggtca ccgtctcctc aggaggggt     360 ggcagcggag gcggggaag tggcggtgga gggagcaaga aggtggtgat cggcaagaag     420
ggcgacaccg tggagctgac ctgcaccgcc agccagaaga gagcatcca gttccactgg     480 aagaacagca accagatcaa gatcctgggc aaccagggca gcttcctgac caagggacct     540
agcaagctga cgacagggt agacagccgg cggagcctgt gggaccaggg aaacttccca     600

```
ctgatcatca agaacctgaa gcctgaggac agcgacacct acatctgcga ggtggaggac    660
cagaaggagg aggtgcagct gatagtgcta ggcggagggg gtggcagcgg aggcggggga    720
agtggcggtg agggagcggg gcagccccga gaaccacagg tgtacaccct gcccccatcc    780
cgggatgagc tgaccaagaa ccaggtcagc ctgacctgcc tggtcaaagg cttctatccc    840
agcgacatcg ccgtggagtg ggagagcaat gggcagccgg agaacaacta caagaccacg    900
cctcccgtgc tggactccga cggctccttc ttcctctaca gcaagctcac cgtggacaag    960
agcaggtgga gcaggggaa cgtcttctca tgctccgtga tgcatgaggc tctgcacaac    1020
cactacacgc agaagagcct ctccctgtct ccgggtaaa                           1059
```

<210> SEQ ID NO 73
<211> LENGTH: 353
<212> TYPE: PRT
<213> ORGANISM: Artificial Sequence
<220> FEATURE:
<223> OTHER INFORMATION: Synthetic

<400> SEQUENCE: 73

```
Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Lys Lys Val Val Ile Gly Lys Lys Gly Asp Thr Val
    130                 135                 140

Glu Leu Thr Cys Thr Ala Ser Gln Lys Lys Ser Ile Gln Phe His Trp
145                 150                 155                 160

Lys Asn Ser Asn Gln Ile Lys Ile Leu Gly Asn Gln Gly Ser Phe Leu
                165                 170                 175

Thr Lys Gly Pro Ser Lys Leu Asn Asp Arg Val Asp Ser Arg Arg Ser
            180                 185                 190

Leu Trp Asp Gln Gly Asn Phe Pro Leu Ile Ile Lys Asn Leu Lys Pro
        195                 200                 205

Glu Asp Ser Asp Thr Tyr Ile Cys Glu Val Glu Asp Gln Lys Glu Glu
    210                 215                 220

Val Gln Leu Ile Val Leu Gly Gly Gly Gly Ser Gly Gly Gly Gly
225                 230                 235                 240

Ser Gly Gly Gly Gly Ser Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285
```

```
Ser Asn Gly Gln Pro Glu Asn Asn Tyr Lys Thr Thr Pro Pro Val Leu
    290                 295                 300
Asp Ser Asp Gly Ser Phe Phe Leu Tyr Ser Lys Leu Thr Val Asp Lys
305                 310                 315                 320
Ser Arg Trp Gln Gln Gly Asn Val Phe Ser Cys Ser Val Met His Glu
                325                 330                 335
Ala Leu His Asn His Tyr Thr Gln Lys Ser Leu Ser Leu Ser Pro Gly
            340                 345                 350
Lys

<210> SEQ ID NO 74
<211> LENGTH: 1380
<212> TYPE: DNA
<213> ORGANISM: Artificial Sequence
<220> FEATURE:
<223> OTHER INFORMATION: Synthetic

<400> SEQUENCE: 74
```

| | | | | | |
|---|---|---|---|---|---|
| caggtgcagc | tggtgcagtc | tggggggaggc | ttggtacagc | ctggagggtc | cctgagactc | 60 |
| tcctgtgcag | cctctgcttt | cgatttctct | gattatgaaa | tgagctgggt | ccgcgaggct | 120 |
| ccagggaagg | gctggagtg | gattggggaa | atcaatgata | gtggaaacac | catttacaat | 180 |
| ccgtccctca | agagtcgagt | caccatctcc | agagacaatt | ccaagaacac | actgtatctg | 240 |
| caaatgaaca | ccctgagagc | cgaggacaca | gccatatatt | actgtgcgat | atatggtggt | 300 |
| aactccgggg | gagagtactg | gggccaggge | accctggtca | ccgtctcctc | aggagggggt | 360 |
| ggcagcggag | gcgggggaag | tggcggtgga | gggagcaaga | aggtggtgat | cggcaagaag | 420 |
| ggcgacaccg | tggagctgac | ctgcaccgcc | agccagaaga | gagcatcca | gttccactgg | 480 |
| aagaacagca | accagatcaa | gatcctgggc | aaccagggca | gcttcctgac | caagggacct | 540 |
| agcaagctga | cgacagggt | agacagccgg | cggagcctgt | gggaccaggg | aaacttccca | 600 |
| ctgatcatca | agaacctgaa | gcctgaggac | agcgacacct | acatctgcga | ggtggaggac | 660 |
| cagaaggagg | aggtgcagct | gatagtgcta | ggcgggcccg | acaaaactca | cacatgccca | 720 |
| ccgtgcccag | cacctgaact | cctggggga | ccgtcagtct | tcctcttccc | cccaaaaccc | 780 |
| aaggacaccc | tcatgatctc | ccggacccct | gaggtcacat | gcgtggtggt | ggacgtgagc | 840 |
| cacgaagacc | ctgaggtcaa | gttcaactgg | tacgtggacg | gcgtggaggt | gcataatgcc | 900 |
| aagacaaagc | cgcgggagga | gcagtacaac | agcacgtacc | gtgtggtcag | cgtcctcacc | 960 |
| gtcctgcacc | aggactggct | gaatggcaag | gagtacaagt | gcaaggtctc | caacaaagcc | 1020 |
| ctcccagccc | ccatcgagaa | aaccatctcc | aaagccaaag | gcagccccg | agaaccacag | 1080 |
| gtgtacaccc | tgcccccatc | ccgggatgag | ctgaccaaga | accaggtcag | cctgacctgc | 1140 |
| ctggtcaaag | gcttctatcc | cagcgacatc | gccgtggagt | gggagagcaa | tgggcagccg | 1200 |
| gagaacaact | acaagaccac | gcctcccgtg | ctggactccg | acggctcctt | cttcctctac | 1260 |
| agcaagctca | ccgtggacaa | gagcaggtgg | cagcagggga | acgtcttctc | atgctccgtg | 1320 |
| atgcatgagg | ctctgcacaa | ccactacacg | cagaagagcc | tctccctgtc | tccgggtaaa | 1380 |

```
<210> SEQ ID NO 75
<211> LENGTH: 460
<212> TYPE: PRT
<213> ORGANISM: Artificial Sequence
<220> FEATURE:
<223> OTHER INFORMATION: Synthetic
```

<400> SEQUENCE: 75

```
Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Ser Gly Gly Gly Gly Ser Gly
        115                 120                 125

Gly Gly Gly Ser Lys Lys Val Val Ile Gly Lys Lys Gly Asp Thr Val
    130                 135                 140

Glu Leu Thr Cys Thr Ala Ser Gln Lys Lys Ser Ile Gln Phe His Trp
145                 150                 155                 160

Lys Asn Ser Asn Gln Ile Lys Ile Leu Gly Asn Gln Gly Ser Phe Leu
                165                 170                 175

Thr Lys Gly Pro Ser Lys Leu Asn Asp Arg Val Asp Ser Arg Arg Ser
            180                 185                 190

Leu Trp Asp Gln Gly Asn Phe Pro Leu Ile Ile Lys Asn Leu Lys Pro
        195                 200                 205

Glu Asp Ser Asp Thr Tyr Ile Cys Glu Val Glu Asp Gln Lys Glu Glu
    210                 215                 220

Val Gln Leu Ile Val Leu Gly Pro Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
        355                 360                 365

Asp Glu Leu Thr Lys Asn Gln Val Ser Leu Thr Cys Leu Val Lys Gly
    370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
                405                 410                 415
```

```
Phe Phe Leu Tyr Ser Lys Leu Thr Val Asp Lys Ser Arg Trp Gln Gln
                420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
        450                 455                 460

<210> SEQ ID NO 76
<211> LENGTH: 55
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (35)..(36)
<223> OTHER INFORMATION: Wherein N is any nucleic acid

<400> SEQUENCE: 76
cgctaccgtg gcccaggcgg ccaagaaggt ggtgnnsggc aagaagggcg acacc      55

<210> SEQ ID NO 77
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (23)..(24)
<223> OTHER INFORMATION: Wherein N is any nucleic acid
<220> FEATURE:
<221> NAME/KEY: misc_feature
<222> LOCATION: (29)..(30)
<223> OTHER INFORMATION: Wherein N is any nucleic acid

<400> SEQUENCE: 77
gtggtggccg gcctggccgc cwnncacwnn cagctgcacc tcctccttct ggtcctccac    60
ctcgcagatg ta                                                       72

<210> SEQ ID NO 78
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (29)..(30)
<223> OTHER INFORMATION: Wherein N is any nucleic acid

<400> SEQUENCE: 78
ctcgcagatg taggtgtcgc tgtcctcwnn cttcaggttc ttgatgatca g            51

<210> SEQ ID NO 79
<211> LENGTH: 37
<212> TYPE: DNA
<213> ORGANISM: Artificial Sequence
<220> FEATURE:
<223> OTHER INFORMATION: Synthetic

<400> SEQUENCE: 79
tgacgcggcc cagccggcca agaaggtggt gatcggc                             37

<210> SEQ ID NO 80
<211> LENGTH: 50
```

```
<212> TYPE: DNA
<213> ORGANISM: Artificial Sequence
<220> FEATURE:
<223> OTHER INFORMATION: Synthetic

<400> SEQUENCE: 80
cgggtttaaa ctcagtggtg gtggtggtgg tggcctagca ctatcagctg          50

<210> SEQ ID NO 81
<211> LENGTH: 37
<212> TYPE: DNA
<213> ORGANISM: Artificial Sequence
<220> FEATURE:
<223> OTHER INFORMATION: Synthetic

<400> SEQUENCE: 81
tgacgcggcc cagccggcca agaaggtggt gtacggc                        37

<210> SEQ ID NO 82
<211> LENGTH: 50
<212> TYPE: DNA
<213> ORGANISM: Artificial Sequence
<220> FEATURE:
<223> OTHER INFORMATION: Synthetic

<400> SEQUENCE: 82
cgggtttaaa ctcagtggtg gtggtggtgg tggcctacca ctaccagctg          50

<210> SEQ ID NO 83
<211> LENGTH: 18
<212> TYPE: DNA
<213> ORGANISM: Artificial Sequence
<220> FEATURE:
<223> OTHER INFORMATION: Synthetic

<400> SEQUENCE: 83
gcacctgaac tcctgggg                                             18

<210> SEQ ID NO 84
<211> LENGTH: 51
<212> TYPE: DNA
<213> ORGANISM: Artificial Sequence
<220> FEATURE:
<223> OTHER INFORMATION: Synthetic

<400> SEQUENCE: 84
tcaggcggag gtggctctgg cggtggcgga tcagcacctg aactcctggg g         51

<210> SEQ ID NO 85
<211> LENGTH: 50
<212> TYPE: DNA
<213> ORGANISM: Artificial Sequence
<220> FEATURE:
<223> OTHER INFORMATION: Synthetic

<400> SEQUENCE: 85
cgggtttaaa ctcagtggtg gtggtggtgg tgtttggctt tggagatggt          50

<210> SEQ ID NO 86
<211> LENGTH: 37
<212> TYPE: DNA
<213> ORGANISM: Artificial Sequence
<220> FEATURE:
<223> OTHER INFORMATION: Synthetic

<400> SEQUENCE: 86
```

```
taccgtggcc caggcggccc aggtgcagct ggtgcag                              37
```

<210> SEQ ID NO 87
<211> LENGTH: 45
<212> TYPE: DNA
<213> ORGANISM: Artificial Sequence
<220> FEATURE:
<223> OTHER INFORMATION: Synthetic

<400> SEQUENCE: 87

```
acttcccccg cctccgctgc cacccctcc tgaggagacg gtgac                      45
```

<210> SEQ ID NO 88
<211> LENGTH: 48
<212> TYPE: DNA
<213> ORGANISM: Artificial Sequence
<220> FEATURE:
<223> OTHER INFORMATION: Synthetic

<400> SEQUENCE: 88

```
agcggaggcg ggggaagtgg cggtggaggg agcaagaagg tggtgatc                  48
```

<210> SEQ ID NO 89
<211> LENGTH: 33
<212> TYPE: DNA
<213> ORGANISM: Artificial Sequence
<220> FEATURE:
<223> OTHER INFORMATION: Synthetic

<400> SEQUENCE: 89

```
gtggtggccg gcctggccgc ctagcactat cag                                  33
```

<210> SEQ ID NO 90
<211> LENGTH: 75
<212> TYPE: DNA
<213> ORGANISM: Artificial Sequence
<220> FEATURE:
<223> OTHER INFORMATION: Synthetic

<400> SEQUENCE: 90

```
tgaaccgcct ccaccgctcc ctccaccgcc acttcccccg ccaccgctgc cacccctcc      60 tgaggagacg gtgac                                                      75
```

<210> SEQ ID NO 91
<211> LENGTH: 63
<212> TYPE: DNA
<213> ORGANISM: Artificial Sequence
<220> FEATURE:
<223> OTHER INFORMATION: Synthetic

<400> SEQUENCE: 91

```
agcggtggag gcggttcagg cggaggtggc tctggcggtg gcggatcaaa gaaggtggtg     60
atc                                                                   63
```

<210> SEQ ID NO 92
<211> LENGTH: 90
<212> TYPE: DNA
<213> ORGANISM: Artificial Sequence
<220> FEATURE:
<223> OTHER INFORMATION: Synthetic

<400> SEQUENCE: 92

```
agagccacct ccgcctgaac cgcctccacc gctccctcca ccgccacttc ccccgcctcc     60
gctgccaccc cctcctgagg agacggtgac                                      90
```

```
<210> SEQ ID NO 93
<211> LENGTH: 93
<212> TYPE: DNA
<213> ORGANISM: Artificial Sequence
<220> FEATURE:
<223> OTHER INFORMATION: Synthetic

<400> SEQUENCE: 93
tcaggcggag gtggctctgg cggtggcgga tcaggggcg gaggtagtgg gggaggggga      60
tcgggtgggg gaggcagcaa gaaggtggtg atc                                  93

<210> SEQ ID NO 94
<211> LENGTH: 34
<212> TYPE: DNA
<213> ORGANISM: Artificial Sequence
<220> FEATURE:
<223> OTHER INFORMATION: Synthetic

<400> SEQUENCE: 94
taccgtggcc caggcggcca agaaggtggt gatc                                 34

<210> SEQ ID NO 95
<211> LENGTH: 45
<212> TYPE: DNA
<213> ORGANISM: Artificial Sequence
<220> FEATURE:
<223> OTHER INFORMATION: Synthetic

<400> SEQUENCE: 95
acttcccccg cctccgctgc cacccctcc gcctagcact atcag                      45

<210> SEQ ID NO 96
<211> LENGTH: 48
<212> TYPE: DNA
<213> ORGANISM: Artificial Sequence
<220> FEATURE:
<223> OTHER INFORMATION: Synthetic

<400> SEQUENCE: 96
agcggaggcg ggggaagtgg cggtggaggg agcgggcagc cccgagaa                  48

<210> SEQ ID NO 97
<211> LENGTH: 33
<212> TYPE: DNA
<213> ORGANISM: Artificial Sequence
<220> FEATURE:
<223> OTHER INFORMATION: Synthetic

<400> SEQUENCE: 97
gtggtggccg gcctggcctt tacccggaga cag                                  33

<210> SEQ ID NO 98
<211> LENGTH: 75
<212> TYPE: DNA
<213> ORGANISM: Artificial Sequence
<220> FEATURE:
<223> OTHER INFORMATION: Synthetic

<400> SEQUENCE: 98
tgaaccgcct ccaccgctcc ctccaccgcc acttcccccg ccaccgctgc cacccctcc      60 gcctagcact atcag                                                      75

<210> SEQ ID NO 99
```

```
<211> LENGTH: 63
<212> TYPE: DNA
<213> ORGANISM: Artificial Sequence
<220> FEATURE:
<223> OTHER INFORMATION: Synthetic

<400> SEQUENCE: 99
agcggtggag gcggttcagg cggaggtggc tctggcggtg gcggatcagg gcagccccga    60
gaa                                                                  63

<210> SEQ ID NO 100
<211> LENGTH: 90
<212> TYPE: DNA
<213> ORGANISM: Artificial Sequence
<220> FEATURE:
<223> OTHER INFORMATION: Synthetic

<400> SEQUENCE: 100
agagccacct ccgcctgaac cgcctccacc gctccctcca ccgccacttc ccccgcctcc    60
gctgccaccc cctccgccta gcactatcag                                     90

<210> SEQ ID NO 101
<211> LENGTH: 93
<212> TYPE: DNA
<213> ORGANISM: Artificial Sequence
<220> FEATURE:
<223> OTHER INFORMATION: Synthetic

<400> SEQUENCE: 101
tcaggcggag gtggctctgg cggtggcgga tcaggggggcg gaggtagtgg gggagggga    60 tcgggtgggg gaggcagcgg gcagccccga gaa                                 93

<210> SEQ ID NO 102
<211> LENGTH: 47
<212> TYPE: DNA
<213> ORGANISM: Artificial Sequence
<220> FEATURE:
<223> OTHER INFORMATION: Synthetic

<400> SEQUENCE: 102
cgggtttaaa ctcagtggtg gtggtggtgg tgtttacccg gagacag                  47

<210> SEQ ID NO 103
<211> LENGTH: 37
<212> TYPE: DNA
<213> ORGANISM: Artificial Sequence
<220> FEATURE:
<223> OTHER INFORMATION: Synthetic

<400> SEQUENCE: 103
tgacgcggcc cagccggccc aggtgcagct ggtgcag                             37

<210> SEQ ID NO 104
<211> LENGTH: 18
<212> TYPE: DNA
<213> ORGANISM: Artificial Sequence
<220> FEATURE:
<223> OTHER INFORMATION: Synthetic

<400> SEQUENCE: 104
gcctagcact atcagctg                                                  18

<210> SEQ ID NO 105
<211> LENGTH: 18
```

```
<212> TYPE: DNA
<213> ORGANISM: Artificial Sequence
<220> FEATURE:
<223> OTHER INFORMATION: Synthetic

<400> SEQUENCE: 105
cagctgatag tgctaggc                                                      18

<210> SEQ ID NO 106
<211> LENGTH: 30
<212> TYPE: DNA
<213> ORGANISM: Artificial Sequence
<220> FEATURE:
<223> OTHER INFORMATION: Synthetic

<400> SEQUENCE: 106
tttgtcgggc ccgcctagca ctatcagctg                                         30

<210> SEQ ID NO 107
<211> LENGTH: 37
<212> TYPE: DNA
<213> ORGANISM: Artificial Sequence
<220> FEATURE:
<223> OTHER INFORMATION: Synthetic

<400> SEQUENCE: 107
tgacgcggcc cagccggccg aggtggtgct gggcaac                                 37

<210> SEQ ID NO 108
<211> LENGTH: 78
<212> TYPE: DNA
<213> ORGANISM: Artificial Sequence
<220> FEATURE:
<223> OTHER INFORMATION: Synthetic

<400> SEQUENCE: 108
tgaaccgcct ccaccgcttc ctcctcctcc ggatcctcct ccgccggatc ctcctcctcc        60
ctcgatcttc accacctt                                                      78

<210> SEQ ID NO 109
<211> LENGTH: 33
<212> TYPE: DNA
<213> ORGANISM: Artificial Sequence
<220> FEATURE:
<223> OTHER INFORMATION: Synthetic

<400> SEQUENCE: 109
ggtggaggcg gttcaaagaa ggtggtgtac ggc                                     33

<210> SEQ ID NO 110
<211> LENGTH: 33
<212> TYPE: DNA
<213> ORGANISM: Artificial Sequence
<220> FEATURE:
<223> OTHER INFORMATION: Synthetic

<400> SEQUENCE: 110
ggtggaggcg gttcaaagaa ggtggtgctg ggc                                     33

<210> SEQ ID NO 111
<211> LENGTH: 50
<212> TYPE: DNA
<213> ORGANISM: Artificial Sequence
<220> FEATURE:
<223> OTHER INFORMATION: Synthetic
```

<400> SEQUENCE: 111
cgggtttaaa ctcagtggtg gtggtggtgg tgggccagca ccacgatgtc          50

<210> SEQ ID NO 112
<211> LENGTH: 50
<212> TYPE: DNA
<213> ORGANISM: Artificial Sequence
<220> FEATURE:
<223> OTHER INFORMATION: Synthetic

<400> SEQUENCE: 112
cgggtttaaa ctcagtggtg gtggtggtgg tgctcgatct tcaccacctt          50

<210> SEQ ID NO 113
<211> LENGTH: 36
<212> TYPE: DNA
<213> ORGANISM: Artificial Sequence
<220> FEATURE:
<223> OTHER INFORMATION: Synthetic

<400> SEQUENCE: 113
cttacagatg ccagatgtca ggtgcagctg gtgcag                        36

<210> SEQ ID NO 114
<211> LENGTH: 48
<212> TYPE: DNA
<213> ORGANISM: Artificial Sequence
<220> FEATURE:
<223> OTHER INFORMATION: Synthetic

<400> SEQUENCE: 114
agagccacct ccgcctgaac cgcctccacc tgaggagacg gtgaccag            48

<210> SEQ ID NO 115
<211> LENGTH: 51
<212> TYPE: DNA
<213> ORGANISM: Artificial Sequence
<220> FEATURE:
<223> OTHER INFORMATION: Synthetic

<400> SEQUENCE: 115
tcaggcggag gtggctctgg cggtggcgga tcacgaactg tggctgcacc a         51

<210> SEQ ID NO 116
<211> LENGTH: 36
<212> TYPE: DNA
<213> ORGANISM: Artificial Sequence
<220> FEATURE:
<223> OTHER INFORMATION: Synthetic

<400> SEQUENCE: 116
actacaggtg tccactccaa gaaggtggtg atcggc                        36

<210> SEQ ID NO 117
<211> LENGTH: 73
<212> TYPE: DNA
<213> ORGANISM: Artificial Sequence
<220> FEATURE:
<223> OTHER INFORMATION: Synthetic

<400> SEQUENCE: 117
ccttggagct cgatccgcca ccgccagagc cacctccgcc tgaaccgcct ccaccgccta    60
gcactatcag ctg                                                  73

<210> SEQ ID NO 118
<211> LENGTH: 24
<212> TYPE: DNA
<213> ORGANISM: Artificial Sequence
<220> FEATURE:
<223> OTHER INFORMATION: Synthetic

<400> SEQUENCE: 118
taattctcta gagccgccac catg                                      24

<210> SEQ ID NO 119
<211> LENGTH: 48
<212> TYPE: DNA
<213> ORGANISM: Artificial Sequence
<220> FEATURE:
<223> OTHER INFORMATION: Synthetic

<400> SEQUENCE: 119
agagccacct ccgcctgaac cgcctccacc tttacccgga gacaggga            48

<210> SEQ ID NO 120
<211> LENGTH: 51
<212> TYPE: DNA
<213> ORGANISM: Artificial Sequence
<220> FEATURE:
<223> OTHER INFORMATION: Synthetic

<400> SEQUENCE: 120
tcaggcggag gtggctctgg cggtggcgga tcaaagaagg tggtgatcgg c        51

<210> SEQ ID NO 121
<211> LENGTH: 30
<212> TYPE: DNA
<213> ORGANISM: Artificial Sequence
<220> FEATURE:
<223> OTHER INFORMATION: Synthetic

<400> SEQUENCE: 121
ccgtcgcact cagcctagca ctatcagctg                                30

<210> SEQ ID NO 122
<211> LENGTH: 18
<212> TYPE: DNA
<213> ORGANISM: Artificial Sequence
<220> FEATURE:
<223> OTHER INFORMATION: Synthetic

<400> SEQUENCE: 122
tgagtgcgac ggccggca                                             18

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123
cccgaggtcg acgctctc                                             18

<210> SEQ ID NO 124
<211> LENGTH: 48
<212> TYPE: DNA
<213> ORGANISM: Artificial Sequence
<220> FEATURE:
<223> OTHER INFORMATION: Synthetic

<400> SEQUENCE: 124
acttcccccg ccaccgctgc cacccctcc acactctccc ctgttgaa            48

<210> SEQ ID NO 125
<211> LENGTH: 51
<212> TYPE: DNA
<213> ORGANISM: Artificial Sequence
<220> FEATURE:
<223> OTHER INFORMATION: Synthetic

<400> SEQUENCE: 125
agcggtggcg ggggaagtgg cggtggaggg agcaagaagg tggtgatcgg c        51

<210> SEQ ID NO 126
<211> LENGTH: 34
<212> TYPE: DNA
<213> ORGANISM: Artificial Sequence
<220> FEATURE:
<223> OTHER INFORMATION: Synthetic

<400> SEQUENCE: 126
atcaatgaat tcattagcct agcactatca gctg                          34

<210> SEQ ID NO 127
<211> LENGTH: 46
<212> TYPE: DNA
<213> ORGANISM: Artificial Sequence
<220> FEATURE:
<223> OTHER INFORMATION: Synthetic

<400> SEQUENCE: 127
gtgtaagctt accatgggtg tgcccactca ggtcctgggg ttgctg              46

<210> SEQ ID NO 128
<211> LENGTH: 36
<212> TYPE: DNA
<213> ORGANISM: Artificial Sequence
<220> FEATURE:
<223> OTHER INFORMATION: Synthetic

<400> SEQUENCE: 128
cttacagatg ccagatgtga tgttgtgatg actcag                        36

<210> SEQ ID NO 129
<211> LENGTH: 42
<212> TYPE: DNA
<213> ORGANISM: Artificial Sequence
<220> FEATURE:
<223> OTHER INFORMATION: Synthetic

<400> SEQUENCE: 129
acatctggca tctgtaagcc acagcagcag caaccccagg ac                 42

<210> SEQ ID NO 130
<211> LENGTH: 32
<212> TYPE: DNA
<213> ORGANISM: Artificial Sequence
<220> FEATURE:
<223> OTHER INFORMATION: Synthetic

<400> SEQUENCE: 130
gtgtgaattc attaacactc tcccctgttg aa                            32

<210> SEQ ID NO 131
<211> LENGTH: 46

<210> SEQ ID NO 132
<211> LENGTH: 42
<212> TYPE: DNA
<213> ORGANISM: Artificial Sequence
<220> FEATURE:
<223> OTHER INFORMATION: Synthetic

<400> SEQUENCE: 131
gtgttctaga gccgccacca tggaatggag ctgggtcttt ctcttc    46

<210> SEQ ID NO 132
<211> LENGTH: 42
<212> TYPE: DNA
<213> ORGANISM: Artificial Sequence
<220> FEATURE:
<223> OTHER INFORMATION: Synthetic

<400> SEQUENCE: 132
ggagtggaca cctgtagtta ctgacaggaa gaagagaaag ac    42

<210> SEQ ID NO 133
<211> LENGTH: 1680
<212> TYPE: DNA
<213> ORGANISM: Artificial Sequence
<220> FEATURE:
<223> OTHER INFORMATION: Synthetic

<400> SEQUENCE: 133
aagaaggtgg tgatcggcaa gaagggcgac accgtggagc tgacctgcac cgccagccag    60
aagaagagca tccagttcca ctggaagaac agcaaccaga tcaagatcct gggcaaccag    120
ggcagcttcc tgaccaaggg acctagcaag ctgaacgaca gggtagacag ccggcggagc    180
ctgtgggacc agggaaactt cccactgatc atcaagaacc tgaagcctga ggacagcgac    240
acctacatct gcgaggtgga ggaccagaag gaggaggtgc agctgatagt gctaggcggt    300
ggaggcggtt caggcggagg tggctctggc ggtggcggat cgagctcagc ctccaccaag    360
ggcccatcgg tcttccccct ggcaccctcc tccaagagca cctctggggg cacagcggcc    420
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca gcccagcaa caccaaggtg gacaagaaag ttgagcccaa atcttgtgac    660
aaaactcaca catgcccacc gtgcccagca cctgaactcc tggggggacc gtcagtcttc    720
ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cccagccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct cctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaagg tggaggcggt tcaggcggag gtggctctgg cggtggcgga    1380
tcaaagaagg tggtgatcgg caagaagggc gacaccgtgg agctgacctg caccgccagc    1440

-continued

```
cagaagaaga gcatccagtt ccactggaag aacagcaacc agatcaagat cctgggcaac    1500
cagggcagct tcctgaccaa gggacctagc aagctgaacg acagggtaga cagccggcgg    1560
agcctgtggg accagggaaa cttcccactg atcatcaaga acctgaagcc tgaggacagc    1620
gacacctaca tctgcgaggt ggaggaccag aaggaggagg tgcagctgat agtgctaggc    1680
```

<210> SEQ ID NO 134
<211> LENGTH: 560
<212> TYPE: PRT
<213> ORGANISM: Artificial Sequence
<220> FEATURE:
<223> OTHER INFORMATION: Synthetic

<400> SEQUENCE: 134

```
Lys Lys Val Val Ile Gly Lys Lys Gly Asp Thr Val Glu Leu Thr Cys
1               5                   10                  15

Thr Ala Ser Gln Lys Lys Ser Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Asp Gln Lys Glu Glu Val Gln Leu Ile
                85                  90                  95

Val Leu Gly Gly Gly Gly Ser Gly Gly Gly Ser Gly Gly Gly
            100                 105                 110

Gly Ser Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
```

```
                  325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
        370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys Gly Gly
            435                 440                 445
Gly Gly Ser Gly Gly Gly Gly Ser Gly Gly Gly Gly Ser Lys Lys Val
        450                 455                 460
Val Ile Gly Lys Lys Gly Asp Thr Val Glu Leu Thr Cys Thr Ala Ser
465                 470                 475                 480
Gln Lys Lys Ser Ile Gln Phe His Trp Lys Asn Ser Asn Gln Ile Lys
                485                 490                 495
Ile Leu Gly Asn Gln Gly Ser Phe Leu Thr Lys Gly Pro Ser Lys Leu
            500                 505                 510
Asn Asp Arg Val Asp Ser Arg Arg Ser Leu Trp Asp Gln Gly Asn Phe
            515                 520                 525
Pro Leu Ile Ile Lys Asn Leu Lys Pro Glu Asp Ser Asp Thr Tyr Ile
        530                 535                 540
Cys Glu Val Glu Asp Gln Lys Glu Glu Val Gln Leu Ile Val Leu Gly
545                 550                 555                 560

<210> SEQ ID NO 135
<211> LENGTH: 1059
<212> TYPE: DNA
<213> ORGANISM: Artificial Sequence
<220> FEATURE:
<223> OTHER INFORMATION: Synthetic

<400> SEQUENCE: 135
caggtgcagc tggtgcagtc tggggggaggc ttggtacagc ctggagggtc cctgagactc      60
tcctgtgcag cctctgcttt cgatttctct gattatgaaa tgagctgggt ccgcgaggct     120
ccagggaagg ggctggagtg gattgggaa atcaatgata gtggaaacac catttacaat     180
ccgtccctca agagtcgagt caccatctcc agagacaatt ccaagaacac actgtatctg     240
caaatgaaca ccctgagagc cgaggacaca gccatatatt actgtgcgat atatggtggt     300
aactccgggg gagagtactg gggccagggc accctggtca ccgtctcctc aggtggaggc     360
ggttcaggcg gaggtggctc tggcggtggc ggatcacgaa ctgtggctgc accatctgtc     420
ttcatcttcc cgccatctga tgagcagttg aaatctggaa ctgcctctgt tgtgtgcctg     480
ctgaataact tctatcccag agaggccaaa gtacagtgga aggtggataa cgccctccaa     540
tcgggtaact cccaggagag tgtcacagag caggacagca aggacagcac ctacagcctc     600
agcagcaccc tgacgctgag caaagcagac tacgagaaac acaaagtcta cgcctgcgaa     660
gtcacccatc agggcctgag ctcgcccgtc acaaagagct tcaacagggg agagtgtgga     720
gggggtggca gcggtggcgg gggaagtggc ggtggaggga gcaagaaggt ggtgatcggc     780
```

```
aagaagggcg acaccgtgga gctgacctgc accgccagcc agaagaagag catccagttc    840
cactggaaga acagcaacca gatcaagatc ctgggcaacc agggcagctt cctgaccaag    900
ggacctagca agctgaacga cagggtagac agccggcgga gcctgtggga ccagggaaac    960
ttcccactga tcatcaagaa cctgaagcct gaggacagcg acacctacat ctgcgaggtg   1020
gaggaccaga aggaggaggt gcagctgata gtgctaggc                          1059
```

<210> SEQ ID NO 136
<211> LENGTH: 353
<212> TYPE: PRT
<213> ORGANISM: Artificial Sequence
<220> FEATURE:
<223> OTHER INFORMATION: Synthetic

<400> SEQUENCE: 136

```
Gln Val Gln Leu Val Gln Ser Gly Gly Gly Leu Val Gln Pro Gly Gly
1               5                   10                  15

Ser Leu Arg Leu Ser Cys Ala Ala Ser Ala Phe Asp Phe Ser Asp Tyr
            20                  25                  30

Glu Met Ser Trp Val Arg Glu Ala Pro Gly Lys Gly Leu Glu Trp Ile
        35                  40                  45

Gly Glu Ile Asn Asp Ser Gly Asn Thr Ile Tyr Asn Pro Ser Leu Lys
    50                  55                  60

Ser Arg Val Thr Ile Ser Arg Asp Asn Ser Lys Asn Thr Leu Tyr Leu
65                  70                  75                  80

Gln Met Asn Thr Leu Arg Ala Glu Asp Thr Ala Ile Tyr Tyr Cys Ala
                85                  90                  95

Ile Tyr Gly Gly Asn Ser Gly Gly Glu Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Gln Ser Gly Asn Ser Gln Glu Ser Val Thr Glu Gln Asp
            180                 185                 190

Ser Lys Asp Ser Thr Tyr Ser Leu Ser Ser Thr Leu Thr Leu Ser Lys
        195                 200                 205

Ala Asp Tyr Glu Lys His Lys Val Tyr Ala Cys Glu Val Thr His Gln
    210                 215                 220

Gly Leu Ser Ser Pro Val Thr Lys Ser Phe Asn Arg Gly Glu Cys Gly
225                 230                 235                 240

Gly Gly Gly Ser Gly Gly Gly Gly Ser Gly Gly Gly Gly Ser Lys Lys
                245                 250                 255

Val Val Ile Gly Lys Lys Gly Asp Thr Val Glu Leu Thr Cys Thr Ala
            260                 265                 270

Ser Gln Lys Lys Ser Ile Gln Phe His Trp Lys Asn Ser Asn Gln Ile
        275                 280                 285

Lys Ile Leu Gly Asn Gln Gly Ser Phe Leu Thr Lys Gly Pro Ser Lys
    290                 295                 300

Leu Asn Asp Arg Val Asp Ser Arg Arg Ser Leu Trp Asp Gln Gly Asn
```

```
                305                 310                 315                 320
Phe Pro Leu Ile Ile Lys Asn Leu Lys Pro Glu Asp Ser Asp Thr Tyr
                    325                 330                 335
Ile Cys Glu Val Glu Asp Gln Lys Glu Val Gln Leu Ile Val Leu
                340                 345                 350
Gly

<210> SEQ ID NO 137
<211> LENGTH: 330
<212> TYPE: PRT
<213> ORGANISM: Artificial Sequence
<220> FEATURE:
<223> OTHER INFORMATION: Synthetic

<400> SEQUENCE: 137

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                    85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
```

```
Gln Lys Ser Leu Ser Leu Ser Pro Gly Lys
            325                 330

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 139
<211> LENGTH: 117
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (12)..(12)
<223> OTHER INFORMATION: Wherein Xaa can be any amino acid
<220> FEATURE:
<221> NAME/KEY: MISC_FEATURE
<222> LOCATION: (26)..(26)
<223> OTHER INFORMATION: Wherein Xaa can be any amino acid
<220> FEATURE:
<221> NAME/KEY: MISC_FEATURE
<222> LOCATION: (39)..(40)
<223> OTHER INFORMATION: Wherein Xaa can be any amino acid
<220> FEATURE:
<221> NAME/KEY: MISC_FEATURE
<222> LOCATION: (54)..(54)
<223> OTHER INFORMATION: Wherein Xaa can be any amino acid
<220> FEATURE:
<221> NAME/KEY: MISC_FEATURE
<222> LOCATION: (65)..(65)
<223> OTHER INFORMATION: Wherein Xaa can be any amino acid
<220> FEATURE:
<221> NAME/KEY: MISC_FEATURE
<222> LOCATION: (86)..(86)
<223> OTHER INFORMATION: Wherein Xaa can be any amino acid

<400> SEQUENCE: 139

Gln Val Gln Leu Val Gln Ser Gly Gly Gly Leu Xaa Gln Pro Gly Gly
1               5                   10                  15

Ser Leu Arg Leu Ser Cys Ala Ala Ser Xaa Phe Asp Phe Ser Asp Tyr
            20                  25                  30

Glu Met Ser Trp Val Arg Xaa Xaa Pro Gly Lys Gly Leu Glu Trp Ile
        35                  40                  45

Gly Glu Ile Asn Asp Xaa Gly Asn Thr Ile Tyr Asn Pro Ser Leu Lys
```

```
                    50                      55                      60
Xaa Arg Val Thr Ile Ser Arg Asp Asn Ser Lys Asn Thr Leu Tyr Leu
 65                      70                      75                      80

Gln Met Asn Thr Leu Xaa Ala Glu Asp Thr Ala Ile Tyr Tyr Cys Ala
                     85                      90                      95

Ile Tyr Gly Gly Asn Ser Gly Gly Glu Tyr Trp Gly Gln Gly Thr Leu
                100                     105                     110

Val Thr Val Ser Ser
                115
```